(12) United States Patent
Batoko et al.

(10) Patent No.: US 11,613,762 B2
(45) Date of Patent: Mar. 28, 2023

(54) PLANTS WITH MODIFIED LIPID METABOLISM AND METHODS FOR MAKING THE SAME

(71) Applicants: UNIVERSITÉ CATHOLIQUE DE LOUVAIN, Louvain-la-Neuve (BE); UNIVERSITE DE BORDEAUX, Bordeaux (FR); CENTRE NATIONAL DE LA RECHERCHE SCIENTIFIQUE, Paris (FR)

(72) Inventors: Henri Batoko, Luttre (BE); Patrick Moreau, Pessac (FR)

(73) Assignees: UNIVERSITÉ CATHOLIQUE DE LOUVAIN, Louvain-la-Neuve (BE); UNIVERSITE DE BORDEAUX, Bordeaux (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 4 days.

(21) Appl. No.: 16/641,492

(22) PCT Filed: Aug. 24, 2018

(86) PCT No.: PCT/EP2018/072878
§ 371 (c)(1),
(2) Date: Feb. 24, 2020

(87) PCT Pub. No.: WO2019/038422
PCT Pub. Date: Feb. 28, 2019

(65) Prior Publication Data
US 2021/0163974 A1  Jun. 3, 2021

(30) Foreign Application Priority Data
Aug. 25, 2017 (EP) .................................... 17290107

(51) Int. Cl.
C12N 15/82 (2006.01)
C07K 14/415 (2006.01)

(52) U.S. Cl.
CPC ........ *C12N 15/8247* (2013.01); *C07K 14/415* (2013.01)

(58) Field of Classification Search
CPC .......................... C12N 15/8247; C07K 14/415
See application file for complete search history.

(56) References Cited

FOREIGN PATENT DOCUMENTS

AU     199868135 B2   11/1998
WO     2004/074431     9/2004

OTHER PUBLICATIONS

Li et al (Oil content of *Arabidopsis* seeds: The influence of seed anatomy, light and plant-to-plant variation. Phytochemistry 67, 904-915, 2006). (Year: 2006).*
Kim et al (Genetic Modification of the Soybean to Enhance the b-Carotene Content through Seed-Specific Expression. PLOS ONE. 1-12, 2012). (Year: 2012).*
Selvaraj et al (Minireview: Translocator Protein (TSPO) and Steroidogenesis: A Reappraisal. Mol Endocrinol, 29(4):490-501, 2015) (Year: 2015).*
Guillaumot et al (The *Arabidopsis* TSPO-related protein is a stress and abscisic acid-regulated, endoplasmic reticulum-Golgi-localized membrane protein. The Plant Journal 60, 242-256, 2009) (Year: 2009).*
Veenman et al (Tetrapyrroles as Endogenous TSPO Ligands in Eukaryotes and Prokaryotes: Comparisons with Synthetic Ligands. Int. J. Mol. Sci. 2016, 17, 1-26, 2016) (Year: 2016).*
Sohrabi et al (Isolation and sequence analysis of napin seed specific promoter from Iranian Rapeseed (*Brassica napus* L.) Gene 563, 160-164, 2015). (Year: 2015).*
International Search Report dated Oct. 8, 2018 in International (PCT) Application No. PCT/EP2018/072878.
Veenman et al., "Tetrapyrroles as Endogenous TSPO Ligands in Eukaryotes and Prokaryotes: Comparisons with Synthetic Ligands", International Journal of Molecular Sciences, 2016, vol. 17, No. 6, p. 880, 26 pages.
Guillaumot et al., "The *Arabidopsis* TSPO-related protein is a stress and abscisic acid-regulated, endoplasmic reticulum-Golgi-localized membrane protein", The Plant Journal, 2009, vol. 60, No. 2, pp. 242-256.
Selvaraj et al., "Current status and future perspectives: TSPO in steroid neuroendocrinology", Journal of Endocrinology, 2016, vol. 231, No. 1, pp. R1-R30.
Tu et al., "Translocator Protein (TSPO) Affects Mitochondrial Fatty Acid Oxidation in Steroidogenic Cells", Endocrinology, 2016, vol. 157, No. 3, pp. 1110-1121.
Li et al., "Translocator Protein 18kDa(TSPO): An Old Protein with New Functions?", Biochemistry, 2016, vol. 55, No. 20, pp. 2821-2831.
Haslam et al., "Synthetic redesign of plant lipid metabolism", The Plant Journal, 2016, vol. 87, No. 1, pp. 76-86.
International Preliminary Report on Patentability dated Feb. 25, 2020 in International (PCT) Application No. PCT/EP2018/072878.
Office Action dated Dec. 28, 2021 in corresponding Chinese Patent Application No. 201880055140.5, with English Translation, 22 pages.

(Continued)

*Primary Examiner* — Charles Logsdon
*Assistant Examiner* — Wayne Zhong
(74) *Attorney, Agent, or Firm* — Wenderoth, Lind & Ponack, L.L.P.

(57) ABSTRACT

The present invention relates generally to the field of plant molecular biology and relates to plants having a modified lipid metabolism and to methods for making such modified plants. In particular, the invention provides modified plants and parts thereof, including seeds, having an increased level of triacylglycerol (TAG), by means of a seed-specific expression in seed tissues during seed filling of a nucleic acid encoding a translocator protein (TSPO) in said modified plants or parts thereof. The invention further relates to methods for modulating lipid metabolism in plants and for producing plants with a modified lipid metabolism. The invention also provides constructs, vectors and host cells useful in the methods of the invention, and further relates to products obtained from the modified plants.

26 Claims, 4 Drawing Sheets

Specification includes a Sequence Listing.

(56) References Cited

OTHER PUBLICATIONS

Lin et al., "TSPO(outer membrane tryptophan-rich sensory protein)-like protein [*Arabidopsis thaliana*]", GeneBank Database, Accession No. NP_566110.1, 2017, 2 pages.
Marginedas-Freixa et al., "TSPO ligands stimulate ZnPPIX transport and ROS accumulation leading to the inhibition of *P. falciparum* growth in human blood", Scientific Reports, 2016, vol. 6; 33156, DOI: 10.1038/srep33516, pp. 1-15.

* cited by examiner

*MDSQDIRYRGGDDRDAATTAMAETERKSADDNKGKRDQKRAMAKRGLKS*LTVAVAAPVLVTLFATY
FLGTSDGYGNRAKSSSWIPPLWLL*H*TT*C*LASSGLMGLAAWLVWVDGGF*H*KKPNAL*YL Y*LAQFLLCLV
WDPVTFRVGSGVAGLAVWLGQSAALFGCYKAFNEISPVAGNLVKPCLAWAAFVAAVNVKLAVA

```
OsTSPO      MASAA-AAAAAAQEGITHRAVRGDGGDAAATAGGGEAASRDPRKAGRAKRGLRSLAAAVS
LuTSPO      MNTSG------------------------TNNISSTRDQGEKRMV-MAKRGLRSLAVALG
BnTSPO3     MDSQD-IRSRAGD-------AAMAETERKHASD-VNNKGKRDQKRA-MAKRGLKSLTLAVA
BnTSPO1     MDSQD-IRYRAGD-------AAMAETERKQADDNNNNKGKRDQKRA-MAKRGLKSLTLAVA
BrTSPO1     MDSQD-IRYRAGD-------AAMAETERKQADDNNNNKGKRDQKRA-MAKRGLKSLTLAVA
BnTSPO2     MDSQDTVRHRGGDERDAATTATAETDRKHADD--NNKGQRDQKRA-MAKRGLKSLTVAVA
BnTSPO4     MDSQD-IRHRGGDDRDAATTAMAETDRKQADD--NNKGQRDQKRA-MAKRGLKSLTVAVA
BrTSPO2     MDSQD-IRHRGGDDRDAATTAMAETDRKQADD--NNKGQRDQKRA-MAKRGLKSLTVAVA
AtTSPO      MDSQD-IRYRGGDDRDAATTAMAETERKSADD---NKGKRDQKRA-MAKRGLKSLTVAVA
CsTSPO      MDSQD-IRYRGGDDRDAATTAMAETERKHADD---NKGKLHQKRA-MAKRGLRSLTVAVA
            * :                           :       .  . . *****.**: *:.

OsTSPO      VSVALMAASFYGSGSASASASAA--------RVT--------VARAGSVAAEAVMALAAWM
LuTSPO      LPPSLTILSIYFLG-GGGYNSDDELLPVSSYKKPFWFPPSWVIHVFCVISTFLMGLSGWL
BnTSPO3     APVLLTLFASYFLG-------NRA--------RSSSWILPLWVLHLMRLASSGLMGLAAWL
BnTSPO1     APVLLTLFTSYFLG-------NQA--------RSSS-----WVLHLMRLASSGLMGLAAWL
BrTSPO1     APVLLTLFTSYFLG-------NQA--------RSSS-----WVLHLMRLASSGLMGLAAWL
BnTSPO2     APVLVMLFETYFLG---GYGSRA--------RSSSWIPPPWVLHVTRLASSGLMGLAAWL
BnTSPO4     APVLVMLFETYFLG-GGGYGSRA--------RSSSWIPPPWVLHATRLASSGLMGLAAWL
BrTSPO2     APVLVMLFETYFLG-GGGYGSRA--------RSSSWIPPPWVLHATRLASRGLMGLAAWL
AtTSPO      APVLVTLFATYFLGTSDGYGNRA--------KSSSWIPPLWLLHTTCLASSGLMGLAAWL
CsTSPO      APVLVTLFATFFLGTSDGYGNRA--------RSSSWIPPLWLLHTTCLASSCLMGLAAWL
              .  :   : *    .          . .    :  .   :::   :*.*:..*:

OsTSPO      VWAEGGLHRRPGATLAPFVAQLVAALAWAPLALGLAAPAAGLACCAAMAAGAAACARGFG
LuTSPO      VWAEGRFHNEPAT-LYIYGVQMGFNSILIPIVCGLNIPSLGLIISMCLLGALISCSRHFR
BnTSPO3     VWVDGGFHKKPNA-LYLYLAQFVLSL----TTCMVGSGLAGLAVCLGQSAALFGCYKAFN
BnTSPO1     VWVDAGFHKKPNA-LYLYLAQFVLCL----TTCMVGSGLAGLAVCLCQSAALFRCYKAFN
BrTSPO1     VWVDAGFHKKPNA-LYLYLAQFVLCL----TTCMVGSGLAGLAVCLCQSAALFGCYKAFN
BnTSPO2     VWVDGGFHKKPNA-LYLYLAQFTLCLLWGPVTFLVGSGLAGLVVWLGQSAALFGCYKAFN
BnTSPO4     VWVDGGFHKKPNA-LYLYLAQFTLCLLWGPVTFLVGSGLAGLVVWLGQSAALFGCYKAFN
BrTSPO2     VWVDGGFHKKPNA-LYLYLAQFTLCLLWGPVTFLVGSGVAGLVVWLGQSAALFGCYKAFN
AtTSPO      VWVDGGFHKKPNA-LYLYLAQFLLCLVWDPVTFRVGSGVAGLAVWLGQSAALFGCYKAFN
CsTSPO      VWVDGGFHKKPNA-LYLYLAQFLVCLLWDPVTFRLGSGIAGLAVWLGQSAALFGCFKAFS
            **.:. :*. * : *   : .*:         . :      **       .. * . *

OsTSPO      GVNPVAGDLAKPCVAWAVLLAVINYKMMN-
LuTSPO      ITNPIAADLVKPCIAWAAFLIILNLKLI--
BnTSPO3     ETSPVAGNMVKPCLAFAAFVAAVNVKLAIA
BnTSPO1     ETSPVAGNMVMPCLAFAAFVAAVNVKLAIA
BrTSPO1     EISPVAGNMVKPCLAFAAFVAAVNVKLAIA
BnTSPO2     EISPVAGNLVKPCLACTAFVAAVNVKLAIA
BnTSPO4     EISPVAGNLVKPCLACAAFVTAVNVKLAIA
BrTSPO2     EISPVAGNLVKPCLACAAFVTAVNVKLAIA
AtTSPO      EISPVAGNLVKPCLAWAAFVAAVNVKLAVA
CsTSPO      EISPVAGNLVKPCLAWAAFVAAVNVKLAIA
             .*:*.::. **:*  :..::   :* *:
```

FIGURE 4

PLANTS WITH MODIFIED LIPID METABOLISM AND METHODS FOR MAKING THE SAME

FIELD OF THE INVENTION

The present invention relates generally to the field of plant molecular biology and relates to plants having a modified lipid metabolism and to methods for making such plants. In particular, the invention is directed to plants and parts thereof, including seeds, having an increased level of triacylglycerol. The invention further relates to methods for making such plants. The present invention is based on the modulation of a particular seed-specific expression in such plants of a nucleic acid encoding a translocator protein (a TSPO polypeptide). The invention further provides constructs, vectors and host cells useful in the methods of the invention, and further relates to products obtained from the modified plants.

BACKGROUND OF THE INVENTION

Vegetable oils, i.e. oils of plant origin, have been predominantly used for food and feed-based applications. Such vegetable oils provide a wide diversity in fatty acids (FAs) compositions with diverse applications. In addition, plants can be engineered to produce fatty acids which are nutritionally beneficial to human or animal health. Vegetable oils therefore have the potential to provide an alternative source of nutritionally and medically important long chain polyunsaturated fatty acids or 'Fish oil'.

Besides being edible, vegetable oils are now also increasingly used in industrial applications such as paints, lubricants, soaps, biofuels, etc. Vegetable oils thus also have potential to be an alternative for non-renewable petroleum sources for industrial application, provided that their composition can be matched to end-use requirements, and that they can be produced on sufficient scale to meet current and growing industrial demands.

Most vegetable oils are derived from seeds of the plants, so-called seed oils. Seed oils comprise mostly neutral (storage) lipids and few polar (membrane) lipids. Storage lipids are mainly composed of glycerol esters of fatty acids (typically >90%), also known as triacylglycerol (TAG). These lipids are generally stored in a compartment specialized for lipid storage, the lipid body. This compartment is found in most oleaginous plant cells, and is used to store a variety of TAG molecules depending on the species. Triacylglycerol molecules primarily serve as carbon and energy reserves, which are used during germination and growth of the young seedling. In addition to TAGs, plants also contain membrane (polar) lipids which are mainly found in the various membranes of the seed cells, e.g. the endoplasmic reticulum and other endomembranes and the plasma membrane.

The lipid content and fatty acid composition of seed oils varies. Moreover, environmental changes or human manipulation, such as breeding or genetic engineering have been used to change lipid content and composition of the seed oils. Nevertheless, although the lipid and fatty acid content and/or composition of seed oil can to some extent be modified by traditional methods of plant breeding, such methods are usually laborious to develop new desirous breeds. Conventional breeding with crossing for instance comprises very laborious and time-consuming processes which aim at the selection of desired breeds from various variants and establishment of pure lines. Other methods, such as γ-ray irradiation and somaclonal variation, have been conducted in an attempt of obtaining desired breeds from various variants. However, breeds obtained by these methods often cannot be used for cultivation because, in addition to targeted genes, other genes in these breeds are often mutated simultaneously.

On the contrary, the advent of recombinant DNA technology has allowed for easier manipulation of the seed oil content of a plant. Recent advances in understanding of the basic biochemistry of seed oil biosynthesis, coupled with cloning of genes encoding the enzymes involved in fatty acid modification and oil accumulation, have created possibilities for the metabolic engineering of crops that produce "designer" plant seed oils. In some approaches, key enzymatic steps are targets for gene modification, and strategies of metabolic engineering of fatty acids in oilseeds may include the overexpression and/or suppression of multiple genes encoding multi-step biosynthetic pathways, and/or assembling the complete pathway for the synthesis of long-chain polyunsaturated fatty acids. However, such approaches are complex, combining for instance heterologous genes expression, silencing of endogenous genes, specific culture conditions, etc. resulting in some cases penalties in plant growth and in yield.

In view hereof, there remains a need in the art to further modify and/or improve quantitatively and qualitatively the oil content of plants and to specifically identify genes and engineering approaches which have the capacity to confer altered or increased oil production to its host plant and to other plant species. Thus, the technical problem underlying the present invention may be seen as the provision of means and methods for complying with the aforementioned needs.

SUMMARY OF THE INVENTION

It has now been found that lipid metabolism may be modified and improved in plants by modulating the expression in such plant of a nucleic acid encoding a translocator polypeptide (TSPO polypeptide). In particular, through extensive research, the present inventors have found that modulating the expression of a nucleic acid encoding a translocator polypeptide (TSPO polypeptide) in a plant, plant part or plant cell, confers a modified, and in particular an improved lipid metabolism to said plant, plant part or plant cell as compared to a control plant, plant part or plant cell. Modulated expression of said nucleic acid in accordance with the present invention involves a particular and well defined seed-specific expression of said nucleic acid. The improved characteristics conferred by such defined seed-specific expression comprise inter alia an overall increased level of triacylglycerol (TAG) in the modified plants as compared to non-modified plants.

Therefore, in a first aspect, the present invention relates to a plant, a plant part, including seeds, or a plant cell comprising a construct, wherein said construct comprises the following operably linked nucleic acid sequences: a) a promoter sequence, b) a nucleic acid encoding a TSPO polypeptide, and optionally c) a transcription terminator sequence, wherein said promoter sequence is a seed-specific promoter which is active in seed tissues during seed filling; and wherein said construct confers a modified lipid metabolism to said plant, plant part or plant cell, as compared to a control plant, plant part or plant cell.

In certain embodiments, the present invention relates to a plant, a plant part, including seeds, or a plant cell comprising a construct, wherein said construct comprises the following operably linked nucleic acid sequences:
 a) a promoter sequence,
 b) a nucleic acid encoding a TSPO polypeptide, and optionally c) a transcription terminator sequence, wherein said promoter sequence is a seed-specific promoter which is active in seed tissues during seed filling.

In preferred embodiments, said nucleic acid encoding a TSPO polypeptide is of plant origin.

In certain embodiments, said nucleic acid encoding a TSPO polypeptide is a nucleic acid that encodes a TSPO polypeptide represented by SEQ ID NO: 2, or a homologue thereof, said homologue having at least 25% sequence identity to said TSPO.

In another aspect there is provided a construct comprising the following operably linked nucleic acid sequences:
a) a nucleic acid encoding a TSPO polypeptide, and preferably a TSPO polypeptide as defined herein,
b) one or more control sequences capable of driving expression of the nucleic acid of a); and optionally
c) one or more transcription terminator sequences,
wherein at least one of said control sequences is a seed-specific promoter which is active in seed tissues during seed filling, preferably a seed-specific promoter as defined herein.

In another aspect, the invention also provides for use of a construct as taught herein in a method for making plants having a modified lipid metabolism, and preferably for making plants having an enhanced amount of triacylglycerol as compared to control plants.

In another aspect, the present invention also provides a plant, plant part or plant cell transformed with a construct as defined herein.

In another aspect, the invention relates to a method for modifying the lipid metabolism in a plant as compared to a control plant comprising the step of providing a plant comprising a construct, wherein said construct comprises the following operably linked nucleic acid sequences: a) a promoter sequence, b) a nucleic acid encoding a TSPO polypeptide, and preferably a TSPO polypeptide as defined herein, and optionally c) a transcription terminator sequence, wherein said promoter sequence is a seed-specific promoter which is active in seed tissues during seed filling, preferably a seed-specific promoter as defined herein.

In yet another aspect, a method is provided for the production of a plant having a modified lipid metabolism as compared to a control plant, which method comprises the steps of:
i) Introducing and expressing in said plant or a cell thereof a construct, wherein said construct comprises the following operably linked nucleic acid sequences: a) a promoter sequence, b) a nucleic acid encoding a TSPO polypeptide, and preferably a TSPO polypeptide as defined herein, and optionally c) a transcription terminator sequence, wherein said promoter sequence is a seed-specific promoter which is active in seed tissues during seed filling, preferably a seed-specific promoter as defined herein, and
ii) Cultivating said plant cell or said plant under conditions promoting plant growth and development.

The present invention further provides a plant obtainable by a method as defined herein, or a plant part thereof, including a harvestable part thereof such as seeds, or a plant cell thereof.

Thus, provided herein are modified plants or parts thereof such as seeds having increased triacylglycerol (TAG) production and TAG levels as compared to non-modified plants or parts thereof, as well as methods and tools such as constructs for their production. Modified plants according to the invention produce higher amounts of triacylglycerols, as a result of the engineered expression of a TSPO polynucleotide encoding a TSPO polypeptide in a defined seed-specific manner.

It is unexpected that a seed-specific expression of a TSPO polynucleotide, and particularly in seed tissues during a seed developmental stage, may have a beneficial impact on the lipid metabolism of the plants. Such finding is unanticipated, especially in view of the different endogenous expression pattern of a native TSPO polynucleotide, according to which such TSPO is induced under environmental abiotic stress conditions in plants (e.g. salt or osmotic stress). It is in general known in the art that TSPO is a protein that can be found in eukaryotic as well as prokaryotic species. It is further known that TSPOs of plant origin share low homology with animal and bacterial TSPOs and are structurally different from bacterial and animal TSPOs, which may translate in functional differences as well between these TSPOs of different origins.

It has now been shown that a seed-specific expression of a TSPO polynucleotide in plants permits to modulate lipid metabolism in plants, and in particular permits to increase the amount of TAG produced by the plant, without compromising plant growth, plant development, and plant yield. Under natural conditions, TSPO is known to be a stress-induced membrane protein and to be involved in stress homeostasis. TSPO from *Arabidopsis thaliana* for instance is known to be transiently induced by abiotic stress such as osmotic stress or by the stress phytohormone abscisic acid. An effect of TSPO, when induced in a well-defined seed-specific manner on lipid metabolism, and in particular on the increase in TAG levels, is therefore surprising and unpredictable.

Additional methods are disclosed herein for producing products having enhanced levels of TAG. To that end, in another aspect, a method for producing a product, such as an oil or fat, in a plant is provided, which method comprises the steps of growing a (modified) plant as defined herein and producing or collecting said product from or by said plant or part thereof, including seeds.

In another aspect, also a product, such as an oil or fat, is provided herein, which product is produced from or by a plant, or part thereof, including seeds, as defined herein, or such product is obtainable by a method as defined herein. The present invention will now be further described. In the following passages, different aspects of the invention are defined in more detail. Each aspect so defined may be combined with any other aspect or aspects unless clearly indicated to the contrary. In particular, any feature indicated as being preferred or advantageous may be combined with any other feature or features indicated as being preferred or advantageous.

BRIEF DESCRIPTION OF THE FIGURES

FIG. 4 represents a multiple alignment of various TSPO polypeptides using MUSCLE-ClustalW. These alignments can be used for defining motifs or consensus sequences, when using conserved amino acids, i.e. those identical in the aligned sequences and/or those highly conserved. Reference is made to Example 2 for details.

DETAILED DESCRIPTION OF THE INVENTION

Figure 1:
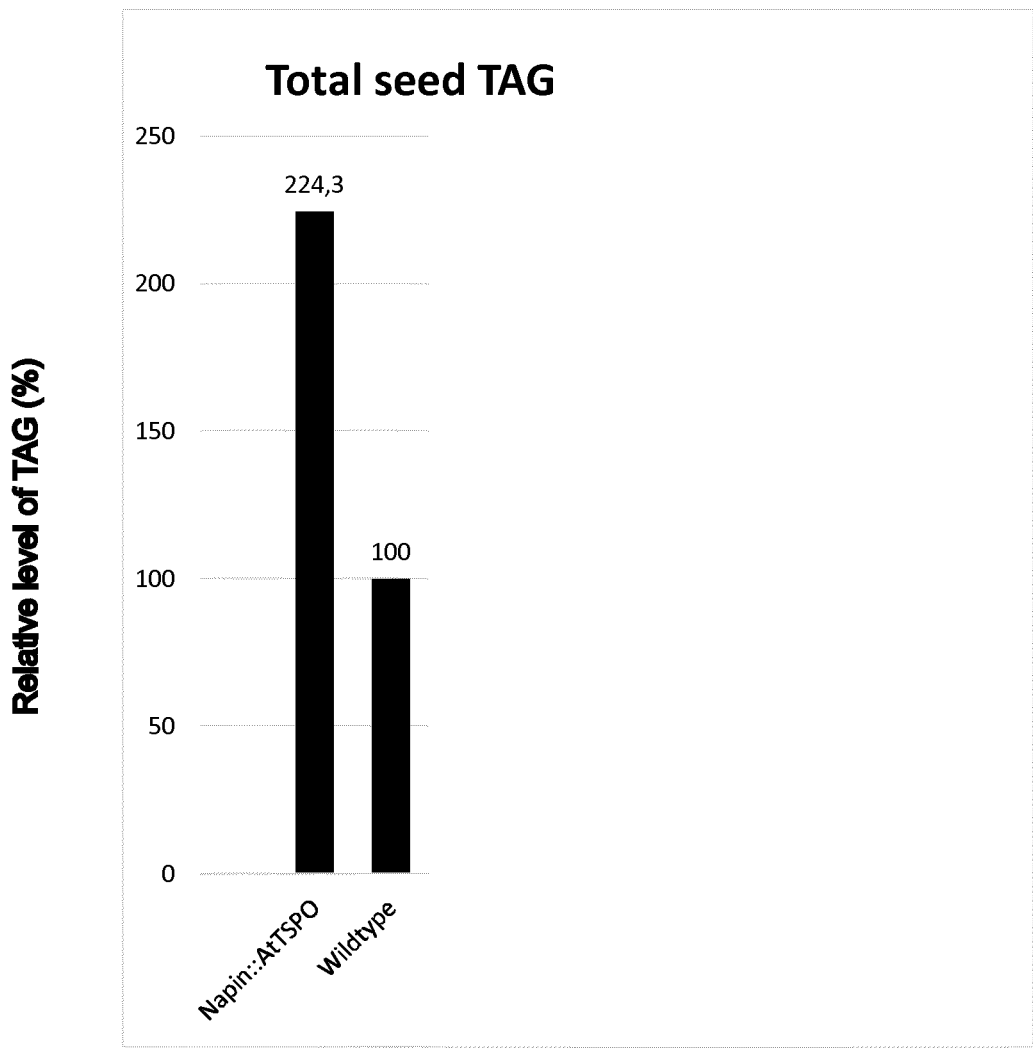
FIG. 1 illustrates TAG levels as measured in transgenic *Arabidopsis* dry seeds expressing an *Arabidopsis* TSPO gene under control of a seed-specific napin promoter (Napin::TSPO) from the napA gene of *Brassica napus*, and as compared to TAG level as determined in wild type *Arabidopsis* dry seeds (wildtype).

Unless otherwise defined, all terms used in disclosing the invention, including technical and scientific terms, have the meaning as commonly understood by one of ordinary skill in the art to which this invention belongs. By means of further guidance, term definitions are included to better appreciate the teaching of the present invention.

As used herein, the singular forms "a", "an", and "the" include both singular and plural referents unless the context clearly dictates otherwise.

The terms "comprising", "comprises" and "comprised of" as used herein are synonymous with "including", "includes" or "containing", "contains", and are inclusive or open-ended and do not exclude additional, non-recited members, elements or method steps. The terms also encompass "consisting of" and "consisting essentially of", which enjoy well-established meanings in patent terminology.

The recitation of numerical ranges by endpoints includes all numbers and fractions subsumed within the respective ranges, as well as the recited endpoints.

The term "about" or "approximately" as used herein when referring to a measurable value such as a parameter, an amount, a temporal duration, and the like, is meant to encompass variations of +/−10% or less, preferably +/−5% or less, more preferably +/−1% or less, and still more preferably +/−0.1% or less of and from the specified value, insofar such variations are appropriate to perform in the disclosed invention. It is to be understood that the value to which the modifier "about" or "approximately" refers is itself also specifically, and preferably, disclosed.

Whereas the terms "one or more" or "at least one", such as one or more or at least one member(s) of a group of members, is clear per se, by means of further exemplification, the term encompasses inter alia a reference to any one of said members, or to any two or more of said members, such as, e.g., any $\geq 3$, $\geq 4$, $\geq 5$, $\geq 6$ or $\geq 7$ etc. of said members, and up to all said members.

Reference throughout this specification to "one embodiment" or "an embodiment" means that a particular feature, structure or characteristic described in connection with the embodiment is included in at least one embodiment of the present invention. Thus, appearances of the phrases "in one embodiment" or "in an embodiment" in various places throughout this specification are not necessarily all referring to the same embodiment, but may. Furthermore, the particular features, structures or characteristics may be combined in any suitable manner, as would be apparent to a person skilled in the art from this disclosure, in one or more embodiments. Furthermore, while some embodiments described herein include some but not other features included in other embodiments, combinations of features of different embodiments are meant to be within the scope of the invention, and form different embodiments, as would be understood by those in the art. For example, in the appended claims, any of the claimed embodiments can be used in any combination.

All references cited in the present specification are hereby incorporated by reference in their entirety. In particular, the teachings of all references herein specifically referred to are incorporated by reference.

In the following passages, preferred statements (features) and embodiments of the constructs, plants, method, products and uses of the invention, are set herein below. Each statement and embodiment of the invention so defined may be combined with any other statement and/or embodiment, unless clearly indicated to the contrary. In particular, any feature indicated as being preferred or advantageous may be combined with any other features or statements indicated as being preferred or advantageous.

Hereto, the present invention is in particular captured by any one or any combination of one or more of the below numbered aspects and embodiments, with any other statement and/or embodiment.

Statements

1. A plant, a plant part, including seeds, or a plant cell comprising a construct, wherein said construct comprises the following operably linked nucleic acid sequences:
   a) a promoter sequence,
   b) a nucleic acid encoding a TSPO polypeptide, and optionally
   c) a transcription terminator sequence,
   wherein said promoter sequence is a seed-specific promoter, preferably a seed-specific promoter which is active in seed tissues during seed filling; and
   wherein said construct confers a modified lipid metabolism to said plant, plant part or plant cell, as compared to a control plant, plant part or plant cell.

2. A plant, a plant part, including seeds, or a plant cell comprising a construct, wherein said construct comprises the following operably linked nucleic acid sequences:
   a) a promoter sequence,
   b) a nucleic acid encoding a TSPO polypeptide, and optionally
   c) a transcription terminator sequence,
   and wherein said promoter sequence is a seed-specific promoter, preferably a seed-specific promoter which is active in seed tissues during seed filling.

3. The plant, a plant part, or a plant cell according to statement 1 or 2, wherein said promoter sequence is not a naturally occurring TSPO promoter.

4. The plant, a plant part, including seeds, or a plant cell according to any of statements 1 to 3, having said construct introduced and expressed in said plant, plant part, or a plant cell.

5. The plant, plant part, or plant cell according to any of statements 1 to 4, wherein said nucleic acid encodes a TSPO polypeptide comprising
   a. a tryptophan-rich sensory protein/peripheral-type benzodiazepine receptor domain (TspO/MBR domain) having at least 30% sequence identity to the TspO/MBR domain as represented by SEQ ID NO: 49 and/or
   b. a N-terminal domain having at least 30% sequence identity to the N-terminal domain as represented by SEQ ID NO: 50.
   c. a conserved domain having at least 70% sequence identity to the sequence as represented by SEQ ID NO: 51.
6. The plant, plant part, or plant cell according to any of statements 1 to 5, wherein said nucleic acid encodes a TSPO polypeptide comprising a N-terminal domain having at least 30% sequence identity, and for instance at least 50%, 75%, 80%, 85%, 90%, 95%, 96%, 97%, 98%, or 99% overall sequence identity to the N-terminal domain as represented by SEQ ID NO: 50.
7. The plant, plant part, or plant cell according to any of statements 1 to 6, wherein said nucleic acid encodes a TSPO polypeptide represented by SEQ ID NO: 2, or a homologue thereof, said homologue having at least 25% sequence identity to said TSPO polypeptide, or said homologue having in increasing order of preference at least 30%, 35%, 40%, 45%, 50%, 55%, 60%, 65%, 70%, 75%, 80%, 85%, 86%, 87%, 88%, 89%, 90%, 91%, 92%, 93%, 94%, 95%, 96%, 97%, 98%, 99% or 100% overall sequence identity to the amino acid represented by SEQ ID NO: 2.
8. The plant, plant part, or plant cell according to any of statements 1 to 7, wherein said nucleic acid encodes a TSPO polypeptide represented by SEQ ID NO: 2 or a homologue thereof having at least 25%, preferably at least 30%, preferably at least 50%, preferably at least 75%, preferably at least 80%, preferably at least 85%, preferably at least 90% overall sequence identity to SEQ ID NO: 2.
9. The plant, plant part, or plant cell according to any of statements 1 to 7, wherein said nucleic acid encodes a TSPO polypeptide represented by SEQ ID NO: 32 or a homologue thereof having at least 25%, preferably at least 30%, preferably at least 50%, preferably at least 75%, preferably at least 80%, preferably at least 85%, preferably at least 90% overall sequence identity to SEQ ID NO: 32.
10. The plant, plant part, or plant cell according to any of statements 1 to 7, wherein said nucleic acid encodes a TSPO polypeptide represented by SEQ ID NO: 34 or a homologue thereof having at least 25%, preferably at least 30%, preferably at least 50%, preferably at least 75%, preferably at least 80%, preferably at least 85%, preferably at least 90% overall sequence identity to SEQ ID NO: 34.
11. The plant, plant part, or plant cell according to any of statements 1 to 10, wherein said TSPO polypeptide is represented by any one of the TSPO polypeptides of TABLE 1.
12. The plant, plant part, or plant cell according to any of statements 1 to 11, wherein said nucleic acid encodes a modified TSPO polypeptide, wherein said modified TSPO polypeptide comprises one or more amino acid sequence changes compared to the amino acid sequence of the corresponding non-modified TSPO polypeptide.
13. The plant, plant part, or plant cell according to any of statements 1 to 12, wherein said nucleic acid encoding a TSPO polypeptide is of plant origin, and preferably is endogenous to said plant.
14. The plant, plant part, or plant cell according to any of statements 1 to 13 wherein said nucleic acid encoding a TSPO polypeptide is represented by any one of the TSPO nucleic acids of TABLE 1 or any variant thereof.
15. The plant or part thereof, or plant cell according to any of statements 1 to 14, wherein said seed-specific promoter is a promoter which is active during the period of lipid biosynthesis during said seed filling.
16. The plant or part thereof, or plant cell according to any of statements 1 to 15, wherein said seed-specific promoter is a promoter of gene encoding a seed storage protein.
17. The plant or part thereof, or plant cell according to any of statements 1 to 16, wherein said seed-specific promoter is not a TSPO promoter.
18. The plant or part thereof, or plant cell according to any of statements 1 to 17, wherein said seed-specific promoter is a napin promoter, preferably a napin promoter from *Brassica napus*, preferably a promoter having a polynucleotide sequence having at least 90% sequence identity to SEQ ID NO: 43 or a functional fragment or homologue thereof.
19. The plant or part thereof, or plant cell according to any of statements 1 to 15 and 17, wherein said seed-specific promoter is a FAE1 promoter, preferably a FAE1 promoter from *Arabidopsis thaliana*, preferably a FAE1 promoter having a polynucleotide sequence having at least 90% sequence identity to SEQ ID NO: 44 or a functional fragment or homologue thereof.
20. The plant or part thereof, or plant cell according to any of statements 1 to 19, wherein said seed-specific promoter is exogenous to said plant.
21. The plant or part thereof, or plant cell according to any of statements 1 to 19, wherein said seed-specific promoter is endogenous to said plant.
22. The plant or part thereof, or plant cell according to any of statements 1 to 14 or 20 to 21, wherein said seed-specific promoter corresponds to a TSPO promoter that has been modified in order to confer seed-specific expression in seed tissues during seed filling, and preferably during the period of lipid biosynthesis during said seed filling.
23. The plant, plant part, or plant cell according to any of statements 1 and 3 to 22, wherein said modified lipid metabolism comprises an enhanced amount of triacylglycerol in said plant, plant part or plant cell as compared to a control plant, plant part or plant cell.
24. The plant, plant part, or plant cell according to any of statements 1 to 23, wherein said plant, plant part, or plant cell comprises an enhanced amount of triacylglycerol in said plant, plant part or plant cell as compared to a control plant, plant part or plant cell.
25. The plant, plant part, or plant cell according to statement 23 or 24, wherein said triacylglycerol is an ester derived from glycerol and fatty acids, wherein said fatty acids are selected from the group comprising long chain fatty acids (LCFA) comprising 13 to 18 carbon atoms and very long chain fatty acids (VLCFA) comprising more than 18 carbon atoms.
26. Construct comprising the following operably linked nucleic acid sequences:
   a) a nucleic acid encoding a TSPO polypeptide, and preferably a TSPO polypeptide as defined in any of statements 1 to 2 and 5 to 11, or a nucleic acid as defined in any of statements 12 to14;
b) one or more control sequences capable of driving expression of the nucleic acid of a); and optionally
c) one or more transcription terminator sequences, wherein at least one of said control sequences is a seed-specific promoter, preferably which is active in seed tissues during seed filling; and/or preferably which is as defined in any one of statements 1-3 and 15 to 22.

27. Use of a construct according to statement 26 in a method for making plants having a modified lipid metabolism, and preferably in a method for making plants having an enhanced amount of triacylglycerol as compared to control plants.

28. Use according to statement 27, wherein said modified lipid metabolism is as defined in any of statements 23 to 25.

29. Vector comprising a construct according to statement 26.

30. Host cell, such as a bacterial cell, comprising a construct according to statement 26.

31. Host cell, such as a bacterial cell, transformed with a construct according to statement 26.

32. Plant, plant part or plant cell transformed with a construct according to statement 26.

33. Plant, plant part, or plant cell according to any of statements 1 to 25 and 32, wherein said plant is a plant capable of producing an oil (edible or non-edible), and preferably is a plant selected from the group comprising canola, oilseed rape (*Brassica napus*), turnip rape (*Brassica rapa*), Camelina (*Camelina sativa*), sesame, soybean, maize, sunflower, safflower, rice, linseed (flaxseed), cotton, mustard, castor beans (*Ricinus communis*) and peanuts.

34. Method for modifying the lipid metabolism in a plant as compared to a control plant comprising the step of providing a plant comprising a construct, wherein said construct comprises the following operably linked nucleic acid sequences: a) a promoter sequence, b) a nucleic acid encoding a TSPO polypeptide, and c) optionally a transcription terminator sequence, wherein said promoter sequence is a seed-specific promoter, preferably which is active in seed tissues during seed filling.

35. Method for enhancing the amount of triacylglycerol in a plant as compared to a control plant, comprising the step of providing a plant comprising a construct, wherein said construct comprises the following operably linked nucleic acid sequences: a) a promoter sequence, b) a nucleic acid encoding a TSPO polypeptide, and c) optionally a transcription terminator sequence, wherein said promoter sequence is a seed-specific promoter, preferably which is active in seed tissues during seed filling.

36. Method according to statement 34 or 35, wherein said nucleic acid encoding a TSPO polypeptide is as defined in any of statements 12 to 14 and/or wherein said TSPO polypeptide is as defined in any of statements 1 to 2 and 5 to 11.

37. Method according to any of statements 34 to 36, wherein said seed-specific promoter is as defined in any of statements 1 to 3 and 15 to 22.

38. Method according to any of statements 34 and 36 to 37, wherein said modified lipid metabolism is as defined in any of statements 23 to 25.

39. Method according to any of statements 34 to 38, wherein said plant is a plant capable of producing an oil (edible or non-edible), and preferably is a plant selected from the group comprising canola, oilseed rape, turnip rape, Camelina (*Camelina sativa*), sesame, soybean, maize, sunflower, safflower, rice, linseed, cotton, mustard, castor beans (*Ricinus communis*) and peanuts.

40. Plant obtainable by the method of any of statements 34 to 39, or a plant part thereof, including a harvestable part thereof such as seeds, or a plant cell thereof.

41. Plant according to statement 40 having an enhanced amount of triacylglycerol as compared to a control plant.

42. Method for the production of a plant having a modified lipid metabolism as compared to a control plant, which method comprises the steps of:
i) Introducing and expressing in said plant or a cell thereof a construct, wherein said construct comprises the following operably linked nucleic acid sequences: a) a promoter sequence, b) a nucleic acid encoding a TSPO polypeptide, and c) optionally a transcription terminator sequence, wherein said promoter sequence is a seed-specific promoter, preferably which is active in seed tissues during seed filling, and
ii) Cultivating said plant cell or said plant under conditions promoting plant growth and development.

43. Method for the production of a plant having an enhanced amount of triacylglycerol as compared to a control plant, which method comprises the steps of:
iii) Introducing and expressing in said plant or a cell thereof a construct, wherein said construct comprises the following operably linked nucleic acid sequences: a) a promoter sequence, b) a nucleic acid encoding a TSPO polypeptide, and c) optionally a transcription terminator sequence, wherein said promoter sequence is a seed-specific promoter, preferably which is active in seed tissues during seed filling, and
iv) Cultivating said plant cell or said plant under conditions promoting plant growth and development.

44. Method according to statement 42 or 43, wherein said nucleic acid encoding a TSPO polypeptide is as defined in any of statements 12 to 14 and/or wherein said TSPO polypeptide is as defined in any of statements 1 to 2 and 5 to 11.

45. Method according to any of statements 42 to 44, wherein said seed-specific promoter is as defined in any of statements 1 to 3 and 15 to 22.

46. Method according to any of statements 42 and 44 to 45, wherein said modified lipid metabolism is as defined in any of statements 23 to 25.

47. Method according to any of statement 42 to 46, wherein said plant is a plant capable of producing an oil (edible or non-edible), and preferably a plant selected from the group comprising canola, oilseed rape, turnip rape, Camelina (*Camelina sativa*), sesame, soybean, maize, sunflower, safflower, rice, linseed, cotton, mustard, castor beans (*Ricinus communis*) and peanuts.

48. Plant obtainable by the method of any of statements 42 to 47, or a plant part thereof, including a harvestable part thereof such as seeds, or a plant cell thereof.

49. Plant according to statement 48 having an enhanced amount of triacylglycerol as compared to a control plant.

50. A method for producing a product, such as an oil or fat, in a plant comprising the steps of growing a plant according to any of statements 1 to 25, 32-33, 40-41, and 48-49, and producing said product from or by said plant or part thereof, including seeds.

51. A product, such as an oil or fat, produced from or by a plant, or part thereof, including seeds, according to any one of statements 1 to 25, 32-33, 40-41, and 48-49 or product obtainable by the method of statement 50.

52. A product according to statement 51, having an enhanced amount of triacylglycerol as compared to a control product produced from or by a control plant, or part thereof.

The present application is directed to genetic engineering of plants using techniques working primarily through the purposeful insertion and/or modification of nucleic and/or amino acid sequences in a plant.

The present inventors have found by extensive experimentation that the expression of a nucleic acid encoding a translocator protein (TSPO) in a plant in a seed-specific manner, i.e. during seed development, and particularly during the stage of seed filling (storage compound biosynthesis), permits to modify lipid metabolism in the plant. It has thus been found that a non-constitutive expression of a nucleic acid encoding a TSPO influences, and in particular improves lipid metabolism in a plant. In particular, the inventors have shown that seed-specific expression as provided herein of a nucleic acid encoding a TSPO is capable of conferring improved lipid metabolism to a plant, when compared to a control plant in which the nucleic acid encoding a TSPO is either not expressed or is endogenously expressed but not in a seed-specific manner as defined herein. More particularly, a non-constitutive expression, and in particular a seed-specific expression as defined herein of a nucleic acid encoding a TSPO is capable of increasing the amount of triacylglycerol molecules (herein "TAG") in a plant as compared to a control plant. Hence, seed-specific expression of a nucleic acid encoding a TSPO in a plant permits to quantitatively and qualitatively improve lipid metabolism of the plant, and to produce plants having quantitative and qualitative improved lipids, in particular triacylglycerol production.

In certain embodiments, specific types of triacylglycerol molecules may be qualitatively and quantitatively altered. These findings are unexpected, especially since the nucleic acid encoding a TSPO has previously been associated to different plant physiological mechanisms and different plant pathways, in particular plant nucleic acids encoding a TSPO were previously reported to be associated to abiotic stress regulation in plants.

The present invention is thus directed to a modulation of the expression of a nucleic acid encoding a translocator protein.

The term "expression" or "expression of a nucleic acid" or "gene expression" means the transcription of a specific gene or specific genes or specific construct. The term "expression" or "gene expression" in particular means the transcription of a gene or genes or construct into structural RNA (rRNA, tRNA) or mRNA with or without subsequent translation of the latter into a protein. The process includes transcription of DNA and processing of the resulting mRNA product. The term "modulated expression" as used herein means any form of expression that is different from the original wild-type expression level and/or pattern.

A "translocator protein" as applied in the present invention refers to a protein that belongs to the family of proteins containing a tryptophan-rich sensory protein/peripheral-type benzodiazepine receptor (TspO/MBR) domain. This family of translocator protein (TSPO)/peripheral-type benzodiazepine receptor (MBR) domain-containing proteins are membrane-anchored proteins that appear to be highly conserved from bacteria to mammals. Translocator proteins were also identified in plants, wherein they were previously reported to have physiological functions in the adaptation to adverse environmental conditions, such as osmotic and salt stress. For instance, the *Arabidopsis* translocator protein (AtTSPO) is a polytopic membrane protein that is encoded by a single locus in *Arabidopsis*. AtTSPO is a multi-stress regulator and the level of AtTSPO is tightly regulated in plant cells. AtTSPO in only transiently expressed in *Arabidopsis* during stress, and constitutively expressed AtTSPO is known to be actively downregulated through a selective autophagy pathway. AtTSPO targeting to this autophagy pathway requires heme binding (Vanhee et al., 2011, The Plant Cell: 23, 785-805; Hachez et al., 2014, The Plant Cell: 26, 4974-4990).

Various embodiments of nucleic acids encoding translocator proteins as applied in the present invention are further elaborated below.

In one aspect, the present invention relates to a construct comprising the following operably linked nucleic acid sequences:
 a) a nucleic acid encoding a TSPO polypeptide as defined herein,
 b) one or more control sequences capable of driving expression of the nucleic acid of a); and optionally
 c) one or more transcription terminator sequences,
wherein at least one of said control sequences is a seed-specific promoter which is active in seed tissues during seed filling as defined herein.

A construct as taught herein is in particular characterised in that it contains a promoter sequence which is a seed-specific promoter active in seed tissue and during seed filling for driving the expression of the nucleic acid encoding a TSPO polypeptide. When introduced and expressed in a plant, plant part or plant cell, such construct confers a modified lipid metabolism as defined herein to said plant, plant part or plant cell, as compared to a control plant, plant part or plant cell lacking said construct. In the context of the present invention, a promoter sequence, a nucleic acid encoding a TSPO polypeptide, and optionally a transcription terminator sequence are thus operably linked to provide a construct of the invention. The expression "operably linked nucleic acid sequences" means that the nucleic acid sequences are linked to one another in such a way that expression control sequences, such as a promoter and transcription terminator, effectively control expression of a coding sequence of interest, such as the TSPO polynucleotide as defined herein.

The present invention further relates to the use of said construct in plants, plant parts including seeds and plant cells, vectors, host cells and methods of the invention for modifying lipid metabolism in targeted plants.

The different elements of a construct as taught herein will now first be described in more detail hereunder.

Promoter

The terms "promoter", "regulatory element", and "control sequence" are all used interchangeably herein and are to be taken in a broad context to refer to regulatory nucleic acid sequences capable of effecting expression of the sequences to which they are ligated. The term "promoter" typically refers to a nucleic acid control sequence (DNA sequence) located upstream from the transcriptional start of a gene or nucleic acid and which is involved in recognizing and binding of RNA polymerase and other proteins, thereby directing transcription of an operably linked nucleic acid. Thus, a promoter contains a DNA sequence that either is bound directly by, or is involved in the recruitment of, RNA polymerase. Encompassed by the term "promoter" are transcriptional regulatory sequences derived from a classical eukaryotic genomic gene (including the TATA box which may be required for accurate transcription initiation, with or without a CCAAT box sequence) and additional regulatory elements (i.e. upstream activating sequences, enhancers and silencers) which alter gene expression in response to certain stimuli, or in a tissue-specific manner. For instance, a promoter sequence can also include "enhancer regions", which are one or more regions of DNA that can be bound with proteins (namely the trans-acting factors) to enhance transcription levels of genes in a gene-cluster. The enhancer, while typically at the 5' end of a coding sequence, can also be separate from a promoter sequence, e.g., can be within an intron of a gene. The promoter sequence may comprise the 5' UTR and/or one or more introns (optionally located within in the 5' UTR).

Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ.

In accordance with the present invention, the promoter sequence applied in the plants, constructs and methods as taught herein is a "seed-specific" promoter.

The term "seed-specific" as used herein refers to a promoter that is active in seed tissues during seed filling. In other words, the seed-specific promoter as used herein has a specific spatial (in seed tissues) and time-dependent (during seed filling) expression pattern.

The term "seed tissues" as used herein is to be considered in its broadest sense and thus including endosperm, aleuron, and embryo tissues.

In certain embodiments, the seed-specific promoter is active essentially in seed tissues, and more preferably is active only in seed tissues. The term "essentially" in this context may refer to a promoter not being active in other tissues than seed tissues or having an activity in other tissues than seed tissues which is insignificant.

In certain embodiments, the seed-specific promoter as used in the present invention has no or insignificant activity in green tissues.

The term "seed filling" or "seed filling stage" as used herein refers to the stage during seed development in which storage compounds such as starch, lipids (oils), and proteins are biosynthesized and stored in seed tissues. In certain embodiments, "seed filling" or "seed filling stage" refers to the period (or stage) of lipid (oil) biosynthesis during said seed filling stage.

Seed development may be typically represented in three subsequence stages corresponding to: (a) embryogenesis, (b) seed filling, and (c) desiccation, resulting in the formation of a dry mature seed. Hence, the seed filling stage is preceded by embryogenesis stage, and followed by a desiccation and maturation of the seed. After maturation a dry seed is obtained which is ready to undergo germination under suitable conditions. During the seed filling stage, plants accumulate various types of storage compounds in their seed to allow the embryo to germinate and establish itself as a seedling. Depending upon the species, the main storage compounds can be starch, proteins, or lipids (oils). During the seed filling stage, the embryo usually enlarges to accommodate the deposition of storage compounds which are required for germination later on.

In certain embodiments, the seed-specific promoter is active essentially during seed filling, and preferably is active only during seed filling. The term "essentially" in this context may refer to a promoter not being active during other stages of seed development or to a promoter having an activity during other stages of seed development which is insignificant.

In certain embodiments, the seed-specific promoter is active essentially during the period of lipid (oil) biosynthesis during said seed filling, and preferably is active only during period of lipid (oil) biosynthesis during said seed filling.

In certain embodiments, the seed-specific promoter has no or insignificant activity during germination or during growth stages following germination.

In certain embodiments of the constructs, plants, or methods as taught herein, a seed-specific promoter as described herein is a promoter sequence of plant origin. A "promoter of plant origin" comprises regulatory elements, which mediate the expression of a coding sequence in plant cells and which originates from a plant cell.

In certain embodiments, a seed-specific promoter as described herein may originate or may be derived from a monocotyledonous plant, and preferably from a monocotyledonous plant selected from the group comprising rice, oil palm, wheat, maize, barley, sorghum, and Brachypodium dystachyon.

In certain other embodiments, a seed-specific promoter as described herein may originate or may be derived from a dicotyledonous plant, preferably from a dicotyledonous plant selected from the group comprising *Arabidopsis*, canola, oilseed rape, linseed (also named "flaxseed"), soybean, sunflower, cotton, peanut, sesame, castor beans (*Ricinus communis*).

In certain embodiments of the constructs, plants, or methods as taught herein, a seed-specific promoter as applied herein may be a promoter sequence from a gene which is exogenous to said plant, herein referred to as "exogenous promoter". In other words, said seed-specific promoter is exogenous to said plant, i.e. not originating from within that plant.

For example, the plant may be rapeseed (*Brassica napus*), and the promoter sequence may be a seed-specific promoter from *Arabidopsis*; or the plant may be linseed (*Linum usitatissimum*), and the seed-specific promoter may be a seed-specific promoter sequence from *Brassica napus*.

In certain other embodiments of the constructs, plants, or methods as taught herein, the seed-specific promoter may be a promoter sequence from a gene which is endogenous to said plant, herein referred to as "endogenous promoter". In other words, said seed-specific promoter is endogenous to said plant, i.e. originating from within that plant. For example, the plant may be rapeseed (*Brassica napus*), and the seed-specific promoter may be a seed-specific promoter from rapeseed; or the plant may be linseed *Linum usitatissimum*), and the seed-specific promoter may be a seed-specific promoter from linseed.

The term "exogenous" in the context of nucleic acid sequences (nucleic acid or amino acid sequences) as used herein refers to a foreign sequence, i.e., not naturally found in the given plant of interest; while the term "endogenous" refers to a sequence that is naturally found in a given plant of interest. Reference herein to the term "endogenous" is also to be understood as referring to a nucleic acid sequence in question as found in a plant of interest in its natural form (i.e., without there being any human intervention), but also as referring to that same nucleic acid sequence in an isolated form subsequently (re)introduced into said plant. The isolated nucleic acid sequence may be isolated from the organism/a plant of interest or may be manmade, for example by chemical synthesis.

Seed-specific promoters being active in seed tissues during seed filling may for instance include promoters of genes encoding seed storage proteins. Hence, in certain embodiments, said seed-specific promoter is a promoter of a gene encoding a seed storage protein. Seed storage proteins are intended to refer herein to proteins which are synthesised and stored in seeds during seed development.

In certain embodiments of the constructs, plants, or methods as taught herein, the seed-specific promoter is different from a naturally occurring TSPO promoter. In certain embodiments of the constructs, plants, or methods as taught herein, the seed-specific promoter is not a naturally occurring TSPO promoter. The terms "different from a naturally occurring TSPO promoter" or "not a naturally occurring TSPO promoter" may be used herein as synonyms. The terms "different from a naturally occurring TSPO promoter" or "not a naturally occurring TSPO promoter" as used herein intend to encompass a promoter sequence or promoter which is not a TSPO promoter or a promoter sequence or promoter which is a TSPO promoter that has been modified.

In an example a seed-specific promoter as defined herein, includes a promoter which is not a TSPO promoter (and thus which is different from a TSPO promoter), and which may be endogenous or exogenous to said plant.

In certain embodiments, the seed-specific promoter is a napin promoter (i.e. a promoter from a gene encoding a napin, preferably a napin promoter from a *Brassica* species, such as *Brassica napus*. In an example, a seed-specific promoter for use herein is a truncated version of the promoter from the 2S storage protein NapA gene from *Brassica napus* (truncated version −309 to −152) (see Ericson et al. 1991, Eur. J. Biochem 197: 741-746) or a homologue thereof from another plant species. In a preferred embodiment, said seed-specific promoter is a napin promoter having a polynucleotide sequence having at least 90% sequence identity to SEQ ID NO: 43, and for instance at least 95% or at least 97% or at least 98% or at least 99% sequence identity to SEQ ID NO: 43, or a functional fragment or homologue thereof. In a preferred embodiment, said napin promoter is represented by SEQ ID NO: 43 or a functional fragment thereof.

In certain embodiments, the seed-specific promoter is a FAE1 promoter (i.e. a promoter from a gene encoding a FAE1), preferably a FAE1 promoter from *Arabidopsis thaliana*. In an example, a seed-specific promoter for use herein is the promoter from the fatty acid elongase 1 (FAE1) (AT4G34520) gene from *Arabidopsis thaliana* (Rossak et al. 2001, Plant Molecular Biology 46: 717-725) or a homologue thereof in another plant species. In a preferred embodiment, said seed-specific promoter is a FAE1 promoter having a polynucleotide sequence having at least 90% sequence identity to SEQ ID NO: 44, and for instance at least 95% or at least 97% or at least 98% or at least 99% sequence identity to SEQ ID NO: 44 or a functional fragment or homologue thereof. In a preferred embodiment, said FAE1 promoter is represented by SEQ ID NO: 44 or a functional fragment thereof.

In certain embodiments, the seed-specific promoter is an oleosin promoter (i.e. a promoter from a gene encoding an oleosin), preferably an oleosin promoter from *Oryza sativa* (Qu and Takaiwa 2004, Plant Biotech 2: 113-125) or a functional fragment or a homologue thereof in another plant species.

The terms "functional fragment" or "active fragment" or "fragment having promoter activity" in this context are used interchangeably herein and refer to nucleic acid fragments which are capable of conferring a seed-specific transcription as described herein in a plant. For the identification of functionally active promoter fragments, the promoter strength and/or expression pattern of a candidate promoter fragment may be analyzed for example by operably linking the promoter fragment to a reporter gene and assaying the promoter activity qualitatively (spatio-temporal transcription) and/or quantitatively using techniques well known in the art. Suitable well-known reporter genes include for example β-glucuronidase or a fluorescent protein variant. The promoter activity is for instance assayed by measuring the enzymatic activity of the β-glucuronidase. The promoter fragment strength and/or expression pattern may then be compared to that of a reference promoter (such as one used in the methods of the present invention).

For expression in plants, nucleic acid sequences encoding TSPO must, as described above, be linked operably to or comprise a suitable promoter which expresses the polynucleotide at the right point in time and with the required spatial expression pattern. The promoters upstream of the TSPO polynucleotide sequences useful in the plants, constructs and methods of the present invention can be modified by one or more nucleotide substitution(s), insertion(s) and/or deletion(s) without interfering with the functionality or activity of either the promoters, the open reading frame (ORF) or the 3'-regulatory region such as terminators or other 3' regulatory regions which are located away from the ORF. It is furthermore possible that the activity of the promoters is increased by modification of their sequence.

Therefore, in certain embodiments of constructs, plants, or methods as taught herein, the applied promoter sequence may be derived from a promoter that does not have a seed-specific expression pattern, but that has been modified in order to confer a seed-specific expression as defined herein above. For instance, in certain embodiments, the promoter sequence for application in constructs, plants, or methods as taught herein may be derived from a promoter of a TSPO polynucleotide ("a TSPO promoter"), being either a TSPO polynucleotide that is endogenous or exogenous to said plant, provided that said TSPO promoter has been modified in order to confer seed-specific expression as defined herein above. Modification of such TSPO promoter may for instance be effected by genome editing. Thus, a seed-specific promoter as used herein is different from a naturally occurring (i.e. non-modified) TSPO promoter, which is either endogenous or exogenous to the plant in which it is applied. Hence, in certain embodiments of the constructs, plants, or methods as taught herein, the seed-specific promoter is not a TSPO promoter, and for instance is not a naturally occurring TSPO promoter. With "naturally occurring" TSPO promoter is meant a promoter driving the expression of the TSPO gene, which promoter is non-modified. In certain embodiments "a naturally occurring TSPO promoter" and "a TSPO promoter" may be used as synonyms.

Therefore, in certain embodiments of the constructs, plants, or methods as taught herein, a promoter sequence is used that is derived from a modified TSPO promoter, wherein said modified TSPO promoter is a TSPO promoter that has been modified in order to confer seed-specific expression as defined herein above. In a preferred embodiment, such modified TSPO promoter is derived from an endogenous TSPO promoter. In another preferred embodiment, such modified TSPO promoter is derived from an exogenous TSPO promoter.

In one example, a modified TSPO promoter sequence is used that is derived from a TSPO promoter from *Arabidopsis* as represented by SEQ ID NO: 41, or a functional fragment thereof, that has been modified in order to confer a seed-specific expression as defined herein.

In another example, a modified TSPO promoter sequence is used that is derived from a TSPO promoter from flax (*Linum usitatissimum*) as represented by SEQ ID NO: 42, or a functional fragment thereof, that has been modified in order to confer seed-specific expression as defined herein.

In certain embodiments of the constructs, plants, or methods as taught herein, the seed-specific promoter and the nucleic acid encoding a TSPO, both as defined herein, are both endogenous to said plant.

Nucleic Acid Encoding a TSPO Polypeptide

In the context of the present invention the terms "translocator protein" or "translocator polypeptide" or "TSPO protein" or TSPO polypeptide" or "TSPO" are used interchangeably and are taken to mean a TSPO polypeptide as defined herein. The terms "polypeptide" and "protein" are used interchangeably herein and refer to amino acids in a polymeric form of any length, linked together by peptide bonds. Any reference herein to a "TSPO nucleic acid" or "TSPO polynucleotide" is taken to mean a nucleic acid capable of encoding such a TSPO polypeptide.

In preferred embodiments of the constructs, plants, or methods as taught herein the term TSPO protein or TSPO nucleotide intends to refer to a protein or nucleotide which is of plant origin. A "TSPO polypeptide" as defined herein refers to a polypeptide as represented by SEQ ID NO: 2, or a homologue thereof, said homologue having at least 25% sequence identity to said TSPO.

Examples of nucleic acids encoding TSPO polypeptides are given in TABLE 1 herein. Such nucleic acids are useful for being applied in the constructs, plants and methods as taught herein. Included in TABLE 1 are amino acid sequences of homologues (orthologues and paralogues) of the TSPO polypeptide represented by SEQ ID NO: 2, the terms "orthologues" and "paralogues" being as defined herein. Further orthologues and paralogues may readily be identified by performing a so-called reciprocal blast search as described below; where the query sequence is SEQ ID NO: 1 or SEQ ID NO: 2, the second BLAST (back-BLAST) would be against *Arabidopsis* sequences.

"Homologues" of a protein as defined herein encompass peptides, oligopeptides, polypeptides, proteins and enzymes having amino acid substitutions, deletions and/or insertions relative to the unmodified protein in question and having similar biological and functional activity as the unmodified protein from which they are derived.

A deletion refers to removal of one or more amino acids from a protein.

An insertion refers to one or more amino acid residues being introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, c-myc epitope, lacZ, CMP (calmodulin-binding peptide), HA epitope, protein C epitope and VSV epitope.

A substitution refers to replacement of amino acids of the protein with other amino acids having similar properties (such as similar hydrophobicity, hydrophilicity, antigenicity, propensity to form or break α-helical structures or β-sheet structures). Amino acid substitutions are typically of single residues, but may be clustered depending upon functional constraints placed upon the polypeptide and may range from 1 to 10 amino acids; insertions will usually be of the order of about 1 to 10 amino acid residues. The amino acid substitutions are preferably conservative amino acid substitutions. Conservative substitution tables are well known in the art (see for example Creighton (1984) Proteins. W.H. Freeman and Company (Eds) and Table A below).

TABLE A

Examples of conserved amino acid substitutions

| Residue | Conserved substitutions |
|---------|------------------------|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu; Val |
| Leu | Ile; Val |
| Lys | Arg; Gln |
| Met | Leu; Ile |
| Phe | Met, Leu, Tyr |
| Ser | Thr, Gly |
| Thr | Ser; Val |
| Trp | Tyr |
| Tyr | Trp; Phe |
| Val | Ile; Leu |

Amino acid substitutions, deletions and/or insertions may readily be made using peptide synthetic techniques well known in the art, such as solid phase peptide synthesis and the like, or by recombinant DNA manipulation. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vitro mutagenesis (USB, Cleveland, Ohio), QuickChange Site Directed mutagenesis (Stratagene, San Diego, Calif.), PCR-mediated site-directed mutagenesis or other site-directed mutagenesisprotocols.

Orthologues and paralogues encompass evolutionary concepts used to describe the ancestral relationships of genes. Paralogues are genes within the same species that have originated through duplication of an ancestral gene; orthologues are genes from different organisms that have originated through speciation, and are also derived from a common ancestral gene.

A Reciprocal BLAST typically involves a first BLAST involving BLASTing a query sequence (for example using any of the sequences listed in Table 1 of the Examples section) against any sequence database, such as the publicly available NCBI database. BLASTN or TBLASTN (using standard default values) are generally used when starting from a nucleotide sequence, and BLASTP or TBLASTX (using standard default values) when starting from a protein sequence. The BLAST results may optionally be filtered. The full-length sequences of either the filtered results or non-filtered results are then BLASTed back (second BLAST) against sequences from the organism from which the query sequence is derived. The results of the first and second BLASTs are then compared. A paralogue is identified if a high-ranking hit from the first blast is from the same species as from which the query sequence is derived, a BLAST back then ideally results in the query sequence amongst the highest hits; an orthologue is identified if a high-ranking hit in the first BLAST is not from the same species as from which the query sequence is derived, and preferably results upon BLAST back in the query sequence being among the highest hits. High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. In the case of large families, ClustalW may be used, followed by a neighbor joining tree, to help visualize clustering of related genes and to identify orthologues and paralogues.

TABLE 1

Examples of TSPO polypeptides for use in the present invention

| Name | Nucleic acid SEQ ID NO: | Polypeptide SEQ ID NO: |
|---|---|---|
| Arabidopsis thaliana | 1 | 2 |
| Arabidopsis thaliana | 3 | 4 |
| Arabidopsis thaliana | 5 | 6 |
| Arabidopsis thaliana | 7 | 8 |
| Arabidopsis thaliana | 9 | 10 |
| Arabidopsis thaliana | 11 | 12 |
| Arabidopsis thaliana | 13 | 14 |
| Arabidopsis thaliana | 15 | 16 |
| Brassica napus | 17 | 18 |
| Brassica napus | 19 | 20 |
| Brassica napus | 21 | 22 |
| Brassica napus | 23 | 24 |
| Brassica rapa | 25 | 26 |
| Brassica rapa | 27 | 28 |
| Oryza sativa | 29 | 30 |
| Camelina sativa | 31 | 32 |
| Linum usitatissimum | 33 | 34 |
| Zea mays | 35 | 36 |
| Helianthus annuus | 37 | 38 |
| Helianthus annuus | 39 | 40 |

In a preferred embodiment, a TSPO polypeptide useful in the constructs, plants and methods of the invention or a homologue thereof has in increasing order of preference at least 25%, 26%, 27%, 28%, 29%, 30%, 31%, 32%, 33%, 34%, 35%, 36%, 37%, 38%, 39%, 40%, 41%, 42%, 43%, 44%, 45%, 46%, 47%, 48%, 49%, 50%, 51%, 52%, 53%, 54%, 55%, 56%, 57%, 58%, 59%, 60%, 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% overall sequence identity to the amino acid represented by SEQ ID NO: 2. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides).

In a preferred embodiment, a TSPO polypeptide useful in the plants and methods of the invention is represented by SEQ ID NO: 2 or a homologue thereof having at least 25%, or at least 60%, or at least 75%, or at least 85%, or at least 90% overall sequence identity to SEQ ID NO: 2.

In a preferred embodiment, a TSPO polypeptide useful in the plants and methods of the invention is represented by SEQ ID NO: 32 or a homologue thereof having at least 25%, or at least 60%, or at least 75%, or at least 85%, or at least 90% overall sequence identity to SEQ ID NO: 32.

In a preferred embodiment, a TSPO polypeptide useful in the plants and methods of the invention is represented by SEQ ID NO: 34 or a homologue thereof having thereof having at least 25%, or at least 60%, or at least 75%, or at least 85%, or at least 90% overall sequence identity to SEQ ID NO: 34.

In certain embodiments a homologue of a TSPO polypeptide useful in the constructs, plants and methods of the invention may also include a "modified TSPO polypeptide". A TSPO polypeptide as taught herein may be conveniently denoted as "modified", or as "mutated" or "mutant", or as comprising one or more mutations, i.e., comprising one or more amino acid sequence changes compared to the amino acid sequence of the TSPO polypeptide that has not been mutated, such as, particularly, compared to the amino acid sequence of a wild type TSPO polypeptide.

The *Arabidopsis* TSPO polypeptide contains two histidine residues at positions 91 (H91) and at position 115 (H115) in its sequence as represented by SEQ ID NO: 2. Both residues appear to be relatively well conserved in angiosperm TSPOs (see Vanhee et al. 2011).

Therefore, in one embodiment, a modified TSPO polypeptide is provided herein for use in the plants and methods as taught herein, which comprises a mutation replacing the histidine amino acid with an alanine amino acid at a position corresponding to position 91 of SEQ ID NO: 2. In particular, a modified TSPO polypeptide is provided herein which is represented by SEQ ID NO: 4 and encoded by the nucleic acid represented by SEQ ID NO: 3.

In another embodiment, a modified TSPO polypeptide is provided which comprises a mutation replacing the histidine amino acid to the alanine amino acid at a position corresponding to position 115 of SEQ ID NO: 2. In particular, a modified TSPO polypeptide is provided herein which is represented by SEQ ID NO: 6 and encoded by the nucleic acid represented by SEQ ID NO: 5.

In another embodiment, a modified TSPO polypeptide is provided which comprises a first mutation replacing the histidine amino acid with an alanine amino acid at a position corresponding to position 91 of SEQ ID NO: 2, and a second mutation replacing the histidine amino acid to the alanine amino acid at a position corresponding to position 115 of SEQ ID NO: 2. In particular, a modified TSPO polypeptide is provided herein which is represented by SEQ ID NO: 8 and encoded by the nucleic acid represented by SEQ ID NO: 7.

In another embodiment, a modified TSPO polypeptide is provided which comprises a mutation replacing the cysteine amino acid with a tryptophan amino acid at a position corresponding to position 94 of SEQ ID NO: 2. In particular, a modified TSPO polypeptide is provided herein which is represented by SEQ ID NO: 10 and encoded by the nucleic acid represented by SEQ ID NO: 9.

In another embodiment, a modified TSPO polypeptide is provided which comprises a mutation replacing the tyrosine amino acid with a alanine amino acid at a position corresponding to position 122 of SEQ ID NO: 2. In particular, a modified TSPO polypeptide is provided herein which is represented by SEQ ID NO: 12 and encoded by the nucleic acid represented by SEQ ID NO: 11.

In another embodiment, a modified TSPO polypeptide is provided which comprises a mutation replacing the tyrosine amino acid with a alanine amino acid at a position corresponding to position 124 of SEQ ID NO: 2. In particular, a modified TSPO polypeptide is provided herein which is represented by SEQ ID NO: 14 and encoded by the nucleic acid represented by SEQ ID NO: 13.

In another embodiment, a modified TSPO polypeptide is provided which comprises a first mutation replacing the tyrosine amino acid with a alanine amino acid at a position corresponding to position 122 of SEQ ID NO: 2, and a second mutation replacing the tyrosine amino acid with a alanine amino acid at a position corresponding to position 124 of SEQ ID NO: 2. In particular, a modified TSPO polypeptide is provided herein which is represented by SEQ ID NO: 16 and encoded by the nucleic acid represented by SEQ ID NO: 15.

As there is sequence homology between plant TSPO polypeptides, TSPO polypeptides, and the nucleic acids encoding them, carrying one or more of mutation(s) as described above, at a position corresponding to the positions as described above for wild type *Arabidopsis* TSPO (represented by SEQ ID NO: 2), whatever the relative position is of these amino acids with respect to positions as indicated above of wild type *Arabidopsis* TSPO, can be used in the present invention. To apply this principle, those skilled in the art will be readily able to find the one or two amino acids and/or the nucleotides to be mutated in any TSPO polynucleotide sequence by using standard techniques of sequence alignment. Alternatively, using the genetic code, one of skill in the art will also be able to find the appropriate nucleotide modifications in a TSPO polynucleotide sequence.

In this context the term "corresponding to" will be immediately understood by a skilled person as the correspondence between nucleotide(s) of two forms of a TSPO polynucleotide. By means of example, such corresponding nucleotides may be located at the same position in an alignment of the nucleotide sequences of the two forms of a TSPO polynucleotide. The sequence alignment may be generated as explained elsewhere, in connection with the determination of the extent of sequence identity. Likewise, the skilled person will have an immediate understanding of the correspondence between amino acid(s) of two forms of a TSPO polypeptide. By means of example, such corresponding amino acids may be located at the same position in an alignment of the primary amino acid sequences of the two forms of a TSPO polypeptide. The sequence alignment may be generated as explained elsewhere in the specification, in connection with the determination of the extent of sequence identity.

In certain embodiments, the "TSPO polypeptide" useful in the constructs, plants and methods of the invention refers to a polypeptide having certain consensus sequences, motifs, and/or domains.

The term "domain" refers to a set of amino acids conserved at specific positions along an alignment of sequences of evolutionarily related proteins. While amino acids at other positions can vary between homologues, amino acids that are highly conserved at specific positions indicate amino acids that are likely essential in the structure, stability or function of a protein. Identified by their high degree of conservation in aligned sequences of a family of protein homologues, they can be used as identifiers to determine if any polypeptide in question belongs to a previously identified polypeptide family.

The term "motif or "consensus sequence" refers to a short conserved region in the sequence of evolutionarily related proteins. Motifs are frequently highly conserved parts of domains, but may also include only part of the domain, or be located outside of conserved domain (if all of the amino acids of the motif fall outside of a defined domain).

Specialist databases well known in the art exist for the identification of domains, for example, SMART, InterPro, Prosite, or Pfam. Domains or motifs may also be identified using routine techniques, such as by sequence alignment. The overall sequence identity is determined using a global alignment algorithm, such as the Needleman Wunsch algorithm in the program GAP (GCG Wisconsin Package, Accelrys), preferably with default parameters and preferably with sequences of mature proteins (i.e. without taking into account secretion signals or transit peptides). Compared to overall sequence identity, the sequence identity will generally be higher when only conserved domains or motifs are considered.

By aligning other protein sequences with SEQ ID NO: 2, the corresponding domains as mentioned herein may easily be identified. In this way, TSPO polypeptides or homologues thereof (encompassing orthologues and paralogues) may readily be identified, using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch to find the alignment of two complete sequences that maximizes the number of matches and minimizes the number of gaps. The BLAST algorithm calculates percent sequence identity and performs a statistical analysis of the similarity between the two sequences. The software for performing BLAST analysis is publicly available through the National Centre for Biotechnology Information. Homologues may readily be identified using, for example, the ClustalW multiple sequence alignment algorithm with the default pairwise alignment parameters, and a scoring method in percentage. Global percentages of similarity and identity may also be determined using one of the methods available in the MatGAT software package. Minor manual editing may be performed to optimize alignment between conserved motifs, as would be apparent to a person skilled in the art. Furthermore, instead of using full-length sequences for the identification of homologues, specific domains (such as defined above) may be used as well. The sequence identity values, which are indicated herein as a percentage are determined over the entire conserved domain or nucleic acid or amino acid sequence using the programs mentioned above using the default parameters.

In certain embodiments, the TSPO polypeptide is defined as comprising a tryptophan-rich sensory protein/peripheral-type benzodiazepine receptor domain (TspO/MBR domain). The TspO/MBR domain may be structurally defined by the presence of several (e.g. 5) transmembrane domains, and presents high conservation across different species in respect of its 3-D folding structure. It is within the skill of the ordinary skilled person to identify polypeptides having a TspO/MBR domain using commonly known databases.

In certain embodiments, the TSPO polypeptide is defined as comprising an N-terminal domain (an N-terminal extension domain). Preferably such TSPO N-terminal domain is rich in basic residues with a net positive charge. A skilled person will readily know how to identify proteins having such N-terminal domain.

In certain embodiments, the TSPO polypeptide is defined as comprising a domain, in particular a tryptophan-rich sensory protein/peripheral-type benzodiazepine receptor domain (TspO/MBR domain) having at least 30% sequence identity to the TspO/MBR domain as represented by SEQ ID NO: 49, and for instance at least 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% overall sequence identity to the amino acid represented by SEQ ID NO: 49.

In certain embodiments, the TSPO polypeptide is defined as comprising a N-terminal domain having at least 30% sequence identity to the N-terminal domain as represented by SEQ ID NO: 50; and for instance at least 35%, 40%, 45%, 50%, 55%, 60%, 65%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% overall sequence identity to the amino acid represented by SEQ ID NO: 50.

In certain embodiments, the TSPO polypeptide comprises a conserved domain (or motif) having at least 70% sequence identity; and for instance at least 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or 100% overall sequence identity to the amino acid represented by SEQ ID NO: 51.

As indicated above, any reference herein to a "TSPO nucleic acid" or "TSPO polynucleotide" or "nucleic acid encoding a TSPO" is taken to mean a nucleic acid capable of encoding a TSPO polypeptide as defined herein. Reference herein to a "TSPO nucleic acid" or "TSPO polynucleotide" or "nucleic acid encoding a TSPO" is taken to mean a polymeric form of a deoxyribonucleotide or a ribonucleotide polymer of any length, either double- or single-stranded, or analogues thereof, that has the essential characteristic of a natural ribonucleotide in that it can hybridize to nucleic acid sequences in a manner similar to naturally occurring polynucleotides.

In certain embodiments, the TSPO polynucleotide may originate or may be derived from a wild-type or native TSPO polynucleotide.

In certain embodiments, a TSPO polynucleotide as taught herein may comprise or consist of a genomic sequence of a TSPO gene starting with a translation initiation codon and closing with a translation termination codon known per se (and not containing any internal in-frame translation termination codon). In certain embodiments, the TSPO polynucleotide may comprise or consist of (coding) exons and one or more (non-coding) introns. In certain embodiments, the TSPO polynucleotide may comprise or consist of an open reading frame (ORF) known per se, which may span multiple exons. The term "genomic sequence" refers to a succession of nucleotides as found in the genome of an organism (e.g., a plant).

In certain embodiments, the TSPO polynucleotide may comprise or consist of a coding region of a TSPO gene. In certain embodiments, the TSPO polynucleotide may comprise or consist of a succession of coding nucleotide triplets (codons) starting with a translation initiation codon and closing with a translation termination codon known per se (and not containing any internal in-frame translation termination codon). In certain embodiments, the TSPO polynucleotide may comprise or consist of (coding) exons. The terms "coding region of a gene", "coding sequence", "coding DNA sequence" or "CDS" refers to that portion of a gene, comprising a succession of coding nucleotide triplets (codons), which codes for protein.

In certain embodiments, said nucleic acid encoding a TSPO polypeptide is a nucleic acid that encodes a TSPO polypeptide represented by SEQ ID NO: 2, or a homologue thereof, said homologue having at least 25% sequence identity, and for instance at least 30%, 35%, 40%, 45%, 50%, 55%, 60%, 65%, 70%, 75%, 80%, 85%, 90%, 95%, 96%, 97%, 98%, or 99% overall sequence identity, to the amino acid represented by SEQ ID NO: 2, and that further comprises a N-terminal domain having at least 30% sequence identity, and for instance at least 35%, 40%, 45%, 50%, 55%, 60%, 65%, 70%, 75%, 80%, 85%, 90%, 95%, 96%, 97%, 98%, or 99% sequence identity, to the N-terminal domain as represented by SEQ ID NO: 50.

In certain embodiments, said nucleic acid encoding a TSPO polypeptide is a nucleic acid that encodes a TSPO polypeptide represented by SEQ ID NO: 32, or a homologue thereof, said homologue having at least 25% sequence identity, and for instance at least 30%, 35%, 40%, 45%, 50%, 55%, 60%, 65%, 70%, 75%, 80%, 85%, 90%, 95%, 96%, 97%, 98%, or 99% overall sequence identity, to the amino acid represented by SEQ ID NO: 32, and that further comprises a N-terminal domain having at least 30% sequence identity, and for instance at least 35%, 40%, 45%, 50%, 55%, 60%, 65%, 70%, 75%, 80%, 85%, 90%, 95%, 96%, 97%, 98%, or 99% sequence identity, to the N-terminal domain as represented by SEQ ID NO: 50.

In certain embodiments, said nucleic acid encoding a TSPO polypeptide is a nucleic acid that encodes a TSPO polypeptide represented by SEQ ID NO: 34, or a homologue thereof, said homologue having at least 25% sequence identity, and for instance at least 30%, 35%, 40%, 45%, 50%, 55%, 60%, 65%, 70%, 75%, 80%, 85%, 90%, 95%, 96%, 97%, 98%, or 99% overall sequence identity, to the amino acid represented by SEQ ID NO: 34, and that further comprises a N-terminal domain having at least 30% sequence identity, and for instance at least 35%, 40%, 45%, 50%, 55%, 60%, 65%, 70%, 75%, 80%, 85%, 90%, 95%, 96%, 97%, 98%, or 99% sequence identity, to the N-terminal domain as represented by SEQ ID NO: 50.

Examples of a TSPO polynucleotide from *Arabidopsis* and other exemplary TSPO polynucleotides are presented in TABLE 1 given herein. In an example, a coding sequence of an exemplary wild type TSPO polynucleotide from *Arabidopsis* is as set forth in SEQ ID NO: 1. The corresponding amino acid sequence of said exemplary wild type TSPO polypeptide from *Arabidopsis* is as set forth in SEQ ID NO: 2.

Variants of TSPO polynucleotides as defined herein above may also be useful in the constructs, plants or methods of the invention. A variant of a TSPO polynucleotide may be selected from the group comprising:
  (i) a nucleic acid hybridizing to a TSPO polynucleotide as defined herein;
  (ii) a splice variant of a TSPO polynucleotide as defined herein;
  (iii) an allelic variant of a TSPO polynucleotide as defined herein;
  (iv) a modified TSPO polynucleotide as defined herein.

Other examples of variants of a TSPO polynucleotide may also include TSPO polynucleotides as defined herein in which codon usage is optimized or in which miRNA target sites are removed.

The terms hybridizing sequence, splice variant, allelic variant, or modified polynucleotide are as described below.

In certain embodiments, a variant of a TSPO polynucleotide useful in the constructs, plants and methods of the present invention is a nucleic acid capable of hybridizing, preferably under stringent conditions, with a TSPO polynucleotide as hereinbefore defined.

A nucleic acid is "hybridizable" to another nucleic acid, such as a cDNA, genomic DNA, or RNA, when a single stranded form of the nucleic acid can anneal to the other nucleic acid under the appropriate conditions of temperature and solution ionic strength.

Hybridization and washing conditions are well known and exemplified in Sambrook et al. Molecular Cloning: A Laboratory Manual, Second Edition, Cold Spring Harbor Laboratory Press, Cold Spring Harbor (1989); and Sambrook, J. and Russell, W., Molecular Cloning: A Laboratory Manual, Third Edition, Cold Spring Harbor Laboratory Press, Cold Spring Harbor (2001).

As used herein, "stringent" conditions for hybridization refers to conditions wherein hybridization is carried out overnight at 20-25° C. below the melting temperature (Tm) of the DNA hybrid in 6×SSPE, 5×Denhardt's solution, 0.1% SDS, 0.1 mg/ml denatured DNA. The melting temperature, Tm, is described by the following formula (Beltz et al., 1983, Methods Enzymol. 100:266-285):

$$Tm = 81.5\ C + 16.6\ Log\ [Na+] + 0.41(\%\ G+C) - 0.61(\%\ formamide) - 600/\text{length of duplex in base pairs}.$$

Washes are typically carried out as follows:

(1) Twice at room temperature for 15 minutes in 1×SSPE, 0.1% SDS (low stringency wash).

(2) Once at Tm−20° C. for 15 minutes in 0.2×SSPE, 0.1% SDS.

Hybridization requires that the two nucleic acids contain complementary sequences, although depending on the stringency of the hybridization, mismatches between bases are possible. The appropriate stringency for hybridizing nucleic acids depends on the length of the nucleic acids and the degree of complementation, variables well known in the art. The greater the degree of similarity or homology between two nucleotide sequences, the greater the value of the melting temperature (Tm) for hybrids of nucleic acids having those sequences. The relative stability (corresponding to higher Tm) of nucleic acid hybridizations decreases in the following order: RNA:RNA, DNA:RNA, DNA:DNA. For hybrids of greater than 100 nucleotides in length, equations for calculating Tm have been derived (see Sambrook et al. 1989). For hybridizations with shorter nucleic acids, i.e., oligonucleotides, the position of mismatches becomes more important, and the length of the oligonucleotide determines its specificity (see Sambrook et al. 1989). Typically, the length for a hybridizable nucleic acid is at least about 10 nucleotides. Illustrative minimum lengths for a hybridizable nucleic acid are: at least about 15 nucleotides; at least about 20 nucleotides; and at least about 30 nucleotides. Furthermore, the skilled artisan will recognize that the temperature and wash solution salt concentration may be adjusted as necessary according to factors such as length of the probe.

In certain embodiments, high stringency hybridization conditions for DNA hybrids longer than 50 nucleotides may encompass hybridization at 65° C. in 1×SSC or at 42° C. in 1×SSC and 50% formamide, followed by washing at 65° C. in 0.3×SSC. Examples of medium stringency hybridization conditions for DNA hybrids longer than 50 nucleotides encompass hybridization at 50° C. in 4×SSC or at 40° C. in 6×SSC and 50% formamide, followed by washing at 50° C. in 2×SSC.

Preferably, a hybridizing sequence as taught according to the invention is a sequence that is capable of hybridizing to a nucleic acid as represented by any of the TSPO nucleotide sequences presented in TABLE 1.

In certain embodiments a variant of a TSPO polynucleotide useful in the constructs, plants and methods of the present invention is a splice variant encoding a TSPO polypeptide as defined hereinbefore. The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained; this may be achieved by selectively retaining functional segments of the protein. Such splice variants may be found in nature or may be manmade. Methods for predicting and isolating such splice variants are well known in the art.

In certain embodiments a variant of a TSPO polynucleotide useful in the constructs, plants and methods of the present invention is an allelic variant of a TSPO polynucleotide encoding a TSPO polypeptide as defined hereinbefore. Alleles or allelic variants are alternative forms of a given gene, located at the same chromosomal position. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

In certain embodiments a variant of a TSPO polynucleotide useful in the constructs, plants and methods of the present invention may also include a TSPO polynucleotide which is modified. A TSPO polynucleotide as taught herein may be conveniently denoted as "modified", or as "mutated" or "mutant", or as comprising one or more mutations, i.e., comprising one or more nucleic acid sequence changes compared to the nucleic acid sequence of TSPO polynucleotide that has not been mutated, such as, particularly, compared to the nucleic acid sequence of a wild type TSPO polynucleotide.

In certain embodiments, a modified TSPO polynucleotide may be a TSPO polynucleotide which is modified in order to encode a modified TSPO polypeptide as hereinbefore defined.

For example, in an embodiment, a modified TSPO polynucleotide may be a TSPO polynucleotide from *Arabidopsis* as set forth in any one of SEQ ID NOs: 3, 5, 7, 9, 11, 13, or 15.

TSPO polynucleotides or variants thereof may be derived from any natural or artificial source. These polynucleotides may be modified as explained above through deliberate human manipulation.

In certain embodiments, the TSPO polynucleotide or variants thereof as defined herein may originate or may be derived from a plant or a microorganism. In a preferred embodiment, the TSPO polynucleotide or variant thereof is derived from a plant.

For example, the TSPO polynucleotide may originate or may be derived from a monocotyledonous plant. In certain embodiments of the constructs, plants or methods as taught herein, the TSPO polynucleotide may originate or may be derived from a plant selected from the group comprising rice, oil palm, wheat, maize, barley, and sorghum.

In another example, the TSPO polynucleotide may originate or may be derived from a dicotyledonous plant. In certain embodiments of the constructs, plants or methods as taught herein, the TSPO polynucleotide may originate or may be derived from a plant from the plant family selected from the group comprising Brassicaceae (e.g. *Arabidopsis*, oilseed rape, mustard, *Camelina, Brassica rapa*), Solanaceae (e.g. potato), Linaceae (e.g. flax), Euphorbiaceae (e.g. *Ricinus communis*), Vitaceae (e.g. *Vitis vinifera*), Fabaceae (e.g. soybean, peanut, *medicago*), Asteraceae (e.g. safflower, sunflower) and Lamiaceae (e.g. sesame) and Salicaceae (e.g. *Populus*). In certain embodiments of the plants or methods as taught herein, the TSPO polynucleotide may originate or may be derived from a plant selected from the group comprising *Arabidopsis*, oilseed rape (*Brassica napus*), canola, *Brassica rapa* (turnip rape), linseed (flaxseed) or *Camelina*.

In an embodiment, the TSPO polynucleotide is an *Arabidopsis thaliana* sequence. In another embodiment the TSPO polynucleotide is a *Camelina* sequence. In another embodiment the TSPO polynucleotide is a *Linum* sequence. In another embodiment the TSPO polynucleotide is a *Brassica* sequence. In another embodiment the TSPO polynucleotide is a sunflower sequence. In another embodiment the TSPO polynucleotide is a maize sequence. In another embodiment the TSPO polynucleotide is a rice sequence.

Transcription Terminator Sequence

A transcription terminator sequence as used herein refers to a control sequence which is a DNA sequence at the end of a transcriptional unit which signals 3' processing and polyadenylation of a primary transcript and termination of transcription. A terminator sequence can be derived from the natural TSPO gene, from a variety of other plant genes, or from T-DNA. Examples include for instance a terminator obtained or derived from a nopaline synthase or octopine synthase genes, or alternatively from other plant genes.

In certain embodiments of constructs, plants or methods as taught herein, the transcription terminator sequence may be at least 100 nucleotides in length, such as at least 150 nucleotides, at least 200 nucleotides, at least 250 nucleotides, or at least 300 nucleotides, in length.

In certain embodiments of constructs, plants or methods as provided herein, the transcription terminator sequence may be at most 4000 nucleotides in length, such as at most 3500 nucleotides, at most 3000 nucleotides, at most 2750 nucleotides, or at most 2500 nucleotides, in length.

A transcription terminator sequence useful in constructs, plants or methods as taught herein, may be any transcription terminator sequence of plant origin.

In certain embodiments of constructs, plants or methods as taught herein, the transcription terminator sequence may originate or may be derived from a monocotyledonous plant. In certain embodiments, the transcription terminator sequence may originate or may be derived from a plant selected from the group comprising rice, oil palm, wheat, maize, barley, and sorghum.

In certain other embodiments of constructs, plants or methods as taught herein, the transcription terminator sequence may originate or may be derived from a dicotyledonous plant. In certain embodiments the transcription terminator sequence may originate or may be derived from a dicotyledonous plant selected from the group comprising of *Arabidopsis*, oilseed rape, canola, turnip rape, linseed, soybean, sunflower, cotton, castor bean, peanut, and sesame.

In certain embodiments of constructs, plants or methods as taught herein, the transcription terminator sequence is a transcription terminator sequence (from a gene) which is endogenous to said plant. In certain other embodiments of constructs, plants or methods as taught herein, the transcription terminator sequence is a transcription terminator sequence (from a gene) which is exogenous to said plant.

In certain embodiments of constructs, plants or methods as taught herein, the transcription terminator sequence is not derived from a TSPO terminator sequence. In certain other embodiments of constructs, plants or methods as taught herein, the transcription terminator sequence may be derived from a TSPO terminator sequence, which is either endogenous or exogenous to said plant.

A construct according to the invention may be further provided with additional regulatory elements. Additional regulatory elements may include transcriptional as well as translational enhancers. Those skilled in the art will be aware of enhancer sequences that may be suitable for use in performing the invention. An intron sequence may also be added to the 5' untranslated region (UTR) or in the coding sequence. Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

Constructs according to the invention may further include an origin of replication sequence that is required for maintenance and/or replication in a specific cell type. One example is when a genetic construct is required to be maintained in a bacterial cell as an episomal genetic element (e.g. plasmid or cosmid molecule). A preferred origin of replication includes but is not limited to colE1.

For the detection of the successful transfer of the nucleic acid sequences as used in the methods of the invention and/or selection of transgenic plants comprising these nucleic acids, it is advantageous to use marker genes (or reporter genes). Therefore, a construct may optionally comprise a selectable marker gene. Selectable markers would be known or may readily be obtained by a person skilled in the art. The marker genes may be removed or excised from the transgenic cell once they are no longer needed. Techniques for marker removal are known in the art.

Vectors, Host Cells

In certain embodiments, a construct as taught herein may be introduced in the genome of a cell (e.g., of the plant) in which the construct is expressed. The construct as taught herein can be transiently introduced in the cell (e.g., of the plant) in which a TSPO polynucleotide as taught herein is expressed or can be stably introduced in the genome of the cell (e.g., of the plant) in which a TSPO polynucleotide as taught herein is expressed. A TSPO polynucleotide can be introduced in the cell (e.g. of the plant) in which the protein is expressed via methods known in the art such as transformation. A construct according to the invention may then be inserted into vectors, which may be commercially available, suitable for transforming into plants and suitable for (transiently or stably) expressing of the gene of interest, i.e. a TSPO polynucleotide, in the transformed cells.

The terms "introduction" or "transformation" or "transformed" are used interchangeably herein with "genetic modification" or "genetically modified" and refer to a permanent or transient genetic change induced in a cell following introduction of a nucleic acid (i.e., DNA exogenous to the cell). Genetic change ("modification") can be accomplished either by incorporation of the new DNA into the genome of the host cell, or by transient or stable maintenance of the new DNA as an episomal element. Where the cell is a eukaryotic cell, a permanent genetic change is generally achieved by introduction of the DNA into the genome of the cell or into a plastome of the cell. In prokaryotic cells, permanent changes can be introduced into the chromosome or via extrachromosomal elements such as plasmids, plastids, and expression vectors, which may contain one or more selectable markers to aid in their maintenance in the recombinant host cell.

In another embodiment, the invention relates to a recombinant vector (e.g. a plasmid) comprising a construct as defined herein, and use thereof in the methods of the invention.

In another embodiment, the invention provides a host cell comprising a construct as defined herein. In yet another embodiment, the invention provides a host cell transformed with a construct as defined herein. Preferably said host cell is a bacterial cell, e.g. an *E. coli* cell or an *Agrobacterium* cell, or a yeast cell or a plant cell.

In one embodiment, plants are transformed with a vector comprising any of the TSPO polynucleotides described above. The skilled artisan is well aware of the genetic elements that must be present on the vector in order to successfully transform, select and propagate host cells containing the gene of interest.

In certain other embodiment a construct as taught herein may not be present in the same chromosomal location as compared to an endogenous TSPO construct. Thus, a construct as disclosed herein may be present in a chromosomal location which is different from the chromosomal location of the endogenous TSPO construct.

In certain other embodiments, a construct as defined herein is present in the same chromosomal location as compared to an endogenous (non-modified) TSPO construct. For instance, in certain preferred embodiments, the construct as taught herein may be an endogenous construct which is modified to confer seed-specific expression, hence a construct comprising the following operably linked nucleic acid sequences: an endogenous TSPO polynucleotide and its endogenous TSPO promoter sequence, and optionally its endogenous TSPO transcription terminator sequence, wherein said endogenous TSPO promoter sequence has been modified (e.g. by genome editing) in order to confer seed-specific expression as defined herein of the TSPO nucleic acid.

Plants and Methods for Modified Lipid Metabolism

It has been found that modulating the expression in a plant of a TSPO nucleic acid encoding a TSPO polypeptide as defined herein gives plants having a modified lipid metabolism as compared to control plants. More in particular, it has been found that expression in a plant a TSPO nucleic acid encoding a TSPO polypeptide as defined herein in a seed-specific manner in plants gives plants having an enhanced level of triacylglycerol (TAG) as compared to control plants.

The term "plant" as used throughout the specification encompasses whole plants, ancestors and progeny of the plants and plant parts, including seeds, shoots, stems, leaves, roots (including tubers), flowers, and tissues and organs, wherein each of the aforementioned comprise the gene/nucleic acid of interest. In certain embodiments, the term "plant" also encompasses plant cells, suspension cultures, callus tissue, embryos, meristematic regions, gametophytes, sporophytes, pollen and microspores, again wherein each of the aforementioned comprises the nucleic acid and construct of interest.

Plants that are particularly useful in the methods of the invention include all oil-producing plants, i.e. plants which are capable of producing oil, either edible or non-edible. The term "plant capable of producing an oil" as used herein refers to plants that can be used to obtain oils (fats) from their seeds. Such plants have been widely cultivated as sources for edible oils, such as rapeseed oil and sesame oil, or as sources for a variety of (non-edible) oils for industrial use. For example, *Brassica* plants, of which seeds include lipids at about 60% of the seed weight, are cultivated in various places in the world. The seed meals contain proteins at high level and have been used as feed. A skilled person is well aware of what are oil-producing plants.

Any oil-producing plants that can be used for extraction of oils (fats) from their seeds may be used in the present invention. In a preferred embodiment, plants according to the present invention can be selected from the list comprising canola, oilseed rape, turnip rape, sesame, *Camelina*, peanut, soybean, maize, sunflower, safflower, rice, linseed, cotton, mustard, castor beans and peanuts.

The choice of suitable "control plants" is a routine part of an experimental setup and may include corresponding wild type plants. The control plant is typically of the same plant species or even of the same variety as the plant to be assessed. A "control plant" as used herein may refer not only to whole plants, but may also refer to plant parts, including seeds and seed parts. A control plant may typically be a wild-type, i.e. a non-modified plant.

The term "modified lipid metabolism" as used herein is to be understood in its broadest sense, and involves a change in the synthesis, accumulation, storage or breakdown of lipids in a modified plant as compared to control plants.

In a preferred embodiment, a "modified lipid metabolism" intends to refer to the production of an enhanced amount of triacylglycerol (TAG) in a modified plant (or parts thereof) in comparison to control plants (or parts thereof).

As used herein the term "TAG" or "triacylglyerol" intends to refer to esters derived from glycerol and fatty acids, wherein said fatty acids are selected from the group comprising long chain fatty acids (LCFA) and very long chain fatty acids (VLCFA). As used herein the term "LCFA" intends to refer to long chain fatty acids comprising 13 to 18 carbon atoms, such as but not limited to palmitic acid (C16:0), stearic acid (C18:0), oleic acid (C18:1). As used herein the term "VLCFA" intends to refer to very long chain fatty acids comprising more than 18 carbon atoms.

In the context of the invention, the terms "increased" or "enhanced" amount of TAG in plants (or parts thereof) and shall mean an overall amount of TAG which is at least 3%, 4%, 5%, 6%, 7%, 8%, 9% or 10%, preferably at least 15% or 20%, preferably at least 25%, 30%, 35%, 40%, 45% or 50% higher in the modified plants (or parts thereof) in comparison to control plants (or parts thereof) as defined herein.

In certain embodiments, the terms "increased" or "enhanced" amount of TAG in plants (or parts thereof) according to the invention, may also mean an overall amount of TAG which is at least 1.5 fold, and for instance at least 1.8 fold, or at least 2.0 fold higher, than the overall amount of TAG in control plants.

In certain embodiments, the terms "increased" or "enhanced" amount of TAG in plants (or parts thereof) according to the invention, may also refer to an increase in the amount of (certain) fatty acids, selected from the group comprising long chain fatty acids (LCFA) and very long chain fatty acids (VLCFA) as defined, as compared to control plants, and for instance an amount which is at least 1.5 fold higher, and for instance at least 1.8 fold higher, or at least 2.0 fold higher than the amount of said fatty acids in control plants.

In certain embodiments, the invention relates to a plant, plant part, including seeds, or a plant cell comprising a construct, wherein said construct comprises the following operably linked nucleic acid sequences: a) a promoter sequence, b) a nucleic acid encoding a TSPO polypeptide, and optionally c) a transcription terminator sequence, wherein said promoter sequence is a seed-specific promoter which is active in seed tissues during seed filling; and wherein said construct confers a modified lipid metabolism to said plant, plant part or plant cell, as compared to a control plant, plant part or plant cell.

In certain embodiments, the invention provides a plant, plant part or plant cell comprising a construct as defined herein.

In certain embodiments the invention provides a plant, plant part or plant cell transformed with a construct as defined herein.

Plants according to the present invention may pass along the construct, including the TSPO gene under the control of a seed-specific promoter which is active in seed tissues during seed filling, to progeny. As used herein, "progeny" includes any plant, seed, plant cell, and/or plant part comprising the construct derived from an ancestor plant and/or a TSPO gene as defined herein under the control of a seed-specific promoter as defined herein. Plants, plant parts or plant cell, progeny, and seeds may be homozygous or heterozygous for the construct or for the seed-specific promoter—TSPO gene combination as defined herein.

In another embodiment the invention relates to a plant, plant part, or a plant cell as taught herein, wherein said modified lipid metabolism comprises an enhanced amount of triacylglycerol in said plant, plant part or plant cell as compared to a control plant, plant part or plant cell.

In another embodiment the invention relates to a plant, plant part, or a plant cell as taught herein, wherein said modified lipid metabolism comprises an enhanced amount of triacylglycerol, wherein said triacylglycerol is an ester derived from glycerol and fatty acids, wherein said fatty acids are selected from the group comprising long chain fatty acids (LCFA) comprising 13 to 18 carbon atoms and very long chain fatty acids (VLCFA) comprising more than 18 carbon atoms.

The present invention also relates to methods for modifying the lipid metabolism in a plant or part thereof, and for making (transgenic) plants having a modified lipid metabolism.

In an embodiment, the invention relates to a method for modifying the lipid metabolism in a plant, or part thereof, as compared to a control plant comprising the step of modulating the expression in a plant of a nucleic acid encoding a TSPO polypeptide as defined herein. In particular, the invention provides a method for modifying the lipid metabolism in a plant as compared to a control plant comprising the step of conferring a seed-specific expression in a plant to a nucleic acid encoding a TSPO polypeptide as defined herein.

The term "modulation" in this context means in relation to expression or gene expression, a process in which the expression level and/or expression pattern is changed by said gene expression in comparison to the control plant.

In a further embodiment, the invention relates to a method for modifying the lipid metabolism in a plant as compared to a control plant comprising the step of providing a plant comprising a construct, wherein said construct comprises the following operably linked nucleic acid sequences: a promoter sequence, a nucleic acid encoding a TSPO polypeptide, and optionally a transcription terminator sequence, wherein said promoter sequence is a seed-specific promoter which is active in seed tissues during seed filling. In a preferred embodiment, said construct is as defined herein.

In a preferred embodiment a method is provided as defined herein wherein said modification of the lipid metabolism comprises enhancing the amount of triacylglycerol in said plant as compared to a control plant, and preferably comprises enhancing in said plant the amount of triacylglycerol derived from glycerol and fatty acids, wherein said fatty acids are selected from the group comprising long chain fatty acids (LCFA) comprising 13 to 18 carbon atoms and very long chain fatty acids (VLCFA) comprising more than 18 carbon atoms.

In certain embodiments of the methods of the invention, the step of providing a plant comprising a construct, said method comprises the step of:
    a) Introducing and expressing in said plant or a cell thereof a construct, wherein said construct comprises the following operably linked nucleic acid sequences: a promoter sequence, a nucleic acid encoding a TSPO polypeptide, and optionally a transcription terminator sequence, wherein said promoter sequence is a seed-specific promoter, which is active in seed tissue and during seed filling, and
    b) Cultivating said plant cell or said plant under conditions promoting plant growth and development.

Methods for Production of Transgenic Plants

The invention further provides a method for the production of transgenic plants having a modified lipid metabolism as compared to control plants.

A "transgenic plant" for the purposes of the invention is thus understood as meaning that the nucleic acids used in the methods of the invention are not present in, or originating from, the genome of said plant, or are present in the genome of said plant but not at their natural locus in the genome of said plant. However, "transgenic" also means that, while a nucleic acid according to the invention or used in the inventive methods is at its natural position in the genome of a plant, the nucleic acid has been modified with regard to the natural sequence and/or the genetic control sequence(s) of the natural sequence which is operably linked with said nucleic acid (e.g. promoter sequences) have been modified. Transgenic is preferably understood as meaning the expression of nucleic acids according to the invention at an unnatural locus in the genome. Preferred transgenic plants are mentioned herein.

According to the invention a method for the production of a plant, in particular a transgenic plant, having a modified lipid metabolism as compared to a control plant is provided which comprises the steps of:
    a) Introducing and expressing in said plant or a cell thereof a construct, wherein said construct comprises the following operably linked nucleic acid sequences: a promoter sequence, a nucleic acid encoding a TSPO polypeptide, and optionally a transcription terminator sequence, wherein said promoter sequence is a seed-specific promoter which is active in seed tissue and during seed filling, and
    b) Cultivating said plant cell or said plant under conditions promoting plant growth and development.

As indicated above, a construct comprising a nucleic acid encoding a TSPO as defined herein may be introduced directly into a plant cell or into the plant itself, including introduction into a tissue, organ or any other part of a plant. According to a preferred embodiment, a construct comprising a nucleic acid encoding a TSPO as defined herein is introduced into a plant by transformation.

Transformation of plant species is now a fairly routine technique. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed.

Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem).

The construct can be introduced stably or transiently into a parent host (plant) cell, using established techniques, including, but not limited to, electroporation, calcium phosphate precipitation, DEAE-dextran mediated transfection, liposome-mediated transfection, particle bombardment, *Agrobacterium*-mediated transformation, and the like. For stable transformation, a nucleic acid will generally further include a selectable marker, for example, any of several well-known selectable markers such as a fluorescent protein, gentamycin resistance, hygromycin resistance, kanamycin resistance, and the like.

Transgenic plants are preferably produced via *Agrobacterium*-mediated transformation. To that end, a construct as defined herein is preferably cloned into a binary vector, which is suitable for transforming *Agrobacterium tumefaciens*. Agrobacteria transformed by such a vector can then be used in known manner for the transformation of plants. The resulting transformed plant cell may then be used to regenerate a transformed plant in a manner known to persons skilled in the art, e.g. by growing in an appropriate medium to promote cell proliferation and regeneration, or generating transgenic seeds from transformed flower's bud (ovule) of a plant.

Preferably, said construct as applied in the plants, plant parts or methods as taught herein is a construct as defined herein.

Preferably, said nucleic acid encoding a TSPO polypeptide as applied in the plants, plant parts or methods as taught herein is a nucleic acid encoding a TSPO polypeptide is as defined herein.

Preferably, said promoter sequence as applied in the plants, plant parts or methods as taught herein is a seed-specific promoter as defined herein.

Preferably, said transcription terminator sequence as applied in the plants, plant parts or methods as taught herein is a transcription terminator sequence as defined herein.

The present invention clearly also extends to any plant cell or plant produced by any of the methods described herein, and to all plant parts and propagules thereof. The present invention encompasses plants or parts thereof, including seeds, obtainable by the methods according to the present invention.

The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention.

Methods for Making Products from Plants and Products

In another aspect, there is provided a method for producing a product, such as an oil or fat, in a plant comprising the steps of growing a plant as defined herein, and producing said product from or by said plant; or parts thereof, including seeds.

In particular, there is provided a method for producing a product in a plant comprising the steps of
  (i) Providing a plant as defined herein or a part thereof, and in particular a plant comprising a construct, wherein said construct comprises the following operably linked nucleic acid sequences: a) a promoter sequence, b) a nucleic acid encoding a TSPO polypeptide, and optionally c) a transcription terminator sequence, wherein said promoter sequence is a seed-specific promoter which is active in seed tissue and during seed filling; and wherein said construct confers a modified lipid metabolism to said plant, plant part or plant cell, as compared to a control plant, plant part or plant cell;
  (ii) Producing the product from or by the plant or a part thereof.

In certain embodiments a method for producing a product, such as an oil or fat, in a plant, and preferably for the production of a product having an enhanced amount of triacylglycerol as compared to a control product produced from or by a control plant, or part thereof is provided which comprises the steps of:
  i) Introducing and expressing in said plant or a cell thereof a construct, wherein said construct comprises the following operably linked nucleic acid sequences: a) a promoter sequence, b) a nucleic acid encoding a TSPO polypeptide, and preferably a TSPO polypeptide as defined herein, and optionally c) a transcription terminator sequence, wherein said promoter sequence is a seed-specific promoter which is active in seed tissues during seed filling, preferably a seed-specific promoter as defined herein,
  ii) Cultivating said plant cell or said plant under conditions promoting plant growth and development, and promoting the production of said product, and
  iii) collecting said product as produced from or by said plant or part thereof, including seeds.

In certain embodiments, a product, such as an oil or fat, produced from or by a plant, or part thereof, including seeds, according to the invention or product obtainable or obtained by a method of the invention is provided, wherein said product has enhanced amount of triacylglycerol as compared to a control product produced from or by a control plant, or part thereof.

Preferably, said plant as applied in the above-referenced method for producing a product, such as an oil or fat, is a plant as defined herein. Preferably, said construct as applied in the above-referenced method for producing a product, such as an oil or fat, in a plant is a construct as defined herein. Preferably, said nucleic acid encoding a TSPO polypeptide as applied in the above-referenced method for producing a product, such as an oil or fat, in a plant is a nucleic acid encoding a TSPO polypeptide is as defined herein. Preferably, said promoter sequence as applied in the above-referenced method for producing a product, such as an oil or fat, in a plant is a promoter sequence as defined herein. Preferably, said transcription terminator sequence as applied in the above-referenced method for producing a product, such as an oil or fat, in a plant is a transcription terminator sequence as defined herein.

The term "product" in this context intends to refer to a food, feed or industrial product derived from a plant, or parts thereof, and preferably refers to an oil or a fat, or isolated components thereof such as fatty acid or plant sterols.

The present invention clearly also extends to products such as an oil or a fat, as produced by any of the aforementioned methods or by or from any of the aforementioned plants, or parts thereof.

In one embodiment, the present invention refers to products, such as an oil or a fat, as obtainable or produced from or by a plant as defined herein, or part thereof, including seeds.

In another embodiment, the present invention refers to products, such as an oil or a fat, obtainable or obtained by any of the aforementioned methods as defined herein.

While the invention has been described in conjunction with specific embodiments thereof, it is evident that many alternatives, modifications, and variations will be apparent to those skilled in the art in light of the foregoing description. Accordingly, it is intended to embrace all such alternatives, modifications, and variations as follows in the spirit and broad scope of the appended claims.

The herein disclosed aspects and embodiments of the invention are further supported by the following non-limiting examples.

SEQUENCE LISTING

Throughout the description and examples, reference is made to the following sequences:
SEQ ID NO: 1: cDNA sequence of *Arabidopsis thaliana* TSPO (AtTSPO)
SEQ ID NO: 2: amino acid sequence of *Arabidopsis thaliana* TSPO (AtTSPO)
SEQ ID NO: 3: cDNA sequence of an *Arabidopsis thaliana* modified TSPO (H91A)
SEQ ID NO: 4: amino acid sequence of an *Arabidopsis thaliana* modified TSPO (H91A)
SEQ ID NO: 5: cDNA sequence of an *Arabidopsis thaliana* modified TSPO (H115A)
SEQ ID NO: 6: amino acid sequence of an *Arabidopsis thaliana* modified TSPO (H115A)
SEQ ID NO: 7: cDNA sequence of an *Arabidopsis thaliana* modified TSPO (H91A/H115A)
SEQ ID NO: 8: amino acid sequence of an *Arabidopsis thaliana* modified TSPO (H91A/H115A)
SEQ ID NO: 9: cDNA sequence of an *Arabidopsis thaliana* modified TSPO (C94W)
SEQ ID NO: 10: amino acid sequence of an *Arabidopsis thaliana* modified TSPO (C94W)
SEQ ID NO: 11: cDNA sequence of an *Arabidopsis thaliana* modified TSPO (Y122A)
SEQ ID NO: 12: amino acid sequence of an *Arabidopsis thaliana* modified TSPO (Y122A)
SEQ ID NO: 13: cDNA sequence of an *Arabidopsis thaliana* modified TSPO (Y124A)
SEQ ID NO: 14: amino acid sequence of an *Arabidopsis thaliana* modified TSPO (Y124A)
SEQ ID NO: 15: cDNA sequence of an *Arabidopsis thaliana* modified TSPO (Y122A/Y124A)
SEQ ID NO: 16: amino acid sequence of an *Arabidopsis thaliana* modified TSPO (Y122A/Y124A)
SEQ ID NO: 17: cDNA sequence of a *Brassica napus* TSPO
SEQ ID NO: 18: amino acid sequence of a *Brassica napus* TSPO
SEQ ID NO: 19: cDNA sequence of a *Brassica napus* TSPO
SEQ ID NO: 20: amino acid sequence of a *Brassica napus* TSPO
SEQ ID NO: 21: cDNA sequence of a *Brassica napus* TSPO
SEQ ID NO: 22: amino acid sequence of a *Brassica napus* TSPO
SEQ ID NO: 23: cDNA sequence of a *Brassica napus* TSPO
SEQ ID NO: 24: amino acid sequence of a *Brassica napus* TSPO
SEQ ID NO: 25: cDNA sequence of a *Brassica rapa* TSPO
SEQ ID NO: 26: amino acid sequence of a *Brassica rapa* TSPO
SEQ ID NO: 27: cDNA sequence of a *Brassica rapa* TSPO
SEQ ID NO: 28: amino acid sequence of a *Brassica rapa* TSPO
SEQ ID NO: 29: cDNA sequence of an *Oryza sativa* TSPO
SEQ ID NO: 30: amino acid sequence of an *Oryza sativa* TSPO
SEQ ID NO: 31: cDNA sequence of a *Camelina sativa* TSPO
SEQ ID NO: 32: amino acid sequence of a *Camelina sativa* TSPO
SEQ ID NO: 33: cDNA sequence of a *Linum usitatissimum* TSPO
SEQ ID NO: 34: amino acid sequence of a *Linum usitatissimum* TSPO
SEQ ID NO: 35: cDNA sequence of a *Zea mays* TSPO
SEQ ID NO: 36: amino acid sequence of a *Zea mays* TSPO
SEQ ID NO: 37: cDNA sequence of a *Helianthus annuus* TSPO
SEQ ID NO: 38: amino acid sequence of a *Helianthus annuus* TSPO
SEQ ID NO: 39: cDNA sequence of a *Helianthus annuus* TSPO
SEQ ID NO: 40: amino acid sequence of a *Helianthus annuus* TSPO
SEQ ID NO: 41: promoter sequence of an *Arabidopsis thaliana* TSPO
SEQ ID NO: 42: promoter sequence of a *Linum usitatissimum* TSPO
SEQ ID NO: 43: promoter sequence of a *Brassica napus* napin gene
SEQ ID NO: 44: promoter sequence of an *Arabidopsis thaliana* FAE1 gene
SEQ ID NO: 45: primer sequence SeM5'
SEQ ID NO: 46: primer sequence SeM3'
SEQ ID NO: 47: primer sequence NeM5'
SEQ ID NO: 48: primer sequence NeM3'
SEQ ID NO: 49: TSPO/MBR domain for AtTSPO
SEQ ID NO: 50: N-terminal domain for AtTSPO
SEQ ID NO: 51: Motif for AtTSPO

EXAMPLES

The following examples illustrate procedures for practicing the invention. The examples should not be construed as limiting.

Example 1

Example 1 illustrates the generation of TSPO-expressing homozygous transgenic *Arabidopsis* plants with high TAG content.

Cloning of *Arabidopsis* TSPO

An intronless *Arabidopsis* TSPO (AtTSPO) coding sequence was PCR amplified directly from *Arabidopsis* genomic DNA. The amplification was conducted using the primers SeM5' (aaatctagaaagcttaccatggattctcaggacatcag) (SEQ ID NO: 45) and SeM3' (aaa agatcttcacgcgactgcaagctttacattaac) (SEQ ID NO: 46) containing the underlined cloning restriction site XbaI and BglII, respectively. To that end, a freshly harvested *A. thaliana* leaf from 10-day-old seedling is transferred into an Eppendorf tube and homogenized at room temperature in 10 µl of 0.5 M NaOH, using a pestle. The mixture is centrifuged at 15000 rpm during 30 seconds at room temperature. Five µl of the supernatant is diluted with 45 µl of Tris-HCl buffer (100 mM, pH 8.0), and 1 µl of the diluted extract is used as PCR template. The amplicon can be obtained by combining the primers SeM5' and SeM3'.

The amplicon was cloned in the plasmid pPILY (NCBI Genbank accession #AY720433, version AY720433.1), opened with XbaI and BamHI.

For seed-specific expression, the double 35S CaMV promoter in pPILY was replaced by a truncated version of the *Brassica napus* napin promoter (corresponding to SEQ ID NO: 43). A freshly harvested *B. napus* leaf from 10-day-old greenhouse grown seedling was transferred into an Eppendorf tube and homogenized at room temperature in 10 µl of 0.5 M NaOH, using a pestle. The mixture was centrifuged at 15000 rpm during 30 seconds at room temperature. Five µl of the supernatant was diluted with 45 µl of Tris-HCl buffer (100 mM, pH 8.0), and 1 µl of the diluted extract was used as PCR template to amplify the napin promoter. The amplicon was obtained by combining the primers NeM5' (aaa ctccagggtacctaccttgttttaaaaagaatcgc) (SEQ ID NO: 47) and NeM3' (aaatctagagatttgcatggcgatcacgtg) (SEQ ID NO: 48) containing the underlined cloning site XhoI and XbaI, respectively.

The resulting plasmids were amplified in *Escherichia coli* strain DH5a using standard molecular biology techniques. An expression cassette with AtTSPO driven by the above-indicated seed-specific napin promoter was retrieved from pPILY by KpnI digestion and subcloned into the binary vector pCambia 1300 (product ID: M1591, Marker Gene Technologies, Inc.). The amplified binary plasmids in *E. coli* were checked for the orientation of the expression cassette by restriction digestion with HindIII and EcoRI/XbaI. The correct oriented clones were further verified by sequencing of the AtTSPO coding sequence. Two independent clones were mobilized in *Agrobacterium tumefaciens* strain GV3101::pMP90 (Koncz and Schnell, 1986, Molecular General Genetics 204: 383-396) by electroporation and the transformed clones selected on yeast extract broth supplemented with 100 µg/ml of kanamycin.

*Arabidopsis* Genetic Transformation and Expression of AtTSPO

Soil grown wild type *Arabidopsis* (Columbia 0; Col0) plants were genetically transformed by the "floral diping" method as modified by Clough (1998, Plant Journal, 16: 735-743). Transgenic T1 seeds were selected on half strength Murashige and Skoog (MS/2) medium (Murashige and Skoog, 1962, Physiol. Plant. 15: 473-497), supplemented with 20 µg/ml hygromycin. Resistant plants were transferred to soil and after selfing, the T2 seeds were screened as the T1 seeds for hygromycin resistance. Lines segregating in a 3:1 (resistant:sensitive) ratio on hygromycin, indicative of potential homozygote in the offspring were used for subsequent analyses. T3 homozygote plants grown under normal growth conditions were tested for AtTSPO expression in vegetative tissues by western blotting (Guillaumot et al., 2009, Plant Journal, 60: 242-256). Seeds from confirmed T3 homozygote transgenic lines and their offspring were used for lipid analyses. For the analyses, 2-4 independent lines were used and 10-20 mg of seeds were used, which correspond to 200-500 seeds per assay/replica.

Lipids Extraction and Analysis

Seeds were imbibed (or not) at 22° C. under continuous light in the presence or absence of radiolabeled acetate (2 pCi/assay). After 24 h of imbibition, the seeds were heated to 70° C. in isopropanol for 15 min to inactivate lipases and ground using an Ultra-Turrax homogenizer. Lipids were extracted three times with chloroform:methanol (1:1, v/v) at room temperature, and then washed three times with 0.9% NaCl. The solvent was evaporated under $N_2$ and lipids were dissolved in an appropriate volume of chloroform:methanol (1:1, v/v). Polar lipids were separated by HPTLC (60F254 plates, Merck, Darmstadt, Germany), using the solvent system methyl acetate:n-propanol:chloroform:methanol: 0.25% aqueous KCl (25:25:25:10:9, v/v) (Heape et al. 1985, J Chromatogr. April 5; 322(2):391-5), and neutral lipids were separated by HPTLC using the solvent system hexane:ethylether:acetic acid (90:15:2, v/v) (Laloi et al., 2007, Plant Physiol. January; 143(1):461-72). Lipids were identified by co-migration with known standards and quantified by densitometric analysis (Macala et al., 1983, J Lipid Res. September; 24(9):1243-50) using a TLC scanner 3 (CAMAG, Muttenz, Switzerland) after primuline staining (van Echten-Deckert, 2000, Methods Enzymol. 312:64-79). For more precise quantification, individual lipids were scraped off the HPTLC plates and their fatty acids were identified and quantified by gas chromatography after conversion to their corresponding methyl esters using hot methanolic $H_2SO_4$ according to Browse et al. (1986, Anal. Biochem 152:141-145). Fatty acids were quantified relative to a C17 internal standard. When required, radio-labeled acetate was added to the imbibating seeds. Radio-labeled lipids were separated by HPTLC and analyzed using a Storm Phosphorlmager (GE Healthcare) and ImageQuant software (Applied Biosystems).

Results

Figures 2, 3:
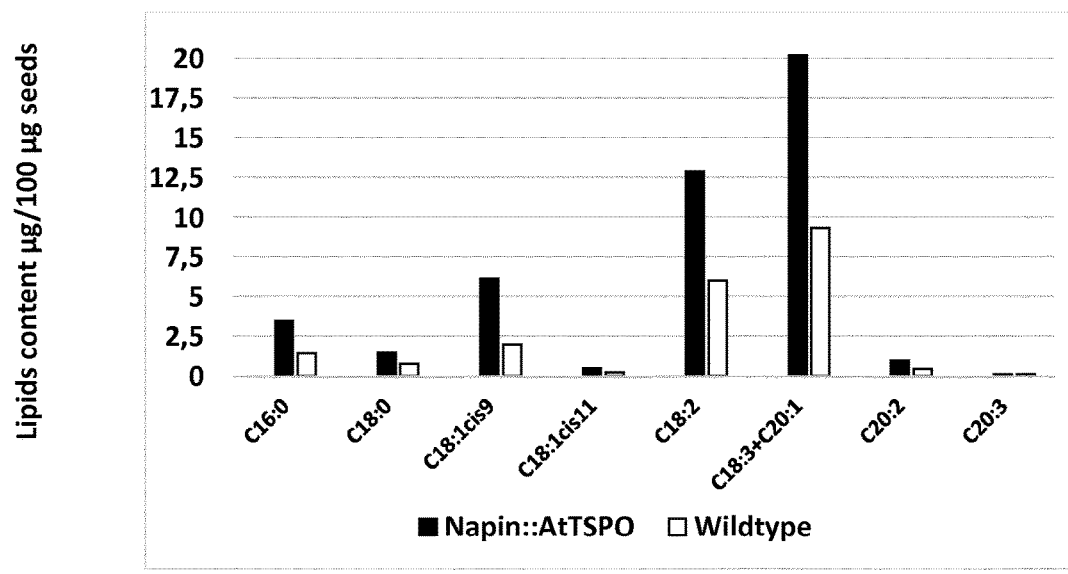
FIG. 2 illustrates relative fatty acids composition (percentage of total mass in µg fatty acid/100 µg seeds) of transgenic *Arabidopsis* dry seeds expressing an *Arabidopsis* TSPO gene driven by a seed-specific napin promoter (Napin::TSPO), as compared to wild type seeds (wildtype).
FIG. 3 illustrates the amino acid sequence of a TSPO polypeptide from *Arabidopsis thaliana*, corresponding to SEQ ID NO: 2, highlighting the plant-specific N-terminal extension (in italics and underlined), and potential target sites for generating point mutational variants of the sequence (amino acids indicated in bold, underlined and italics). The TspO/MBR domain from the illustrated amino acid sequence extends from amino acid 52 to 195. A conserved (plant-specific) domain extends from amino acid 42 to 50.

Results are represented in FIGS. 1 and 2. The results show that transformed lines expressing the *Arabidopsis* TSPO polypeptide represented by SEQ ID NO: 2 under the control of the seed-specific napin promoter represented by SEQ ID NO: 43 in the T3 generation had higher overall TAG content in seeds than that of corresponding non-transformed plants on a dry seed weight basis (FIG. 1). FIG. 2 illustrates amounts of different specific TAG in the analyzed seeds of the transgenic *Arabidopsis* lines as compared to wild type *Arabidopsis* lines.

The inventors have found that a seed-specific expression in a plant of a nucleic acid encoding a TSPO during the seed filling stage permits to increase the TAG content in plants without any obvious deleterious effect on growth or yield. It has further been shown by the inventors that the amount of nutritionally important fatty acids in oil used in the food industry, for instance palmitic, stearic, oleic, linoleic, and α-linolenic acids, increased individually up to 2-fold in modified plants expressing a TSPO in a seed-specific manner, as compared to control (non-modified) plants.

Example 2

Alignment of TSPO polypeptide sequences was performed using the MUSCLE (version 3.8, May 2010) (MUltiple Sequence Comparison by Log-Expectation) and ClustalW output (ClustalW alignment format without base/residue numbering). The analysis was performed using the default parameters of MUSCLE as specified at http://www.ebi.ac.uk/Tools/msa/muscle/. The polypeptides are aligned in FIG. 4. The single letter code for amino acids is used. These alignments can be used for defining further motifs or consensus sequences, when using conserved amino acids, i.e. those identical in the aligned sequences and/or those highly conserved. The sequences in FIG. 4 were identified by their short name. Table B provides the details for each sequence.

TABLE B sequences shown in FIG. 4

| | organism | Amino acid sequence (SEQ ID NO:) |
|---|---|---|
| OsTSPO | Oryza sativa | 30 |
| LuTSPO | Linum usitatissimum | 34 |
| BnTSPO3 | Brassica napus | 22 |
| BnTSPO1 | Brassica napus | 18 |
| BrTSPO1 | Brassica rapa | 26 |
| BnTSPO2 | Brassica napus | 20 |
| BnTSPO4 | Brassica napus | 24 |
| BrTSPO2 | Brassica rapa | 28 |
| AtTSPO | Arabidopsis thaliana | 2 |
| CsTSPO | Camelina sativa | 32 |

Example 3

Example 3 illustrates the generation of TSPO-expressing transgenic Camelina sativa plants with high TAG content. Camelina sativa is an oil-producing plant from the family of the Brassicaceae, and is also generally known as Camelina, gold-of-pleasure, false flax, or linseed dodder.

Constructs

Three different constructs, and thus three different promoter-TSPO gene combinations, were evaluated in vivo in Camelina sativa plants. In each of the constructs the seed-specific promoter from the Arabidopsis Fatty Acid Elongase (FAE1) gene (SEQ ID NO: 44) was used to drive the expression of a plant TSPO gene. The TSPO gene encoding a TSPO protein was selected from either Arabidopsis thaliana (AtTSPO: SEQ ID NO: 2), or Camelina sativa (CsTSPO: SEQ ID NO: 32), or Linum usitatissimum (LuTSPO: SEQ ID NO: 34). In each of the constructs a Nopaline synthase terminator sequence (as disclosed in Dymock et al., Plant Mol. Biol. (1991), 17: 711-725) was used as transcription terminator sequence.

The constructs designed as indicated above were synthetized (GeneScript, USA) flanked at both end by the restriction site I-SCEI and cloned into pUC57 (GeneScript). Amplified pUC57 in E. coli were digested with I-SCEI to retrieve each of the constructs and subcloned into pMODUL opened using the same enzyme. The clones were checked by restriction digests then transferred into Agrobacterium tumefaciens strain GV3101::pMP90 (Koncz and Schnell, 1986, Molecular General Genetics 204: 383-396).

Camelina Transformation and Seed-Specific Expression of TSPO

Camelina sativa plants were grown in the greenhouse in individual pots up to the flowering stage. An overnight grown liquid culture of A. tumefaciens harboring the desired genetic construct in YEB medium supplemented with the appropriate antibiotics was used to prepare the inoculum. The cells were pelleted by centrifugation at 3500 g and re-suspended in buffer containing 10 mM $MgSO_4$, 10 mM MES (pH 5.5), 200 µM acetosyringone (freshly prepared). The re-suspended bacteria were allowed to incubate in the buffer for two hours at room temperature. Opened flowers were manually stripped from the C. sativa plants using forceps. The bacteria were injected into individual flower buds using a syringe fitted with a 21Gx1" needle. This was repeated a week later for arising new flower buds. The transformed plants were allowed to generate seeds. The dry seeds were selected on agar plate containing half strength Murashige and Skoog medium and hygromycin (20 µg/ml). Potential hygromycin resistant plants were further genotyped for the presence of the TSPO transgene and allowed to self in the green house. For lipid analysis, dry seeds were harvested from plants grown at the same time. The extraction of lipids from harvested seeds and analyses were conducted in a same way as described for the Arabidopsis seeds (see Example 1).

Results

Figure 5:
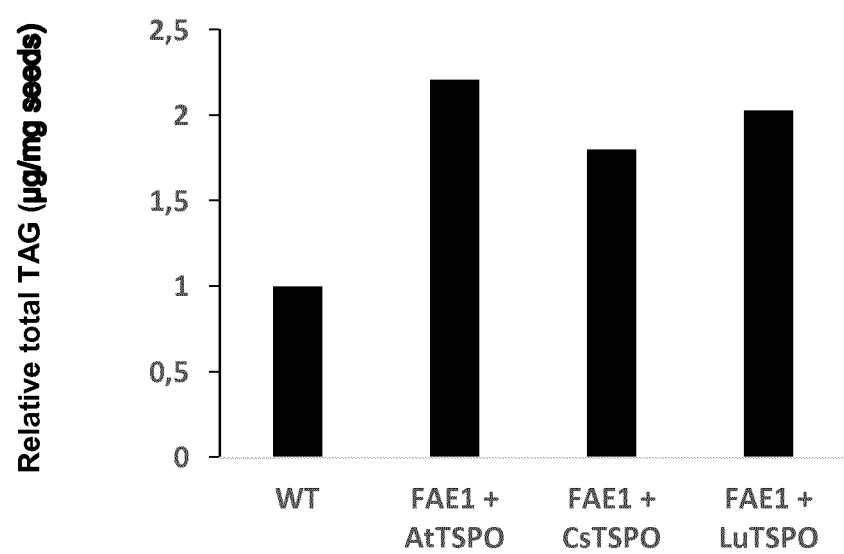
FIG. 5 represents the relative comparison of total amount of TAG (μg/mg seeds) observed in transgenic Camelina sativa lines and seeds thereof that were transformed with a construct comprising a TSPO gene under the control of a seed-specific FAE1 promoter from Arabidopsis. WT refers to wild-type Camelina sativa seeds; FAE1+AtTSPO refers to transgenic seeds expressing the Arabidopsis thaliana TSPO; FAE1+CsTSPO refers to transgenic seeds expressing the Camelina sativa TSPO; FAE1+LuTSPO refers to transgenic seeds expressing the Linum usitatissimum TSPO. Values are means from three independent transgenic lines obtained from each genetic construct.

Results are represented in FIG. 5, wherein a relative comparison of total TAG as compared to wild-type plants (WT=set at value 1) is shown. Values are means from three independent transgenic lines obtained from each genetic construct. The results show that transformed lines expressing the Arabidopsis TSPO polypeptide under the control of the seed-specific FAE1 promoter had higher overall TAG content in seeds than that of corresponding non-transformed plants. A same observation is made for lines expressing a Camelina sativa or Linum usitatissimum TSPO under the control of said seed-specific FAE1 promoter.

TABLE C illustrates amounts of different specific fatty acids in the analyzed seeds of the transgenic Camelina sativa lines as compared to wild type Camelina sativa lines for the three evaluated constructs.

| | WT | FAE1 + AtTSPO | FAE1 + CsTSPO | FAE1 + LuTSPO |
|---|---|---|---|---|
| C16:0 | 1 | 1.72 | 1.46 | 1.66 |
| C18:0 | 1 | 1.93 | 1.75 | 1.84 |
| C18:1n9 | 1 | 1.85 | 1.71 | 1.88 |
| C18:2n6 | 1 | 1.92 | 1.52 | 1.92 |
| C18:3n3 | 1 | 2.99 | 2.62 | 2.6 |
| C20:0 | 1 | 1.9 | 1.6 | 1.78 |
| C20:1n9 | 1 | 2.44 | 1.95 | 2.25 |
| C20:2n6 | 1 | 2.88 | 1.97 | 2.53 |
| C20:3n3 | 1 | 3.57 | 2.97 | 2.86 |
| C22:0 | 1 | 1.64 | 1.27 | 1.52 |
| C22:1n9 | 1 | 2.32 | 1.66 | 2.15 |
| C22:3n3 | 1 | 4.02 | 3.44 | 3.59 |
| C24:0 | 1 | 1.21 | 1.06 | 1.23 |
| C24:1n9 | 1 | 2 | 1.54 | 1.93 |
| C24:2n6 | 1 | 1.46 | 1.25 | 1.46 |

The amounts in TABLE C are represented as the relative fold increase in specific fatty acids as compared to what is obtained in wild-type plants. The relative quantity of each fatty acid (µg/mg seeds) was normalized against the wild-type seeds (WT) level (value set at 1). It can in particular be observed that for certain polyunsaturated omega-3 fatty acids, and in particular C18:3n3, C20:3n3, and C22:3n3, a 2.5 to 4-fold increase was obtained in the transgenic lines. The values are average of three independent transgenic lines as represented in FIG. 5.

Example 4

TSPO-expressing transgenic Arabidopsis thaliana plants with high TAG content are obtained by transforming Arabidopsis plants is a same manner as discussed in Example 1 with the three constructs described in Example 3. Primary transformants (T1) are generated and seeds can undergo segregation for the selection of homozygote lines. TAG content is analysed in the T2 seed as described above and compared to that of wild-type/non-transformed plants. Also independent homozygote lines obtained from the transformation events are further analyzed for TAG content as described above.

Overall, from the above it can be concluded that seed-specific expression in a plant of a nucleic acid encoding a TSPO during the seed filling stage permits to increase the TAG content in plants without any obvious deleterious effect on growth or yield. This has been illustrated in different plants (*Arabidopsis*, *Camelina*), for different seed-specific promoters (napin, FAE1), when applying different TSPO genes (from *Arabidopsis*, *Camelina* or *Linum*).

It has further been shown that the amount of nutritionally important fatty acids in oil used in the food industry, for instance palmitic, stearic, oleic, linoleic, and α-linolenic acids, increased individually up to about 2-fold or more in modified plants expressing a TSPO in a seed-specific manner, as compared to control (non-modified) plants. Hence, the present results indicate that the level of certain important fatty acids can be significantly increased when the TSPO gene is expressed under a seed-specific promoter which is active during seed filling stage. Surprisingly this is not the stage at which a naturally occurring (endogenous) TSPO gene is induced in a plant and there is no indication in the prior art for such specific effect.

The invention claimed is:

1. A method for increasing the lipid production in a plant seed as compared to a control plant comprising the step of providing a plant comprising a construct comprising the following operably linked nucleic acid sequences:
   a) a nucleic acid encoding a translocator (TSPO) polypeptide wherein said polypeptide comprises a tryptophan-rich sensory protein/peripheral-type benzodiazepine receptor domain (TspO/MBR domain) having at least 93% sequence identity to SEQ ID NO: 49, and wherein said TSPO polypeptide is represented by SEQ ID NO: 2, or a homologue thereof having at least 90% sequence identity to SEQ ID NO: 2,
   b) one or more control sequences capable of driving expression of the nucleic acid of a); and optionally
   c) one or more transcription terminator sequences,
   wherein at least one of said control sequences is a seed-specific promoter which is active in seed tissues during seed filling, and wherein said promoter sequence is not a naturally occurring TSPO promoter wherein the seed-specific promoter is selected from the group consisting of a napin promoter, a fatty acid elongase 1 (FAE1) promoter, an oleosin promoter and a TSPO promoter that has been modified in order to confer seed-specific expression during the period of lipid biosynthesis during said seed filling, and
   wherein lipid production in a plant seed is increased as compared to the seed of a control plant.

2. A method for the production of a plant having an increased lipid production in a plant seed as compared to a control plant, which method comprises the steps of:
   (i) introducing and expressing in said plant or a cell the following operably linked nucleic acid sequences:
      a) a nucleic acid encoding a translocator (TSPO) polypeptide wherein said polypeptide comprises a tryptophan-rich sensory protein/peripheral-type benzodiazepine receptor domain (TspO/MBR domain) having at least 93% sequence identity to SEQ ID NO: 49, and wherein said TSPO polypeptide is represented by SEQ ID NO: 2, or a homologue thereof having at least 90% sequence identity to SEQ ID NO: 2,
      b) one or more control sequences capable of driving expression of the nucleic acid of a); and optionally
      c) one or more transcription terminator sequences,
      wherein at least one of said control sequences is a seed-specific promoter which is active in seed tissues during seed filling, and wherein said promoter sequence is not a naturally occurring TSPO promoter, and wherein the seed-specific promoter is selected from the group consisting of a napin promoter, a fatty acid elongase 1 (FAE1) promoter, an oleosin promoter and a TSPO promoter that has been modified in order to confer seed-specific expression during the period of lipid biosynthesis during said seed filling, and
   (ii) cultivating said plant cell or said plant under conditions promoting plant growth and development; and wherein a plant having an increased lipid production in a plant seed is produced as compared to the seed of a control plant.

3. The method according to claim 2, wherein the increased lipid production comprises an enhanced amount of triacylglycerol in said plant seed as compared to the seed of a control plant, wherein the enhanced amount of triacylglycerol is derived from glycerol and fatty acids, wherein said fatty acids are selected from the group consisting of long chain fatty acids (LCFA) comprising 13 to 18 carbon atoms and very long chain fatty acids (VLCFA) comprising more than 18 carbon atoms.

4. A method for producing an oil or fat in a plant seed comprising the steps of producing a plant according to claim 2, and producing said oil or fat from or by said plant seed by grinding the seed and extracting the lipids.

5. A construct for increasing the lipid production in a plant seed, wherein said construct comprises a nucleic acid encoding a TSPO polypeptide comprising
   a) a tryptophan-rich sensory protein/peripheral-type benzodiazepine receptor domain (TspO/MBR domain) having at least 93% sequence identity to SEQ ID NO: 49, and wherein said TSPO polypeptide has at least 90% sequence identity to SEQ ID NO 2
   b) one or more control sequences capable of driving expression of the nucleic acid of a); and optionally
   c) one or more transcription terminator sequences,
   wherein at least one of said control sequences is a seed-specific promoter which is active in seed tissues during seed filling, and wherein said promoter sequence is not a naturally occurring TSPO promoter, and wherein the seed-specific promoter is selected from the group consisting of a napin promoter, a fatty acid elongase 1 (FAE1) promoter, an oleosin promoter and a TSPO promoter that has been modified in order to confer seed-specific expression during the period of lipid biosynthesis during said seed filling.

6. The construct according to claim 5, wherein said nucleic acid encoding said TSPO polypeptide is represented by SEQ ID NO: 2, or a homologue thereof having at least 95% sequence identity to SEQ ID NO: 2.

7. The method for increasing the lipid production in a plant seed as compared to a control plant according to claim 1 which method further comprises the steps of:
   (i) expressing in said plant or a cell the operably linked nucleic acid sequences as defined in claim 1, and
   (ii) cultivating said plant cell or said plant under conditions promoting plant growth and development.

8. The method according to claim 1, wherein the increased lipid production comprises an enhanced amount of triacylglycerol in said plant seed as compared to the seed of a control plant, wherein the enhanced amount of triacylglycerol is derived from glycerol and fatty acids, wherein said fatty acids are selected from the group consisting of long chain fatty acids (LCFA) comprising 13 to 18 carbon atoms and very long chain fatty acids (VLCFA) comprising more than 18 carbon atoms.

9. The method according to claim 1, wherein the seed-specific promoter is a napin promoter having a polynucleotide sequence of SEQ ID NO: 43 or a polynucleotide sequence having at least 95% sequence identity to SEQ ID NO: 43.

10. The method according to claim 1, wherein the seed-specific promoter is a FAE1 promoter having a polynucleotide sequence of SEQ ID NO: 44 or a polynucleotide sequence having at least 95% sequence identity to SEQ ID NO: 44.

11. The method according to claim 1, wherein the modified TSPO promoter is derived from a TSPO promoter from *Arabidopsis* having SEQ ID NO: 41, or a functional fragment thereof.

12. The method according to claim 1, wherein the modified TSPO promoter is derived from a TSPO promoter from *Linum usitatissimum* having SEQ ID NO: 42, or a functional fragment thereof.

13. The method according to claim 1, wherein nucleic acid encoding said TSPO polypeptide is represented by SEQ ID NO: 2, or a homologue thereof having at least 93% sequence identity to SEQ ID NO: 2.

14. The method according to claim 1, wherein said nucleic acid encoding said TSPO polypeptide is represented by SEQ ID NO: 32, or a homologue thereof having at least 93% sequence identity to SEQ ID NO: 32.

15. The method according to claim 2, wherein the seed-specific promoter is a napin promoter having a polynucleotide sequence of SEQ ID NO: 43 or a polynucleotide sequence having at least 95% sequence identity to SEQ ID NO: 43.

16. The method according to claim 2, wherein the seed-specific promoter is a FAE1 promoter having a polynucleotide sequence of SEQ ID NO: 44 or a polynucleotide sequence having at least 95% sequence identity to SEQ ID NO: 44.

17. The method according to claim 2, wherein the modified TSPO promoter is derived from a TSPO promoter from *Arabidopsis* having SEQ ID NO: 41, or a functional fragment thereof.

18. The method according to claim 2, wherein the modified TSPO promoter is derived from a TSPO promoter from *Linum usitatissimum* having SEQ ID NO: 42, or a functional fragment thereof.

19. The method according to claim 2, wherein nucleic acid encoding said TSPO polypeptide is represented by SEQ ID NO: 2, or a homologue thereof having at least 93% sequence identity to SEQ ID NO: 2.

20. The method according to claim 2, wherein said nucleic acid encoding said TSPO polypeptide is represented by SEQ ID NO: 32, or a homologue thereof having at least 93% sequence identity to SEQ ID NO: 32.

21. The construct according to claim 5, wherein the seed-specific promoter is a napin promoter having a polynucleotide sequence of SEQ ID NO: 43 or a polynucleotide sequence having at least 95% sequence identity to SEQ ID NO: 43.

22. The construct according to claim 5, wherein the seed-specific promoter is a FAE1 promoter having a polynucleotide sequence of SEQ ID NO: 44 or a polynucleotide sequence having at least 95% sequence identity to SEQ ID NO: 44.

23. The construct according to claim 5, wherein the modified TSPO promoter is derived from a TSPO promoter from *Arabidopsis* having SEQ ID NO: 41, or a functional fragment thereof.

24. The construct according to claim 5, wherein the modified TSPO promoter is derived from a TSPO promoter from *Linum usitatissimum* having SEQ ID NO: 42, or a functional fragment thereof.

25. The construct according to claim 5, wherein nucleic acid encoding said TSPO polypeptide is represented by SEQ ID NO: 2, or a homologue thereof having at least 93% sequence identity to SEQ ID NO: 2.

26. The construct according to claim 5, wherein said nucleic acid encoding said TSPO polypeptide is represented by SEQ ID NO: 32, or a homologue thereof having at least 93% sequence identity to SEQ ID NO: 32.

* * * * *

SEQUENCE LISTING

```
<160> NUMBER OF SEQ ID NOS: 51

<210> SEQ ID NO 1
<211> LENGTH: 591
<212> TYPE: DNA
<213> ORGANISM: Arabidopsis thaliana

<400> SEQUENCE: 1
atggattctc aggacatcag ataccgcggc ggagacgaca gagacgctgc aacgacggct      60
atggccgaga cagagaggaa aagcgctgac gacaacaaag gaaaacgcga tcaaaagagg     120
gcgatggcga aacgtggtct caagtctctg acggtagcgg ttgcggctcc tgtgctcgtg     180
acgctcttcg ctacgtattt cctcggcaca agcgacggat acgggaatcg agctaagtcc     240
tcgtcgtgga tcccacctct gtggctccta cacacaacgt gtctcgcttc tagtggtctg     300
atgggtttgg ctgcgtggct tgtatgggtt gacggtggct tccacaagaa gcccaatgct     360
ctgtatcttt acttagctca gtttttgctc tgtttggttt gggatccggt tacgttccgc     420
gtcgggtcgg gagtagcggg gcttgcggtg tggttgggtc aatcggctgc gttattcgga     480
tgctacaagg ccttta atga gataagtccg gtcgctggta atctggtaaa gccgtgtttg     540
gcttgggctg cctttgtagc cgctgttaat gtaaagcttg cagtcgcgtg a              591

<210> SEQ ID NO 2
<211> LENGTH: 196
<212> TYPE: PRT
<213> ORGANISM: Arabidopsis thaliana

<400> SEQUENCE: 2

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Ala Pro Val Leu Val Thr Leu Phe Ala
    50                  55                  60

Thr Tyr Phe Leu Gly Thr Ser Asp Gly Tyr Gly Asn Arg Ala Lys Ser
65                  70                  75                  80

Ser Ser Trp Ile Pro Pro Leu Trp Leu Leu His Thr Thr Cys Leu Ala
            85                  90                  95

Ser Ser Gly Leu Met Gly Leu Ala Ala Trp Leu Val Trp Val Asp Gly
            100                 105                 110

Gly Phe His Lys Lys Pro Asn Ala Leu Tyr Leu Tyr Leu Ala Gln Phe
        115                 120                 125

Leu Leu Cys Leu Val Trp Asp Pro Val Thr Phe Arg Val Gly Ser Gly
    130                 135                 140
```

```
Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
            165                 170                 175

Lys Pro Cys Leu Ala Trp Ala Ala Phe Val Ala Ala Val Asn Val Lys
            180                 185                 190

Leu Ala Val Ala
        195

<210> SEQ ID NO 3
<211> LENGTH: 591
<212> TYPE: DNA
<213> ORGANISM: Arabidopsis thaliana

<400> SEQUENCE: 3
atggattctc aggacatcag ataccgcggc ggagacgaca gagacgctgc aacgacggct      60
atggccgaga cagagaggaa aagcgctgac gacaacaaag gaaaacgcga tcaaaagagg     120
gcgatggcga aacgtggtct caagtctctg acggtagcgg ttgcggctcc tgtgctcgtg     180
acgctcttcg ctacgtattt cctcggcaca agcgacggat acgggaatcg agctaagtcc     240
tcgtcgtgga tcccacctct gtggctccta gcaacaacgt gtctcgcttc tagtggtctg     300
atgggtttgg ctgcgtggct tgtatgggtt gacggtggct tccacaagaa gcccaatgct     360
ctgtatcttt acttagctca gttttttgctc tgtttggttt gggatccggt tacgttccgc     420
gtcgggtcgg gagtagcggg gcttgcggtg tggttgggtc aatcggctgc gttattcgga     480
tgctacaagg cctttaatga gataagtccg gtcgctggta atctggtaaa gccgtgtttg     540
gcttgggctg cctttgtagc cgctgttaat gtaaagcttg cagtcgcgtg a              591

<210> SEQ ID NO 4
<211> LENGTH: 196
<212> TYPE: PRT
<213> ORGANISM: Arabidopsis thaliana

<400> SEQUENCE: 4

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Ala Pro Val Leu Val Thr Leu Phe Ala
    50                  55                  60

Thr Tyr Phe Leu Gly Thr Ser Asp Gly Tyr Gly Asn Arg Ala Lys Ser
65                  70                  75                  80

Ser Ser Trp Ile Pro Pro Leu Trp Leu Leu Ala Thr Thr Cys Leu Ala
                85                  90                  95

Ser Ser Gly Leu Met Gly Leu Ala Ala Trp Leu Val Trp Val Asp Gly
            100                 105                 110

Gly Phe His Lys Lys Pro Asn Ala Leu Tyr Leu Tyr Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160
```

```
Cys Tyr Lys Ala Phe Asn Glu Ile Ser Pro Val Ala Gly Asn Leu Val
                165                 170                 175

Lys Pro Cys Leu Ala Trp Ala Ala Phe Val Ala Val Asn Val Lys
        180                 185                 190

Leu Ala Val Ala
        195

<210> SEQ ID NO 5
<211> LENGTH: 591
<212> TYPE: DNA
<213> ORGANISM: Arabidopsis thaliana

<400> SEQUENCE: 5
atggattctc aggacatcag ataccgcggc ggagacgaca gagacgctgc aacgacggct      60
atggccgaga cagagaggaa aagcgctgac gacaacaaag gaaaacgcga tcaaaagagg     120
gcgatggcga aacgtggtct caagtctctg acggtagcgg ttgcggctcc tgtgctcgtg     180
acgctcttcg ctacgtattt cctcggcaca agcgacggat acgggaatcg agctaagtcc     240
tcgtcgtgga tcccacctct gtggctccta gcaacaacgt gtctcgcttc tagtggtctg     300
atgggtttgg ctgcgtggct tgtatgggtt gacggtggct cgcaaagaa gcccaatgct      360 ctgtatcttt acttagctca gttttgctc tgtttggttt gggatccggt tacgttccgc      420
gtcgggtcgg gagtagcggg gcttgcggtg tggttgggtc aatcggctgc gttattcgga     480
tgctacaagg cctttaatga gataagtccg gtcgctggta atctggtaaa gccgtgtttg     540
gcttgggctg cctttgtagc cgctgttaat gtaaagcttg cagtcgcgtg a              591

<210> SEQ ID NO 6
<211> LENGTH: 196
<212> TYPE: PRT
<213> ORGANISM: Arabidopsis thaliana

<400> SEQUENCE: 6

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Ala Pro Val Leu Val Thr Leu Phe Ala
    50                  55                  60

Thr Tyr Phe Leu Gly Thr Ser Asp Gly Tyr Gly Asn Arg Ala Lys Ser
65                  70                  75                  80

Ser Ser Trp Ile Pro Pro Leu Trp Leu Leu His Thr Thr Cys Leu Ala
                85                  90                  95

Ser Ser Gly Leu Met Gly Leu Ala Ala Trp Leu Val Trp Val Asp Gly
            100                 105                 110

Gly Phe Ala Lys Lys Pro Asn Ala Leu Tyr Leu Tyr Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175
```

Lys Pro Cys Leu Ala Trp Ala Ala Phe Val Ala Ala Val Asn Val Lys
            180                 185                 190

Leu Ala Val Ala
        195

<210> SEQ ID NO 7
<211> LENGTH: 591
<212> TYPE: DNA
<213> ORGANISM: Arabidopsis thaliana

<400> SEQUENCE: 7
atggattctc aggacatcag ataccgcggc ggagacgaca gagacgctgc aacgacggct      60
atggccgaga cagagaggaa aagcgctgac gacaacaaag gaaaacgcga tcaaagaggg     120
gcgatggcga acgtggtct caagtctctg acggtagcgg ttgcggctcc tgtgctcgtg      180
acgctcttcg ctacgtattt cctcggcaca agcgacggat acgggaatcg agctaagtcc     240
tcgtcgtgga tcccacctct gtggctccta gcaacaacgt gtctcgcttc tagtggtctg     300
atgggtttgg ctgcgtggct tgtatgggtt gacggtggct cgcaaagaa gcccaatgct      360 ctgtatcttt acttagctca gttttttgctc tgtttggttt gggatccggt tacgttccgc    420
gtcgggtcgg gagtagcggg gcttgcggtg tggttgggtc aatcggctgc gttattcgga    480
tgctacaagg cctttaatga gataagtccg gtcgctggta atctggtaaa gccgtgtttg    540
gcttgggctg cctttgtagc cgctgttaat gtaaagcttg cagtcgcgtg a             591

<210> SEQ ID NO 8
<211> LENGTH: 196
<212> TYPE: PRT
<213> ORGANISM: Arabidopsis thaliana

<400> SEQUENCE: 8

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Pro Val Leu Val Thr Leu Phe Ala
    50                  55                  60

Thr Tyr Phe Leu Gly Thr Ser Asp Gly Tyr Gly Asn Arg Ala Lys Ser
65                  70                  75                  80

Ser Ser Trp Ile Pro Pro Leu Trp Leu Ala Thr Thr Cys Leu Ala
                85                  90                  95

Ser Ser Gly Leu Met Gly Leu Ala Ala Trp Leu Val Trp Val Asp Gly
            100                 105                 110

Gly Phe Ala Lys Lys Pro Asn Ala Leu Tyr Leu Tyr Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175

Lys Pro Cys Leu Ala Trp Ala Ala Phe Val Ala Ala Val Asn Val Lys
            180                 185                 190

Leu Ala Val Ala
        195

<210> SEQ ID NO 9
<211> LENGTH: 591
<212> TYPE: DNA
<213> ORGANISM: Arabidopsis thaliana

<400> SEQUENCE: 9
atggattctc aggacatcag ataccgcggc ggagacgaca gagacgctgc aacgacggct    60
atggccgaga cagagaggaa agcgctgac gacaacaaag gaaaacgcga tcaaaagagg    120
gcgatggcga acgtggtct caagtctctg acggtagcgg ttgcggctcc tgtgctcgtg    180
acgctcttcg ctacgtattt cctcggcaca agcgacggat acgggaatcg agctaagtcc    240
tcgtcgtgga tcccacctct gtggctccta cacacaacgt ggctcgcttc tagtggtctg    300 atgggttttgg ctgcgtggct tgtatgggtt gacggtggct ccacaagaa gcccaatgct    360 ctgtatcttt acttagctca gttttttgctc tgtttggttt gggatccggt tacgttccgc    420
gtcgggtcgg gagtagcggg gcttgcggtg tggttgggtc aatcggctgc gttattcgga    480
tgctacaagg cctttaatga gataagtccg gtcgctggta atctggtaaa gccgtgtttg    540
gcttgggctg cctttgtagc cgctgttaat gtaaagcttg cagtcgcgtg a    591

<210> SEQ ID NO 10
<211> LENGTH: 196
<212> TYPE: PRT
<213> ORGANISM: Arabidopsis thaliana

<400> SEQUENCE: 10

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Pro Val Leu Val Thr Leu Phe Ala
    50                  55                  60

Thr Tyr Phe Leu Gly Thr Ser Asp Gly Tyr Gly Asn Arg Ala Lys Ser
65              70                  75                  80

Ser Ser Trp Ile Pro Pro Leu Trp Leu His Thr Thr Trp Leu Ala
            85                  90                  95

Ser Ser Gly Leu Met Gly Leu Ala Ala Trp Leu Val Trp Val Asp Gly
            100                 105                 110

Gly Phe His Lys Lys Pro Asn Ala Leu Tyr Leu Tyr Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
            165                 170                 175

Lys Pro Cys Leu Ala Trp Ala Ala Phe Val Ala Val Asn Val Lys
            180                 185                 190

Leu Ala Val Ala
        195

<210> SEQ ID NO 11
<211> LENGTH: 591
<212> TYPE: DNA
<213> ORGANISM: Arabidopsis thaliana

<400> SEQUENCE: 11

```
atggattctc aggacatcag ataccgcggc ggagacgaca gagacgctgc aacgacggct      60
atggccgaga cagagaggaa aagcgctgac gacaacaaag gaaaacgcga tcaaagagg      120
gcgatggcga acgtggtct caagtctctg acggtagcgg ttgcggctcc tgtgctcgtg      180
acgctcttcg ctacgtattt cctcggcaca agcgacggat acgggaatcg agctaagtcc      240
tcgtcgtgga tcccacctct gtggctccta cacacaacgt gtctcgcttc tagtggtctg      300
atgggtttgg ctgcgtggct tgtatgggtt gacggtggct ccacaagaa gcccaatgct      360
ctggctcttt acttagctca gttttttgctc tgtttggttt gggatccggt tacgttccgc      420
gtcgggtcgg gagtagcggg gcttgcggtg tggttgggtc aatcggctgc gttattcgga      480
tgctacaagg cctttaatga gataagtccg gtcgctggta atctggtaaa gccgtgtttg      540
gcttgggctg cctttgtagc cgctgttaat gtaaagcttg cagtcgcgtg a              591
```

<210> SEQ ID NO 12
<211> LENGTH: 196
<212> TYPE: PRT
<213> ORGANISM: Arabidopsis thaliana

<400> SEQUENCE: 12

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Pro Val Leu Val Thr Leu Phe Ala
    50                  55                  60

Thr Tyr Phe Leu Gly Thr Ser Asp Gly Tyr Gly Asn Arg Ala Lys Ser
65              70                  75                  80

Ser Ser Trp Ile Pro Pro Leu Trp Leu His Thr Thr Cys Leu Ala
            85                  90                  95

Ser Ser Gly Leu Met Gly Leu Ala Ala Trp Leu Val Trp Val Asp Gly
            100                 105                 110

Gly Phe His Lys Lys Pro Asn Ala Leu Ala Leu Tyr Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175

Lys Pro Cys Leu Ala Trp Ala Ala Phe Val Ala Val Asn Val Lys
            180              185              190

Leu Ala Val Ala
        195

<210> SEQ ID NO 13
<211> LENGTH: 591
<212> TYPE: DNA
<213> ORGANISM: Arabidopsis thaliana

<400> SEQUENCE: 13
atggattctc aggacatcag ataccgcggc ggagacgaca gagacgctgc aacgacggct      60
atggccgaga cagagaggaa agcgctgac gacaacaaag gaaaacgcga tcaaaagagg     120
gcgatggcga acgtggtct caagtctctg acggtagcgg ttgcggctcc tgtgctcgtg     180
acgctcttcg ctacgtattt cctcggcaca agcgacggat acgggaatcg agctaagtcc     240
tcgtcgtgga tcccacctct gtggctccta cacacaacgt gtctcgcttc tagtggtctg     300
atgggttggg ctgcgtggct tgtatgggtt gacggtggct ccacaagaa gcccaatgct     360 ctgtatcttg ctttagctca gtttttgctc tgtttggttt gggatccggt tacgttccgc     420
gtcgggtcgg gagtagcggg gcttgcggtg tggttgggtc aatcggctgc gttattcgga     480
tgctacaagg cctttaatga gataagtccg gtcgctggta atctggtaaa gccgtgtttg     540
gcttgggctg cctttgtagc cgctgttaat gtaaagcttg cagtcgcgtg a              591

<210> SEQ ID NO 14
<211> LENGTH: 196
<212> TYPE: PRT
<213> ORGANISM: Arabidopsis thaliana

<400> SEQUENCE: 14

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Pro Val Leu Val Thr Leu Phe Ala
    50                  55                  60

Thr Tyr Phe Leu Gly Thr Ser Asp Gly Tyr Gly Asn Arg Ala Lys Ser
65              70                  75                  80

Ser Ser Trp Ile Pro Pro Leu Trp Leu His Thr Thr Cys Leu Ala
            85                  90                  95

Ser Ser Gly Leu Met Gly Leu Ala Ala Trp Leu Val Trp Val Asp Gly
            100                 105                 110

Gly Phe His Lys Lys Pro Asn Ala Leu Tyr Leu Ala Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175

Lys Pro Cys Leu Ala Trp Ala Ala Phe Val Ala Val Asn Val Lys
            180                 185                 190

Leu Ala Val Ala
        195

<210> SEQ ID NO 15
<211> LENGTH: 591
<212> TYPE: DNA
<213> ORGANISM: Arabidopsis thaliana

<400> SEQUENCE: 15
atggattctc aggacatcag ataccgcggc ggagacgaca gagacgctgc aacgacggct    60
atggccgaga cagagaggaa aagcgctgac gacaacaaag gaaaacgcga tcaaagagg    120 gcgatggcga acgtggtct caagtctctg acggtagcgg ttgcggctcc tgtgctcgtg    180
acgctcttcg ctacgtattt cctcggcaca agcgacggat acgggaatcg agctaagtcc    240
tcgtcgtgga tcccacctct gtggctccta cacacaacgt gtctcgcttc tagtggtctg    300
atgggtttgg ctgcgtggct tgtatgggtt gacggtggct ccacaagaa gcccaatgct    360 ctggctcttg ctttagctca gttttttgctc tgtttggttt gggatccggt tacgttccgc    420
gtcgggtcgg gagtagcggg gcttgcggtg tggttgggtc aatcggctgc gttattcgga    480
tgctacaagg cctttaatga gataagtccg gtcgctggta atctggtaaa gccgtgtttg    540
gcttgggctg cctttgtagc cgctgttaat gtaaagcttg cagtcgcgtg a             591

<210> SEQ ID NO 16
<211> LENGTH: 196
<212> TYPE: PRT
<213> ORGANISM: Arabidopsis thaliana

<400> SEQUENCE: 16

Met Asp Ser Gln Asp Ile Arg Tyr Arg Gly Gly Asp Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser Leu Thr Val Ala Val Ala Pro Val Leu Val Thr Leu Phe Ala
    50                  55                  60

Thr Tyr Phe Leu Gly Thr Ser Asp Gly Tyr Gly Asn Arg Ala Lys Ser
65                  70                  75                  80

Ser Ser Trp Ile Pro Pro Leu Trp Leu His Thr Thr Cys Leu Ala
            85                  90                  95

Ser Ser Gly Leu Met Gly Leu Ala Ala Trp Leu Val Trp Val Asp Gly
            100                 105                 110

Gly Phe His Lys Lys Pro Asn Ala Leu Ala Leu Ala Leu Ala Gln Phe
        115                 120                 125

Leu Leu Cys Leu Val Trp Asp Pro Val Thr Phe Arg Val Gly Ser Gly
    130                 135                 140

Val Ala Gly Leu Ala Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175

Lys Pro Cys Leu Ala Trp Ala Ala Phe Val Ala Val Asn Val Lys
            180                 185                 190

Leu Ala Val Ala
        195

<210> SEQ ID NO 17
<211> LENGTH: 537
<212> TYPE: DNA
<213> ORGANISM: Brassica napus

<400> SEQUENCE: 17

```
atggattctc aggacatcag gtaccgtgcc ggagacgccg ctatggctga gacggagagg    60
aaacaagccg acgacaacaa caacaacaaa ggcaaacgcg atcaaaagag ggcgatggct   120
aaacgcggtc tcaaatccct gacgttagct gttgcagctc ctgtgctcct gactctcttc   180
acatcctact tcctcgggaa tcaggctcgg tcctcgtcgt gggtccttca cctcatgcgt   240
ctcgcctcga gcggtctgat gggcttggct gcgtggctcg tatgggtcga cgctgggttc   300
cacaagaagc ccaacgctct gtatctttac ttggctcagt ttgtgctttg tttgactacg   360
tgcatggtcg ggtcgggact agcagggctt gcagtgtgct tgtgtcagtc tgcggccttg   420
ttccgatgct acaaggcctt taatgagacc agtccggtcg ctggtaatat ggtaatgccg   480
tgtttggctt ttgctgcgtt tgtagcagcc gttaatgtga agctagcaat cgcgtga      537
```

<210> SEQ ID NO 18
<211> LENGTH: 178
<212> TYPE: PRT
<213> ORGANISM: Brassica napus

<400> SEQUENCE: 18

Met Asp Ser Gln Asp Ile Arg Tyr Arg Ala Gly Asp Ala Ala Met Ala
1               5                   10                  15

Glu Thr Glu Arg Lys Gln Ala Asp Asp Asn Asn Asn Asn Lys Gly Lys
            20                  25                  30

Arg Asp Gln Lys Arg Ala Met Ala Lys Arg Gly Leu Lys Ser Leu Thr
        35                  40                  45

Leu Ala Val Ala Ala Pro Val Leu Leu Thr Leu Phe Thr Ser Tyr Phe
    50                  55                  60

Leu Gly Asn Gln Ala Arg Ser Ser Ser Trp Val Leu His Leu Met Arg
65                  70                  75                  80

Leu Ala Ser Ser Gly Leu Met Gly Leu Ala Ala Trp Leu Val Trp Val
                85                  90                  95

Asp Ala Gly Phe His Lys Lys Pro Asn Ala Leu Tyr Leu Tyr Leu Ala
            100                 105                 110

Gln Phe Val Leu Cys Leu Thr Thr Cys Met Val Gly Ser Gly Leu Ala
        115                 120                 125

Gly Leu Ala Val Cys Leu Cys Gln Ser Ala Ala Leu Phe Arg Cys Tyr
    130                 135                 140

Lys Ala Phe Asn Glu Thr Ser Pro Val Ala Gly Asn Met Val Met Pro
145                 150                 155                 160

Cys Leu Ala Phe Ala Ala Phe Val Ala Ala Val Asn Val Lys Leu Ala
                165                 170                 175

Ile Ala

```
<210> SEQ ID NO 19
<211> LENGTH: 588
<212> TYPE: DNA
<213> ORGANISM: Brassica napus

<400> SEQUENCE: 19
atggattctc aggacacagt caggcatcgt ggaggagacg aaagagacgc ggcaaccacc      60
gctacggccg agacggacag gaaacacgca gatgacaaca acaaaggcca acgcgaccaa     120
aagagggcga tggccaaacg cggtcttaaa tcgcttacgg tagcggttgc ggctcctgtg     180
ctcgtgatgc tcttcgaaac gtatttcctc ggcggctacg gcagtcgtgc tcggtcctcg     240
tcgtggatcc cacctccgtg gtcctacac gtcactcgcc tggcgtcgag cggtctgatg      300
ggcttggctg cgtggctcgt atgggtggac ggtggattcc acaagaagcc taatgctctg     360
tatctttact tggctcagtt tacgctttgt ttgctttggg gtccggttac gttcctggtc     420
gggtcaggat tggccgggct tgtggtgtgg ctgggtcagt ctgcggcctt gtttggatgc     480
tacaaggcct ttaatgagat cagtcctgtc gctggtaatt tggtaaagcc gtgtttggct     540
tgtactgcgt ttgtagctgc cgtgaatgta aagctcgcaa tcgcctga                 588

<210> SEQ ID NO 20
<211> LENGTH: 195
<212> TYPE: PRT
<213> ORGANISM: Brassica napus

<400> SEQUENCE: 20

Met Asp Ser Gln Asp Thr Val Arg His Arg Gly Gly Asp Glu Arg Asp
1               5                   10                  15

Ala Ala Thr Thr Ala Thr Ala Glu Thr Asp Arg Lys His Ala Asp Asp
            20                  25                  30

Asn Asn Lys Gly Gln Arg Asp Gln Lys Arg Ala Met Ala Lys Arg Gly
        35                  40                  45

Leu Lys Ser Leu Thr Val Ala Val Ala Ala Pro Val Leu Val Met Leu
    50                  55                  60

Phe Glu Thr Tyr Phe Leu Gly Gly Tyr Gly Ser Arg Ala Arg Ser Ser
65                  70                  75                  80

Ser Trp Ile Pro Pro Trp Val Leu His Val Thr Arg Leu Ala Ser
                85                  90                  95

Ser Gly Leu Met Gly Leu Ala Ala Trp Leu Val Trp Val Asp Gly Gly
            100                 105                 110

Phe His Lys Lys Pro Asn Ala Leu Tyr Leu Tyr Leu Ala Gln Phe Thr
        115                 120                 125

Leu Cys Leu Leu Trp Gly Pro Val Thr Phe Leu Val Gly Ser Gly Leu
    130                 135                 140

Ala Gly Leu Val Val Trp Leu Gly Gln Ser Ala Leu Phe Gly Cys
145                 150                 155                 160

Tyr Lys Ala Phe Asn Glu Ile Ser Pro Val Ala Gly Asn Leu Val Lys
                165                 170                 175

Pro Cys Leu Ala Cys Thr Ala Phe Val Ala Ala Val Asn Val Lys Leu
            180                 185                 190

Ala Ile Ala
        195

<210> SEQ ID NO 21
<211> LENGTH: 549
<212> TYPE: DNA
<213> ORGANISM: Brassica napus
```

<400> SEQUENCE: 21

```
atggattctc aggacatcag gtcccgtgcc ggagacgccg caatggctga gaccgagagg      60
aaacacgcct ccgacgtaaa caacaagggg aaacgcgatc aaagagggc gatggctaaa     120 cgcggtctca aatccctgac gttagctgtt gcagctcctg tgctcctgac tctcttcgca     180
tcctacttcc tcgggaatcg ggctcggtct cctcgtggga ttctacctct gtgggtcctt     240
cacctcatgc gtctcgcctc gagcggtctg atgggcttgg ctgcgtggct cgtatgggtc     300
gacggtgggt tccacaagaa gcccaacgct ctctatcttt acttggctca gtttgtgctt     360
tctttgacta cgtgcatggt cgggtcggga ctagcagggc ttgcagtgtg cttgggtcag     420
tctgcggcct tgttcggatg ctacaaggcc tttaatgaga ccagtccggt cgctggtaat     480
atggtaaagc cgtgtttggc ttttgctgcg tttgtagcag ccgttaatgt aaagctagca     540
atcgcgtaa                                                              549
```

<210> SEQ ID NO 22
<211> LENGTH: 182
<212> TYPE: PRT
<213> ORGANISM: Brassica napus

<400> SEQUENCE: 22

```
Met Asp Ser Gln Asp Ile Arg Ser Arg Ala Gly Asp Ala Ala Met Ala
 1               5                  10                  15

Glu Thr Glu Arg Lys His Ala Ser Asp Val Asn Asn Lys Gly Lys Arg
            20                  25                  30

Asp Gln Lys Arg Ala Met Ala Lys Arg Gly Leu Lys Ser Leu Thr Leu
        35                  40                  45

Ala Val Ala Ala Pro Val Leu Leu Thr Leu Phe Ala Ser Tyr Phe Leu
    50                  55                  60

Gly Asn Arg Ala Arg Ser Ser Ser Trp Ile Leu Pro Leu Trp Val Leu
65                  70                  75                  80

His Leu Met Arg Leu Ala Ser Ser Gly Leu Met Gly Leu Ala Ala Trp
                85                  90                  95

Leu Val Trp Val Asp Gly Gly Phe His Lys Lys Pro Asn Ala Leu Tyr
            100                 105                 110

Leu Tyr Leu Ala Gln Phe Val Leu Ser Leu Thr Thr Cys Met Val Gly
        115                 120                 125

Ser Gly Leu Ala Gly Leu Ala Val Cys Leu Gly Gln Ser Ala Ala Leu
    130                 135                 140

Phe Gly Cys Tyr Lys Ala Phe Asn Glu Thr Ser Pro Val Ala Gly Asn
145                 150                 155                 160

Met Val Lys Pro Cys Leu Ala Phe Ala Ala Phe Val Ala Ala Val Asn
                165                 170                 175

Val Lys Leu Ala Ile Ala
            180
```

<210> SEQ ID NO 23
<211> LENGTH: 591
<212> TYPE: DNA
<213> ORGANISM: Brassica napus

<400> SEQUENCE: 23

```
atggattctc aggacatcag gcatcgtgga ggagacgaca gagacgcagc aaccaccgct      60
atggccgaga cggacaggaa acaggcagat gacaacaaca aaggccaacg cgaccaaaag     120
agggcgatgg ccaaacgcgg tcttaaatcg ctaacggtag cggttgcggc tcctgtgctc     180
```

```
gtgatgctct tcgaaacgta tttcctcggc ggcggcggct acggcagtcg tgctcggtcc    240
tcgtcgtgga tcccacctcc gtgggtccta cacgccactc gcctggcgtc gagcggtctg    300
atgggcttgg ctgcgtggct cgtatgggtg gacggtggat tccacaagaa gcccaatgct    360
ctgtatcttt acttggctca gtttacgctt tgtttgcttt ggggtccggt tacgttcctg    420
gtcgggtcag gattagccgg gcttgtggtg tggttaggcc aatctgcggc cttgttcgga    480
tgctacaagg cctttaatga gatcagtccg gtagctggta atctggtaaa gccgtgtttg    540
gcttgtgctg cgtttgttac tgccgtgaat gtaaagctcg caatcgcctg a             591
```

```
<210> SEQ ID NO 24
<211> LENGTH: 196
<212> TYPE: PRT
<213> ORGANISM: Brassica napus

<400> SEQUENCE: 24

Met Asp Ser Gln Asp Ile Arg His Arg Gly Gly Asp Asp Arg Asp Ala
1               5                   10                  15

Ala Thr Thr Ala Met Ala Glu Thr Asp Arg Lys Gln Ala Asp Asp Asn
            20                  25                  30

Asn Lys Gly Gln Arg Asp Gln Lys Arg Ala Met Ala Lys Arg Gly Leu
        35                  40                  45

Lys Ser Leu Thr Val Ala Val Ala Ala Pro Val Leu Val Met Leu Phe
    50                  55                  60

Glu Thr Tyr Phe Leu Gly Gly Gly Tyr Gly Ser Arg Ala Arg Ser
65                  70                  75                  80

Ser Ser Trp Ile Pro Pro Pro Trp Val Leu His Ala Thr Arg Leu Ala
                85                  90                  95

Ser Ser Gly Leu Met Gly Leu Ala Ala Trp Leu Val Trp Val Asp Gly
            100                 105                 110

Gly Phe His Lys Lys Pro Asn Ala Leu Tyr Leu Tyr Leu Ala Gln Phe
        115                 120                 125

Thr Leu Cys Leu Leu Trp Gly Pro Val Thr Phe Leu Val Gly Ser Gly
    130                 135                 140

Leu Ala Gly Leu Val Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175

Lys Pro Cys Leu Ala Cys Ala Ala Phe Val Thr Ala Val Asn Val Lys
            180                 185                 190

Leu Ala Ile Ala
        195
```

```
<210> SEQ ID NO 25
<211> LENGTH: 537
<212> TYPE: DNA
<213> ORGANISM: Brassica rapa

<400> SEQUENCE: 25
atggattctc aggacatcag gtaccgtgcc ggagacgccg ctatggctga cacggagagg     60
aaacaagccg acgacaacaa caacaacaaa ggcaaacgcg atcaaaagag gcgatggct    120 aaacgcggtc tcaaatccct gacgttagct gttgcagctc ctgtgctcct gactctcttc    180
acatcctact tcctcgggaa tcaggctcgg tcctcgtcgt gggtccttca cctcatgcgt    240
ctcgcctcga gcggtctgat gggcttggct gcgtggctcg tatgggtcga cgctgggttc    300
```

```
cacaagaagc ccaacgctct gtatctttac ttggctcagt ttgtgctttg tttgactacg   360
tgcatggtcg ggtcgggact agcagggctt gcagtgtgct tgtgtcagtc tgcggccttg   420
ttcggatgct acaaggcctt taatgagatc agtccggtcg ctggtaatat ggtaaagccg   480
tgtttggctt tgctgcgtt tgtagcagcc gttaatgtaa agctcgcaat cgcgtga      537
```

```
<210> SEQ ID NO 26
<211> LENGTH: 178
<212> TYPE: PRT
<213> ORGANISM: Brassica rapa

<400> SEQUENCE: 26

Met Asp Ser Gln Asp Ile Arg Tyr Arg Ala Gly Asp Ala Ala Met Ala
1               5                   10                  15

Glu Thr Glu Arg Lys Gln Ala Asp Asp Asn Asn Asn Lys Gly Lys
            20                  25                  30

Arg Asp Gln Lys Arg Ala Met Ala Lys Arg Gly Leu Lys Ser Leu Thr
        35                  40                  45

Leu Ala Val Ala Ala Pro Val Leu Leu Thr Leu Phe Thr Ser Tyr Phe
    50                  55                  60

Leu Gly Asn Gln Ala Arg Ser Ser Ser Trp Val Leu His Leu Met Arg
65                  70                  75                  80

Leu Ala Ser Ser Gly Leu Met Gly Leu Ala Ala Trp Leu Val Trp Val
                85                  90                  95

Asp Ala Gly Phe His Lys Lys Pro Asn Ala Leu Tyr Leu Tyr Leu Ala
            100                 105                 110

Gln Phe Val Leu Cys Leu Thr Thr Cys Met Val Gly Ser Gly Leu Ala
        115                 120                 125

Gly Leu Ala Val Cys Leu Cys Gln Ser Ala Ala Leu Phe Gly Cys Tyr
    130                 135                 140

Lys Ala Phe Asn Glu Ile Ser Pro Val Ala Gly Asn Met Val Lys Pro
145                 150                 155                 160

Cys Leu Ala Phe Ala Ala Phe Val Ala Ala Val Asn Val Lys Leu Ala
                165                 170                 175

Ile Ala
```

```
<210> SEQ ID NO 27
<211> LENGTH: 591
<212> TYPE: DNA
<213> ORGANISM: Brassica rapa

<400> SEQUENCE: 27
atggattctc aggacatcag gcatcgtgga ggagacgaca gagacgcagc aaccaccgct   60
atggccgaga cggacaggaa acaggcagat gacaacaaca aaggccaacg cgaccaaaag  120
agggcgatgg ccaaacgcgg tcttaaatcg ctaacggtag cggttgcggc tcctgtgctc  180
gtgatgctct cgaaacgta tttcctcggc ggcggcggct acggcagtcg tgctcggtcc  240
tcgtcgtgga tcccacctcc gtgggtccta cacgccactc gcctggcgtc gcgcggtctg  300
atgggcttgg ctgcgtggct cgtatgggtg acggtgggt tccacaagaa gcccaatgct  360
ctgtatcttt acttggctca gtttacgctt tgtttgcttt ggggtccggt tacgttcctg  420
gtcgggtcag gagtagccgg gcttgtggtg tggttaggcc aatctgcggc cttgttcgga  480
tgctacaagg cctttaatga gatcagtccg gtagctggta atctggtaaa gccgtgtttg  540
gcttgtgctg cgtttgttac tgccgtgaat gtaaagctcg caatcgcctg a          591
```

```
<210> SEQ ID NO 28
<211> LENGTH: 196
<212> TYPE: PRT
<213> ORGANISM: Brassica rapa

<400> SEQUENCE: 28

Met Asp Ser Gln Asp Ile Arg His Arg Gly Gly Asp Asp Arg Asp Ala
1               5                   10                  15

Ala Thr Thr Ala Met Ala Glu Thr Asp Arg Lys Gln Ala Asp Asp Asn
            20                  25                  30

Asn Lys Gly Gln Arg Asp Gln Lys Arg Ala Met Ala Lys Arg Gly Leu
        35                  40                  45

Lys Ser Leu Thr Val Ala Val Ala Ala Pro Val Leu Val Met Leu Phe
    50                  55                  60

Glu Thr Tyr Phe Leu Gly Gly Gly Tyr Gly Ser Arg Ala Arg Ser
65                  70                  75                  80

Ser Ser Trp Ile Pro Pro Trp Val Leu His Ala Thr Arg Leu Ala
                85                  90                  95

Ser Arg Gly Leu Met Gly Leu Ala Ala Trp Leu Val Trp Val Asp Gly
            100                 105                 110

Gly Phe His Lys Lys Pro Asn Ala Leu Tyr Leu Tyr Leu Ala Gln Phe
        115                 120                 125

Thr Leu Cys Leu Leu Trp Gly Pro Val Thr Phe Leu Val Gly Ser Gly
    130                 135                 140

Val Ala Gly Leu Val Val Trp Leu Gly Gln Ser Ala Ala Leu Phe Gly
145                 150                 155                 160

Cys Tyr Lys Ala Phe Asn Glu Ile Ser Pro Val Ala Gly Asn Leu Val
                165                 170                 175

Lys Pro Cys Leu Ala Cys Ala Ala Phe Val Thr Ala Val Asn Val Lys
            180                 185                 190

Leu Ala Ile Ala
        195

<210> SEQ ID NO 29
<211> LENGTH: 582
<212> TYPE: DNA
<213> ORGANISM: Oryza sativa

<400> SEQUENCE: 29
atggcctccg ccgccgccgc cgccgccgcc gcgcaggaag ggatcactca ccgcgccgtg      60
agaggggatg gcggcgatgc tgcggcgacg gcgggtggtg gcgaggcggc gagccgggat     120
ccgaggaagg cggggcgcgc caagcgcggg ctgcggtcgc tcgccgccgc cgtgtccgtg     180
tcggttgcgc tgatggccgc ctcgttctac ggctccgggt cggcgtcggc gtcggcgtcg     240
gcggcgaggg tgacggtcgc gcgggcgggg tcggtggcgg cggaggcggt gatggcgctg     300
gcggcgtgga tggtgtgggc ggagggcggg ctccaccgcc gccccggcgc gacgctggcg     360
ccgttcgtgg cgcagctggt cgccgcgctg cgtgggcgc cgctcgcgct ggggctcgcc     420
gcgcccgcgg ccgggctggc gtgctgcgcg gcgatggccg ccgcgccgc ggcgtgcgcg     480 cgcgggttcg gcggcgtcaa ccccgtcgcc ggcgacctcg ccaagccgtg cgtcgcctgg     540
gccgtcctcc tcgcagtcat caactacaag atgatgaact ga                      582

<210> SEQ ID NO 30
<211> LENGTH: 193
<212> TYPE: PRT
<213> ORGANISM: Oryza sativa
```

<400> SEQUENCE: 30

Met Ala Ser Ala Ala Ala Ala Ala Ala Gln Glu Gly Ile Thr
1               5                   10                  15

His Arg Ala Val Arg Gly Asp Gly Asp Ala Ala Thr Ala Gly
            20                  25                  30

Gly Gly Glu Ala Ala Ser Arg Asp Pro Arg Lys Ala Gly Arg Ala Lys
        35                  40                  45

Arg Gly Leu Arg Ser Leu Ala Ala Val Ser Val Ser Val Ala Leu
        50                  55                  60

Met Ala Ala Ser Phe Tyr Gly Ser Gly Ala Ser Ala Ser Ala Ser
65              70                  75                  80

Ala Ala Arg Val Thr Val Ala Arg Ala Gly Ser Val Ala Ala Glu Ala
                85                  90                  95

Val Met Ala Leu Ala Ala Trp Met Val Trp Ala Glu Gly Gly Leu His
            100                 105                 110

Arg Arg Pro Gly Ala Thr Leu Ala Pro Phe Val Ala Gln Leu Val Ala
            115                 120                 125

Ala Leu Ala Trp Ala Pro Leu Ala Leu Gly Leu Ala Ala Pro Ala Ala
            130                 135                 140

Gly Leu Ala Cys Cys Ala Ala Met Ala Ala Gly Ala Ala Ala Cys Ala
145                 150                 155                 160

Arg Gly Phe Gly Gly Val Asn Pro Val Ala Gly Asp Leu Ala Lys Pro
                165                 170                 175

Cys Val Ala Trp Ala Val Leu Leu Ala Val Ile Asn Tyr Lys Met Met
            180                 185                 190

Asn

<210> SEQ ID NO 31
<211> LENGTH: 591
<212> TYPE: DNA
<213> ORGANISM: Camelina sativa

<400> SEQUENCE: 31
atggattctc aggacatcag gtaccgtggc ggagacgaca gagacgccgc aacgacggct      60
atggccgaga cggaaaggaa acacgctgac gacaacaaag ggaaactcca tcaaaaaagg     120
gccatggcga aacgcggtct caggtctctg accgtagcag ttgcggctcc tgtcctcgtg     180
acgctcttcg ccacgttttt cctcggcaca agcgacggct acgggaaccg tgctcggtca     240
tcgtcatgga tcccacctct atggctccta cacaccacgt gtctcgcgtc gagctgtctc     300
atgggcctgg ctgcgtggct cgtatgggtc gacggtggtt ccacaagaa gcctaatgct     360 ttgtatcttt acttggctca gttttagtt tgtttgcttt gggatccggt acgtttcgg      420 ctcgggtcgg gaatagcggg gcttgcgtg tggttgggtc aatctgcggc gttattcggg      480
tgtttcaagg cctttagtga gataagcccg gtcgctggta atttggtaaa gccgtgtctg     540
gcttgggctg cgtttgtagc cgctgttaat gtaaagcttg caatcgcgta a              591

<210> SEQ ID NO 32
<211> LENGTH: 196
<212> TYPE: PRT
<213> ORGANISM: Camelina sativa

<400> SEQUENCE: 32

```
Met Asp Ser Gln Asp Ile Arg Tyr Arg Gly Gly Asp Arg Asp Ala
1               5                   10                  15

Ala Thr Thr Ala Met Ala Glu Thr Glu Arg Lys His Ala Asp Asp Asn
                20                  25                  30

Lys Gly Lys Leu His Gln Lys Arg Ala Met Ala Lys Arg Gly Leu Arg
            35                  40                  45

Ser Leu Thr Val Ala Val Ala Ala Pro Val Leu Val Thr Leu Phe Ala
        50                  55                  60

Thr Phe Phe Leu Gly Thr Ser Asp Gly Tyr Gly Asn Arg Ala Arg Ser
65                  70                  75                  80

Ser Ser Trp Ile Pro Pro Leu Trp Leu Leu His Thr Thr Cys Leu Ala
                85                  90                  95

Ser Ser Cys Leu Met Gly Leu Ala Ala Trp Leu Val Trp Val Asp Gly
                100                 105                 110

Gly Phe His Lys Lys Pro Asn Ala Leu Tyr Leu Tyr Leu Ala Gln Phe
            115                 120                 125

Leu Val Cys Leu Leu Trp Asp Pro Val Thr Phe Arg Leu Gly Ser Gly
        130                 135                 140

Ile Ala Gly Leu Ala Val Trp Leu Gly Gln Ser Ala Ala Leu Phe Gly
145                 150                 155                 160

Cys Phe Lys Ala Phe Ser Glu Ile Ser Pro Val Ala Gly Asn Leu Val
                165                 170                 175

Lys Pro Cys Leu Ala Trp Ala Ala Phe Val Ala Val Asn Val Lys
            180                 185                 190

Leu Ala Ile Ala
        195
```

<210> SEQ ID NO 33
<211> LENGTH: 546
<212> TYPE: DNA
<213> ORGANISM: Linum usitatissimum

<400> SEQUENCE: 33

```
atgaatacat cagggacaaa caacataagc agtacgagag accaaggaga gaagaggatg      60
gtcatggcaa agaggggct acggtcgctt gccgtagccc taggtcttcc tccttcccta     120
acgattctaa gcatctactt cctcggtggc ggtggctaca acagcgacga cgagctattg     180
ccggtgtcgt cgtataagaa gccgttttgg ttcccaccat cgtgggtgat ccacgttttt     240
tgcgtgacta gcacttttt aatgggcctt tctgggtggc tagtttgggc ggagggtagg     300
tttcacaacg aacctgcgac attgtacata tatggagtcc agatgggatt caactcgatt     360
ttgatcccga ttgtgtgtgg gttaaatatc ccatcattag ggctcatcat atctatgtgt     420
ttgcttgggg cactaataag ctgttctcgc cattttagga tcacgaatcc tattgctgct     480
gatttggtca agccatgcat tgcttgggct gccttcttga ttattctcaa tctcaaactc     540
atttag                                                                546
```

<210> SEQ ID NO 34
<211> LENGTH: 181
<212> TYPE: PRT
<213> ORGANISM: Linum usitatissimum -continued

<400> SEQUENCE: 34

Met Asn Thr Ser Gly Thr Asn Asn Ile Ser Ser Thr Arg Asp Gln Gly
1               5                   10                  15

Glu Lys Arg Met Val Met Ala Lys Arg Gly Leu Arg Ser Leu Ala Val
            20                  25                  30

Ala Leu Gly Leu Pro Pro Ser Leu Thr Ile Leu Ser Ile Tyr Phe Leu
        35                  40                  45

Gly Gly Gly Tyr Asn Ser Asp Asp Glu Leu Leu Pro Val Ser Ser
    50                  55                  60

Tyr Lys Lys Pro Phe Trp Phe Pro Pro Ser Trp Val Ile His Val Phe
65                  70                  75                  80

Cys Val Thr Ser Thr Phe Leu Met Gly Leu Ser Gly Trp Leu Val Trp
                85                  90                  95

Ala Glu Gly Arg Phe His Asn Glu Pro Ala Thr Leu Tyr Ile Tyr Gly
            100                 105                 110

Val Gln Met Gly Phe Asn Ser Ile Leu Ile Pro Ile Val Cys Gly Leu
        115                 120                 125

Asn Ile Pro Ser Leu Gly Leu Ile Ile Ser Met Cys Leu Leu Gly Ala
130                 135                 140

Leu Ile Ser Cys Ser Arg His Phe Arg Ile Thr Asn Pro Ile Ala Ala
145                 150                 155                 160

Asp Leu Val Lys Pro Cys Ile Ala Trp Ala Ala Phe Leu Ile Ile Leu
                165                 170                 175

Asn Leu Lys Leu Ile
            180

<210> SEQ ID NO 35
<211> LENGTH: 582
<212> TYPE: DNA
<213> ORGANISM: Zea mays

<400> SEQUENCE: 35
atggccaccg cacaggaagg tctgacccag cgcgtcgttg ccagtgccag cagggacgac      60
ggcgccggcg agagcgcggc ggccgtctcg ggtcccaaca agaagccggg cggcggccgc     120
gcaaacagca gcaggcgtgg gctccgttcg ctcgccgccg cggtgtcctt ctccgtggcg     180
ctcacggcgc tgtcgttctt cgccgcgggg cagtcgccac cgtcgcccaa gaccgccacg     240
gcgtcgactg tggcggtggt gcgggccggg tcggtggcgt tggaggcggt gctggcgctg     300
gcggcgtgga tggcgtgggc ggagggcggg ctgcacgcgc cccggcagc acgctgctc      360
ccctatgccg cgcacctggg cgccgccctc gcatgggcgc cactcgtgct gtgcagccac     420
gccgcggcgc gcgcgggcct cgcctgctgc gccgtcatgg ccgcgggcgc cgtggcgtgc     480
gcgcgcgggt tcggcgccgt caaccccgtg gctggcgacc tcgcgaagcc cgccgtcgcc     540
tgggccgtca tcctcgccgt cgtcaactac aagatgctct ga                        582

<210> SEQ ID NO 36
<211> LENGTH: 193
<212> TYPE: PRT
<213> ORGANISM: Zea mays

<400> SEQUENCE: 36

Met Ala Thr Ala Gln Glu Gly Leu Thr Gln Arg Val Val Ala Ser Ala
1               5                   10                  15

Ser Arg Asp Asp Gly Ala Gly Glu Ser Ala Ala Ala Val Ser Gly Pro
            20                  25                  30

```
Asn Lys Lys Pro Gly Gly Gly Arg Ala Asn Ser Ser Arg Arg Gly Leu
         35                  40                  45

Arg Ser Leu Ala Ala Ala Val Ser Phe Ser Val Ala Leu Thr Ala Leu
 50                  55                  60

Ser Phe Phe Ala Ala Gly Gln Ser Pro Pro Ser Pro Lys Thr Ala Thr
65                  70                  75                  80

Ala Ser Thr Val Ala Val Arg Ala Gly Ser Val Ala Leu Glu Ala
                 85                  90                  95

Val Leu Ala Leu Ala Ala Trp Met Ala Trp Ala Glu Gly Gly Leu His
             100                 105                 110

Ala Arg Pro Ala Ala Thr Leu Leu Pro Tyr Ala Ala His Leu Gly Ala
             115                 120                 125

Ala Leu Ala Trp Ala Pro Leu Val Leu Cys Ser His Ala Ala Ala Arg
         130                 135                 140

Ala Gly Leu Ala Cys Cys Ala Val Met Ala Ala Gly Ala Val Ala Cys
145                 150                 155                 160

Ala Arg Gly Phe Gly Ala Val Asn Pro Val Ala Gly Asp Leu Ala Lys
                 165                 170                 175

Pro Ala Val Ala Trp Ala Val Ile Leu Ala Val Val Asn Tyr Lys Met
             180                 185                 190

Leu
```

<210> SEQ ID NO 37
<211> LENGTH: 507
<212> TYPE: DNA
<213> ORGANISM: Helianthus annuus

<400> SEQUENCE: 37

```
atgacttaca atgtcgcaag aacgagatct caaaagaaac catcaacagc tagccgtggt      60
atccgatcac tgagcctagc cattgtggtc cccgtgggtc tcaccctaac aaccatcata     120
tggtttggag agagcaacac ctacaagaac ctaacccgac ccttctggat ccctcccttg     180
tgggccatac acctaacctc tgtgtcaacg gctttcttaa tggggttatc ggcttggctc     240
gtgtgggccg agagcgggtt tcaccgcaaa cccatggcta tggttatgta cttggctcag     300
ctcgggcttg gcttggcttg gaacaagatc ttttttcaaaa cgggccccac tcaaatgggc     360
ttagccatga gtttgggcca attggttacc attttaattt gttcacaaat gtttagccgg     420
ataaatccaa tagccggtga catagtgaag ctttgtttgg tttggaccgg gttttttaacg     480
tctgtaaatc tatattatgt acttttag                                         507
```

<210> SEQ ID NO 38
<211> LENGTH: 168
<212> TYPE: PRT
<213> ORGANISM: Helianthus annuus

<400> SEQUENCE: 38

```
Met Thr Tyr Asn Val Ala Arg Thr Arg Ser Gln Lys Lys Pro Ser Thr
  1               5                  10                  15

Ala Ser Arg Gly Ile Arg Ser Leu Ser Leu Ala Ile Val Val Pro Val
             20                  25                  30

Gly Leu Thr Leu Thr Thr Ile Ile Trp Phe Gly Glu Ser Asn Thr Tyr
         35                  40                  45

Lys Asn Leu Thr Arg Pro Phe Trp Ile Pro Pro Leu Trp Ala Ile His
 50                  55                  60
```

Leu Thr Ser Val Ser Thr Ala Phe Leu Met Gly Leu Ser Ala Trp Leu
 65                  70                  75                  80

Val Trp Ala Glu Ser Gly Phe His Arg Lys Pro Met Ala Met Val Met
                 85                  90                  95

Tyr Leu Ala Gln Leu Gly Leu Gly Leu Ala Trp Asn Lys Ile Phe Phe
            100                 105                 110

Lys Thr Gly Pro Thr Gln Met Gly Leu Ala Met Ser Leu Gly Gln Leu
        115                 120                 125

Val Thr Ile Leu Ile Cys Ser Gln Met Phe Ser Arg Ile Asn Pro Ile
    130                 135                 140

Ala Gly Asp Ile Val Lys Leu Cys Leu Val Trp Thr Gly Phe Leu Thr
145                 150                 155                 160

Ser Val Asn Leu Tyr Tyr Val Leu
                165

<210> SEQ ID NO 39
<211> LENGTH: 576
<212> TYPE: DNA
<213> ORGANISM: Helianthus annuus

<400> SEQUENCE: 39
atggactcca cctcacaaga actcaaacac agagccacca ccaccaccac agaagaccaa      60
tctccaaccc ttcaacccaa cacaaaaact caaaaacaac gtatcccgac acgtggcatc     120
cgctcactgg ctgtcgggat cgcgatcccg ttagctctaa ccttagccaa catatctatc     180
ttcggctgga accgaaccta ccgaaccatc cacaaaccgt tctgggtccc accgttatgg     240
gctctacatt taacatgttt gggttcggct tttattatgg gttatcggc ttggcttgtt      300 tgggctgaag gggggtttca taagaaccgc agtgcggtcg gttttatttg gggcagttg      360 gggctgagcc tggcttggga cccggtgttt tttaagatgg gtgcggctag gttgggtttg     420
ttggtgtgtt tgggtcagat ggcgactatg tggtcttgtt tgaagatgtt tgggcgggtt     480
aaccggactg cgggtgattt gggtatggtg aaggggtttt ttgtgtatag aagtttatgc     540
tttcatgttt tgtggtcttg caatgtaata atatga                              576

<210> SEQ ID NO 40
<211> LENGTH: 191
<212> TYPE: PRT
<213> ORGANISM: Helianthus annuus

<400> SEQUENCE: 40

Met Asp Ser Thr Ser Gln Glu Leu Lys His Arg Ala Thr Thr Thr Thr
1               5                   10                  15

Thr Glu Asp Gln Ser Pro Thr Leu Gln Pro Asn Thr Lys Thr Gln Lys
            20                  25                  30

Gln Arg Ile Pro Thr Arg Gly Ile Arg Ser Leu Ala Val Gly Ile Ala
        35                  40                  45

Ile Pro Leu Ala Leu Thr Leu Ala Asn Ile Ser Ile Phe Gly Trp Asn
    50                  55                  60

Arg Thr Tyr Arg Thr Ile His Lys Pro Phe Trp Val Pro Pro Leu Trp
65                  70                  75                  80

Ala Leu His Leu Thr Cys Leu Gly Ser Ala Phe Ile Met Gly Leu Ser
                85                  90                  95

Ala Trp Leu Val Trp Ala Glu Gly Gly Phe His Lys Asn Pro Ser Ala
            100                 105                 110

```
    Val Gly Phe Tyr Leu Gly Gln Leu Gly Leu Ser Leu Ala Trp Asp Pro
            115                 120                 125

Val Phe Lys Met Gly Ala Ala Arg Leu Gly Leu Leu Val Cys Leu
        130                 135                 140

Gly Gln Met Ala Thr Met Trp Ser Cys Leu Lys Met Phe Gly Arg Val
    145                 150                 155                 160

Asn Arg Thr Ala Gly Asp Leu Gly Met Val Lys Gly Val Phe Val Tyr
                    165                 170                 175

Arg Ser Leu Cys Phe His Val Leu Trp Ser Cys Asn Val Ile Ile
                180                 185                 190

<210> SEQ ID NO 41
<211> LENGTH: 400
<212> TYPE: DNA
<213> ORGANISM: Arabidopsis thaliana

<400> SEQUENCE: 41
taggcgataa taagtgcgac taggattgca tcagcaagaa ttagcgcgaa tgcgaatgga      60
actgcaggtt ttttgaatag atcggatcga ttcgtctcct tccccagccg acggctacga    120
gaagctctca aactcgccgg tgatgaggcg cccgccatga aaacagagca atcgcatca     180 gcgtctagcc aacgccgcgt aacagacaac tacttccata ttactactct tctaattagc    240
ccaaattaaa tgagcctatt gggcttcttg tcttagtcgg tgtagagccc aattgttgtt    300 ttattttta ataatgcaaa agtattaagc gataaataaa taagcatcgc aatcgtccca     360
aaactgtgtg tatgcatcag acatgagcat atagagtaag                          400

<210> SEQ ID NO 42
<211> LENGTH: 1000
<212> TYPE: DNA
<213> ORGANISM: Linum usitatissimum

<400> SEQUENCE: 42
gccaatggaa cggctcaatt caattgaccc agggaattcc cgattggcca gagatgttga     60
aggaactgcc gccaatggaa gcgctattaa gtaaactaga aggtaaggg gagggctggg    120 gtgtctcatg atgtttgtat gtgagcaggt ctttcatgga aatttaaggg aatatgtaga    180
tggcggcggg gggatcatct acttactctg ttactgaagt cttactgtat cattgattga    240
accaagtcaa atgtatgtgt aagggcgtgt ttggctggtt ggttagtcta tggggcgagg    300
tcagatataa ataagggata caatgattga tttattgtgc ataccttcgt gtctactttt    360
cggttttggt ttctgtcaaa acggtttggt ttttgtagta atcaaattaa ctactgaata    420
ttggtcgttc ggagagttaa aaatcgagca actcacgagt tacctcatcg ctcgtatttt    480
tttagcttca cctttttgtg ggtgtcgcca cccctattta gttatgtgat tttgtaattc    540
atatttggtt accatacaaa cgggaggtat tggcttctta acaaaccaac aaaaaaatat    600
tttatttgtg tgttttctct tttggtattt tctgagcaaa aaattatttt gtatttcttc    660
ataacaaacc aacaaaaata tatatgcaag aatataatcc taaattttct cccataacac    720
aaattatttt atctggtttt ttaataattt attgtgtctt aactctttca atcttcccat    780
caaacctcat tcacttgttt cttctcttac cctatataga atggcataaa acatttcatt    840
gcttcttaat ctcttgtctc tagctccttc atgccctaat aagataaaaa agcgattcat    900
tttgcaatca actaacaaaa atatatctat tcatcgacat tccgagcatc gcgatctaca    960
ttctacaccc gagggcaaca acaacaacat cacaacgatg                         1000
```

```
<210> SEQ ID NO 43
<211> LENGTH: 200
<212> TYPE: DNA
<213> ORGANISM: Brassica napus

<400> SEQUENCE: 43
taccttgttt ttaaaaagaa tcgctcataa gatggcatgc cagaacatta gctacacgtt      60
acacaaagca tgcagacgcg gaggattgtt tttgttcgtc acttgtcact cccttcaaac     120
acctaagagc ttctctctca cagcacacac atacaatcac atgcgtgcat gcattattac     180
acgtgatcgc catgcaaatc                                                 200

<210> SEQ ID NO 44
<211> LENGTH: 786
<212> TYPE: DNA
<213> ORGANISM: Arabidopsis thaliana

<400> SEQUENCE: 44
ggttcttgag accgatgaga gatgggagca gaactaaaga tgatgacata attaagaacg      60
aatttgaaag gctcttaggt ttgaatccta ttcgagaatg tttttgtcaa agatagtggc     120
gattttgaac caaagaaaac atttaaaaaa tcagtatccg gttacgttca tgcaaataga     180
aagtggtcta ggatctgatt gtaattttag acttaaagag tctcttaaga ttcaatcctg     240
gctgtgtaca aaactacaaa taatatattt tagactattt ggccttaact aaacttccac     300
tcattattta ctgaggttag agaatagact tgcgaataaa cacattcccg agaaatactc     360
atgatcccat aattagtcag agggtatgcc aatcagatct aagaacacac attccctcaa     420
attttaatgc acatgtaatc atagtttagc acaattcaaa ataatgtag tattaaagac      480 agaaatttgt agactttttt ttggcgttaa agaagactaa gtttatacg tacatttttat     540 tttaagtgga aaaccgaaat tttccatcga aatatatgaa tttagtatat atatttctgc     600
aatgtactat tttgctattt tggcaacttt cagtggacta ctactttatt acaatgtgta     660
tggatgcatg agtttgagta tacacatgtc taaatgcatg ctttgtaaaa cgtaacggac     720
cacaaaagag gatccataca aatacatctc atagcttcct ccattatttt ccgacacaaa     780
cagagc                                                                786

<210> SEQ ID NO 45
<211> LENGTH: 38
<212> TYPE: DNA
<213> ORGANISM: Artificial Sequence
<220> FEATURE:
<223> OTHER INFORMATION: primer sequence SeM5'

<400> SEQUENCE: 45
aaatctagaa agcttaccat ggattctcag gacatcag                              38

<210> SEQ ID NO 46
<211> LENGTH: 36
<212> TYPE: DNA
<213> ORGANISM: Artificial Sequence
<220> FEATURE:
<223> OTHER INFORMATION: primer sequence SeM3'

<400> SEQUENCE: 46
aaaagatctt cacgcgactg caagctttac attaac                                36
```

```
<210> SEQ ID NO 47
<211> LENGTH: 39
<212> TYPE: DNA
<213> ORGANISM: Artificial Sequence
<220> FEATURE:
<223> OTHER INFORMATION: primer sequence NeM5'

<400> SEQUENCE: 47
aaactcgagg gtacctacct tgtttttaaa aagaatcgc                               39

<210> SEQ ID NO 48
<211> LENGTH: 30
<212> TYPE: DNA
<213> ORGANISM: Artificial Sequence
<220> FEATURE:
<223> OTHER INFORMATION: primer sequence NeM3'

<400> SEQUENCE: 48
aaatctagag atttgcatgg cgatcacgtg                                         30

<210> SEQ ID NO 49
<211> LENGTH: 144
<212> TYPE: PRT
<213> ORGANISM: Arabidopsis thaliana

<400> SEQUENCE: 49

Val Ala Val Ala Ala Pro Val Leu Val Thr Leu Phe Ala Thr Tyr Phe
1               5                   10                  15

Leu Gly Thr Ser Asp Gly Tyr Gly Asn Arg Ala Lys Ser Ser Ser Trp
            20                  25                  30

Ile Pro Pro Leu Trp Leu Leu His Thr Thr Cys Leu Ala Ser Ser Gly
        35                  40                  45

Leu Met Gly Leu Ala Ala Trp Leu Val Trp Val Asp Gly Gly Phe His
    50                  55                  60

Lys Lys Pro Asn Ala Leu Tyr Leu Tyr Leu Ala Gln Phe Leu Leu Cys
65                  70                  75                  80

Leu Val Trp Asp Pro Val Thr Phe Arg Val Gly Ser Gly Val Ala Gly
                85                  90                  95

Leu Ala Val Trp Leu Gly Gln Ser Ala Ala Leu Phe Gly Cys Tyr Lys
            100                 105                 110

Ala Phe Asn Glu Ile Ser Pro Val Ala Gly Asn Leu Val Lys Pro Cys
        115                 120                 125

Leu Ala Trp Ala Ala Phe Val Ala Val Asn Val Lys Leu Ala Val
    130                 135                 140

<210> SEQ ID NO 50
<211> LENGTH: 49
<212> TYPE: PRT
<213> ORGANISM: Arabidopsis thaliana

<400> SEQUENCE: 50

Met Asp Ser Gln Asp Ile Arg Tyr Arg Gly Gly Asp Arg Asp Ala
1               5                   10                  15

Ala Thr Thr Ala Met Ala Glu Thr Glu Arg Lys Ser Ala Asp Asp Asn
            20                  25                  30

Lys Gly Lys Arg Asp Gln Lys Arg Ala Met Ala Lys Arg Gly Leu Lys
        35                  40                  45

Ser
```

```
<210> SEQ ID NO 51
<211> LENGTH: 9
<212> TYPE: PRT
<213> ORGANISM: Arabidopsis thaliana

<400> SEQUENCE: 51

Met Ala Lys Arg Gly Leu Lys Ser Leu
1               5
```